US008691503B2

(12) United States Patent
Adorjan et al.

(10) Patent No.: US 8,691,503 B2
(45) Date of Patent: **\*Apr. 8, 2014**

(54) METHOD AND NUCLEIC ACIDS FOR THE ANALYSIS OF COLORECTAL CELL PROLIFERATIVE DISORDERS

(75) Inventors: Peter Adorjan, Berlin (DE); Matthias Burger, Berlin (DE); Sabine Maier, Brussels (BE); Ralf Lesche, Berlin (DE); Susan Cottrell, Seattle, WA (US); Theo De Vos, Seattle, WA (US)

(73) Assignee: Epigenomics AG, Berlin (DE)

( * ) Notice: Subject to any disclaimer, the term of this patent is extended or adjusted under 35 U.S.C. 154(b) by 1380 days.

This patent is subject to a terminal disclaimer.

(21) Appl. No.: 10/482,823

(22) PCT Filed: Feb. 13, 2003

(86) PCT No.: PCT/EP03/01457
§ 371 (c)(1),
(2), (4) Date: Jul. 12, 2004

(87) PCT Pub. No.: WO03/072812
PCT Pub. Date: Sep. 4, 2003

(65) Prior Publication Data
US 2005/0003463 A1 Jan. 6, 2005

(30) Foreign Application Priority Data

Feb. 27, 2002 (EP) .................................. 02004551

(51) Int. Cl.
*C12Q 1/68* (2006.01)
*G01N 33/574* (2006.01)

(52) U.S. Cl.
USPC ............................................. 435/6; 435/7.23

(58) Field of Classification Search
None
See application file for complete search history.

(56) References Cited

U.S. PATENT DOCUMENTS

| | | | |
|---|---|---|---|
| 5,565,552 A | 10/1996 | Magda et al. | |
| 5,567,810 A | 10/1996 | Weis et al. | |
| 5,574,142 A | 11/1996 | Meyer, Jr. et al. | |
| 5,585,481 A | 12/1996 | Arnold, Jr. et al. | |
| 5,587,371 A | 12/1996 | Sessler et al. | |
| 5,597,696 A | 1/1997 | Linn et al. | |
| 5,744,305 A | 4/1998 | Fodor et al. | |
| 5,786,146 A * | 7/1998 | Herman et al. .................. | 435/6 |
| 5,837,832 A | 11/1998 | Chee et al. | |
| 5,958,773 A | 9/1999 | Monia et al. | |
| 6,265,171 B1 | 7/2001 | Herman et al. | |
| 6,331,393 B1 * | 12/2001 | Laird et al. ........................ | 435/6 |

FOREIGN PATENT DOCUMENTS

| | | |
|---|---|---|
| EP | 02004551.4 | 2/2002 |
| WO | WO 95/00669 | 1/1995 |
| WO | WO 95/15373 | 6/1995 |
| WO | WO 97/46705 | 12/1997 |
| WO | WO 99/28498 | 6/1999 |
| WO | WO 99/64626 | 12/1999 |
| WO | WO 00/52204 | 9/2000 |
| WO | WO 01/72781 | 10/2001 |
| WO | WO 01/77373 | 10/2001 |
| WO | WO 02/101357 | 12/2002 |
| WO | WO 03/072812 | 9/2003 |

OTHER PUBLICATIONS

Carninci et al., Genome, vol. 10, p. 1617-1630, 2000.*
Wayne et al., Human Molecule Genetic. vol. 10, p. 195-200, 2001.*
Sequence search result.*
Sequence search result, Jan. 2008.*
Belyavsky et al., "PCR-based cCNA library construction: general cDNA libraries at the level of a few cells," Nucleic Acids Research, 1989, pp. 2919-2932, vol. 17, No. 8.
Borsani et al., "EYA4, a novel vertebrate gene related to *Drosophila eyes absent*," Human Molecular Genetics, 1999, pp. 11-23, vol. 8, No. 1.
Eads et al., "CpG Island Hypermethylation in Human Colorectal Tumors Is Not Associated with DNA Methyltransferase Overexpression," Cancer Research, May 15, 1999, pp. 2302-2306, vol. 59.
Eads et al., "Epigenetic Patterns in the Progression of Esophageal Adenocarcinoma," Cancer Research, Apr. 15, 2001, pp. 3410-3418, vol. 6.
Feil et al., "Methylation analysis on individual chromosomes: improved protocol for bisulphite genomic sequencing," Nucleic Acids Research, 1994, pp. 695-696, vol. 22, No. 4.
Galfre et al., "Preparation of Monoclonal Antibodies: Strategies and Procedures," Methods in Enzymology, pp. 3-46, vol. 73.
Gonzalgo et al., "Identification and Characterization of Differentially Methylated Regions of Genomic DNA by Methylation-sensitive Arbitrarily Primed PCR," Cancer Research, Fev. 15, 1997, pp. 594-599, vol. 57.
Gonzalgo et al., Rapid quantitation of methylation differences at specific sites using methylation-sensitive single nucleotide primer extension (Ms-SNuPE), Nucleic Acids Research, 1997, pp. 2529-2531, vol. 25, No. 12.
Grigg et al., "Sequencing 5-Methylcytosine Residues in Genomic DNA," BioEssays, Jun. 1994, pp. 431-436, vol. 16, No. 6.

(Continued)

*Primary Examiner* — Lei Yao
(74) *Attorney, Agent, or Firm* — DLA Piper LLP (US)

(57) ABSTRACT

The invention provides methods and nucleic acids for detecting, differentiating or distinguishing between colon cell proliferative disorders as well as therapy thereof by analysis of the gene EYA4 and its promoter and regulatory sequences. The invention further provides novel nucleic acid sequences useful for the cell proliferative disorder specific analysis of said gene as well as methods, assays and kits thereof.

4 Claims, 10 Drawing Sheets

(56) References Cited

OTHER PUBLICATIONS

Gut et al, "DNA and Matrix Assisted Laser Desorption Ionization Mass Spectrometry," Molecular Biology: Current Innovations and Future Trends, 1995, pp. 147-157, Horizon Scientific Press, Wymondham, United Kingdom.

Gut et al., "A procedure for selection DNA alkylation and detection by mass spectrometry," Nucleic Acids Research, 1995, pp. 1367-1373, vol. 23, No. 8.

Heid et al., "Real Time Quantitative PCR," Genome Research, 1996, pp. 986-994, vol. 6.

Herman et al., "Methylation-specific PCR: A novel PCR assay for methylation status of CpG islands," Sep. 1996, pp. 9821-9826, vol. 93.

Hiltunen et al., "Hypermethylation of the *WT1* and calcitonin gene promoter regions at chromosome 11p in human colorectal cancer," British Journal of Cancer, 1997, pp. 1124-1130, vol. 76, No. 9.

Karas et al., "Laser Desorption Ionization of Proteins with Molecular Masses Exceeding 10 000 Daltons," Analytical Chemistry, Oct. 15, 1988, pp. 2299-2301, vol. 60, No. 20.

Koehler et al., "Continuous cultures of fused cells secreting antibody of predefined specificity," Nature, Aug. 7, 1975, 495-497, vol. 256.

Krug et al., "First-Strand cDNA Synthesis Primed with Oligo(dT)," Methods in Enzymology, 1987, pp. 316-325, vol. 152.

Martin at al., "Genomic sequencing indicates a correlation between DNA hypomethytation in the 5' region of the pS2 gene and its expression in human breast cancer cell lines," Gene, 1995, pp. 261-265, vol. 157.

Olek et al., "A modified and improved method for bisulphite based cytosine methylation analysis." Nucleic Acids Research, 1996, pp. 5064-5066, vol. 24, No. 24.

Olek et al., "The pre-implantation ontogeny of the H19 methylation imprint" Nature Genetics, Nov. 1997, pp. 275-276, vol. 17.

Rein et al., "Identifying 5-methylcytosine and related modifications in DNA genomes," Nucleic Acids Research, 1998, pp. 2255-2264, vol. 26, No. 10.

Sanger et al., "DNA sequencing with chain-terminating inhibitors," PNAS, Dec. 1977, pp. 5463-5467, vol. 74, No. 12.

Stites et al., "Clinical Laboratory Methods for Detection of Antigens and Antibodies," *Basic and Clinical Immunology*, 7$^{th}$ ed., 1991, pp. 217-262, Appleton & Lange, Norwalk, Conn.

Van Der Krol et al., "Modulation of Eukaryoric Gene Expression by Complementary RNA or DNA Sequences," BioTechniques, Nov.-Dec. 1988, pp. 958-976, vol. 6, No. 10.

Xiong et al., "COBRA: a sensitive and quantitative DNA methylation assay," Nucleic Acids Research, 1997, pp. 2532-2534, vol. 25, No. 12.

Yu et al., "Specific inhibition of PCR by Non-Extendable Oligonucleotides Using a 5' to 3' Exonuclease-Deficient DNA Polymerase," BioTechniques, Oct. 1997, pp. 714-720, vol. 23.

Żeschnigk et al., "Imprinted segments in the human genome: different DNA methylation pattersn in the Prader-Willi/Angelman syndrome region as determined by the genomic sequencing method," Human Molecular Genetics, 1997, pp. 387-395, vol. 6, No. 3.

Zeschnigk et al., "A single-tube PCR test for the diagnosis of Angelman and Prader-Willi syndrome based on allelic methylation differences at the SNRPN locus," European Journal of Human Genetics, Mar.-Apr. 1997, pp. 94-98, vol. 5, No. 2.

Zon, "Oligonucleotide Analogues as Potential Chemotherapeutic Agents," Pharmaceutical Research, Sep. 1988, pp. 539-549, vol. 5, No. 9.

\* cited by examiner

SEQUENCE LISTING

```
<160> NUMBER OF SEQ ID NOS: 15

<210> SEQ ID NO 1
<211> LENGTH: 29993
<212> TYPE: DNA
<213> ORGANISM: Homo Sapiens

<400> SEQUENCE: 1 ctggttttc  ccttaaggtt  gcttttaaat  gaaattaaaa  caaaaattat  gttttggatt      60
atgagctcct  agagcgcttt  gtttaatttg  acttatacaa  aatctaatgc  caagacagtg     120
ccatgcacgt  ttgaaaaata  aacaaatagt  aaatggtaac  tgcagaggca  tcccattcca     180
gaggagttgg  ttaagggaat  tgctaataag  tgaatcttat  atttccactg  atttacccta     240
taaagtctta  tattttttat  ctccccactc  ctcccaaaac  acatcccttt  tcagactgag     300
ttgaacatgt  acaaatattc  tgagagcctg  actcatgtca  tgcagggccc  actggtgttt     360
```

```
ttgaatcact tcaagaatct ggcagcaggt ctctgacttc aatttccccc atgtgtcttt    420
ctaggccctt tgcgtttctc ccactgttct actttccctc tcttcttcat tgtctgtact    480
gtattgcact actgggctaa tagatgctag ggaagggtaa tgagtaaccg gtacaatatt    540
tcaggaaagt gatttgcttt ttaattgtgc atttatgaat tgtttgcatt ttaccacaaa    600
taagatagta agtaaaacaa taaataatac atgaatttta aaaagacgcc tcaacttcag    660
agacttcaag tatattttag acaagaaaag caataattaa ataagcacag aatttaaaaa    720
gtaatacctc aaagtaaatt ggacacaaca ttttgttccg gttatgaaaa ggggaggctt    780
gaaaatatct cttggtgagc ctgagggaca tatggaatgt aattctttaa accaatgttt    840
ctcaaactgt atgtgagata attttaggtg gtacatgaga ataactttt atttctacaa     900 tataggttcc tttgcaagat catcttctat tcatggcggg ttttattagt tttccattta    960
tggtgactat aaaaaatgtc ctttatcaga taaacttatt taataaaaat agattattta   1020
aagatacata ttaagtcaat aatataggcg atatggctat aattataaaa gtgatattca   1080
atgtaaatgc tggaaataag gcctcattta agcaaacaat acattttgc ctttataacc    1140 ctaaaattct gtttcctatg ttaaacttat ttcaaatgtg tactgaaaat tgacgtttta   1200
tctgacacct agtggtgtcc atgttaatat atgtatattt aagacaacta ttagaaggta   1260
gtaatatgaa gtcaaataac taatatatta tcctggattt taaaaataat ttctgtacat   1320
gtattcttat ctagatgtac aaaaaactat gcaggagcaa agtgaccttg aaagcaaggt   1380
cagtgtaact gaaaaatctg actttagaag ggtacaaaga aacatgctaa gaaaacccac   1440
cctatattta tgttaacaat atgctaaagt atgaattttt attttattca aatcatacat   1500
ctcccacctt tatttgtagg tgaaactagc acataatgtt ttatgccaaa atgaaattca   1560
aaatgttgtt gccttttgag gacagtatta aattcatcat tgtacttaat ccttacatga   1620
tatttgctat agccacagaa cattcttaga cactatgatt cacaaaacat ttaaattgca   1680
tatttggctt gtaatatatt acatatttaa aagaattact atttttctga ataccattaa   1740
tactaataat agcatcacag tgactaagag tggacttaaa taaaggctgg cttgaaactc   1800
aggtctgcca tttattagca agcttctaaa aattctgagc ccttagtttt ctcacatgtg   1860
aaatggagaa ataaatctg caaaattaat taaatctgtc cattcatatt tttctctcca    1920
gtgtatatta actggcattc ctcgttaggc cagaatgtgc tctcaaccat gctccaaatc   1980
cgctttgtgc caaccccact gccagaaccc tttctacctt gagaaccaga aaggaaaca    2040 ttatgcctgg caatgcctac accctccaaa ataaatctgc aggaaagaac acccagtaag   2100
tgatgagagc agcaacgact gcctttatca ttttaaattt acaacaccac cttttctaga   2160
gcctcttaag cattgtagat aattccccac tcattaaaaa ataaattgta accataagta   2220
ttcagggttg atactgcttt tgaattagac agtgctcata tcagttgcat aagaccaacc   2280
taaagtagag gatgaaatct ttttctgaa cctttttcag aacgtaactt agtgaatata    2340
ttaaaactaa actttctttg aatgggagta atttctacgg attaatctgt aatctcttag   2400
accacaccta aggtaatgta gaggttgttg tatcataggc tttgtgatta gagaccactg   2460
gatttgtctt tggaaaagtc actcatgatt ctttgggctt tggtttcctc atctttata    2520 ccggcttaat aatgaccacc gtagagttgt catggaagtt aaatgaactc atgtaccata   2580
agtgaccaat acaatgattg acactcagtg atttatcaat aaattaaaac atttattatc   2640
aatatgacag agaaggtgcc gctaaaatag acaataggtt tttggaagag gtgattaaat   2700
ggatgcaaaa tttatggatt gtttattccg tctacctttg ctgtgtcccc tggttgtggc   2760
```

```
atacacacgt gtgggtataa aatcgtaaat cctatgtagt cgcgtagtgc atgcgcagaa      2820
ggcttagaca cgaaatgtca tttcagcaat gtgcctagag aagctctgac gccgccttgg      2880
aagtaagtcg ttgctgcctg acctttgggc gtctgggacg gatgcctata cctgcaccca      2940
gcagcactgg aaggggccca gcccttcgc agcacagcct atccccagac cgcttagtcc       3000
ttcataacat atatctccac ggaaaagggt atttcctccc gtcagaaaaa gcgccccagt      3060
ctggtctggg ttggtttta tttcacgttg ttgcaagtag gcgaagtccc ttctgtctcc       3120
tcccttgggg taagtggaaa ggagtccggc aggggcccg cagtggcctg cacaggggaa       3180
ctgggtagcg agagagttcc aggcaattcc ggggctgcc ccacagaagc aggtggggat       3240
cgacagtggc tctccggccc agggaggaga gcgcggtcgc gggtccctcc cctcagcctg      3300
gaggctgcag ccgctcgagt cggcccgggt ggggcgggg tggggcggc gcggagggca       3360 cggagattac ggcggcgcca cccgggacat ccagggcccc gaggccctgg gcggtcccca      3420
cgcgagatcg caaaccatga caataggcag tcacccgagg tcaaataaaa acggagtggg      3480 tccccgcgc gccgccgccc cccgcgtccc tggcggcctc ccccgaggcc cccggcggcc      3540
tcacgagccc gcagtagccg gtggcgacgt cgccccgcc ccacctccct gcgcaagtgc       3600
gaggctgccg gcagcgcggc gcacgctccg gccgttcccg gcttcgcgc aaaacttcca       3660 tcctgtccac gtgaagttgt cgctgcctta gagaggggga aagagctgcg ggaaaagccg      3720
gggagtgacg actgcggcgg ctgggcgcgc tctctcattt tcttttcttc tcctttcccc      3780
cctgtcgcag tccggagttt tggctcctct ccttttcctcc tccccctcgg agccggcttc     3840
tccctccgcc ccgcttctcc cccgcttgtg tacgctattt gttgtggggt ggccgaaggg      3900
gatgtcctgt tttcaccaga ggcacagcgc gaagggaaa cttcgacact ggaaggaacg       3960
agaataaata cttaattacg gacgcactga accgcggctg ggacagacac ttcgggaacc      4020
cgaggcggac cgggcgacga ggtgagtgac cccttcttcc aaccccgcc ccagggctcc       4080 cggggagcc tgagttgaga gaaccccaa actttccggg aaagtgcgcg aggctccgcc        4140
ggggacgccg agcgctgggt actgaggacg cgcagctgga cggtgcgtgg gcgcctgcgt      4200 ccccggggg cgcttggagg ccgggtgccc cacgcctgag ggcccgggcc gctcggaccg       4260
cagcggtgct ctctgcccta gaagacgtcc ccaagcccca agggtccctt ccgagcctgc      4320
ctgtcccttc cggggtcggc gcggagcctg cgcgtaacgg agttcatcca gcagtccagc      4380
gcgcggcttc tacctgcacc ccgcctccac ctggcagagg gcgcgagcatc ggggtctccc     4440 ccacatctttt cttatgacgt gtattacttt ctgatgaccc cctagatggt ccaggcgcga     4500
ggatgctgac ccagagtcct tcggagggtc acaggcgcct gggctttccc ggtgccgggt     4560
gcgtgtgtac tttaaaggct cgcgttctaa tctccaggca ctgatcgggc ttttcaactg     4620
cggcgatccc actttaatag ttttttatgtg gcgtggactg aatgtctcct gcagtttgcc    4680
agggtcggtg aaattagagg cgccttgtca gagcagtcgc gttcattggc tcgagtagcg     4740
ggtgccatgg aaggcttata acttctccaa aggaagggac ctggctgggt agagcaggtt    4800
tttctctcct tccaagcctg ctgggtctgg ggaggcagtg gaacttgaaa tggctcggat    4860
ttttagcgtg gtgaagcgag gtttggaagt agacgtgtgt gtgcttgttt tattctgcgc    4920
cgcacagcaa cccgaacttt cgtttggtag cacttgaaag agttttctcc ctttgtttgc    4980
gagattctga acagctcgga gcgattaggg aatttgcgga ccgagtccgg tggcagagct    5040
ggggcgaaag cagagagcgc aatttaattt ttgtcatctc ttccctgctt gggaggatag    5100
tgtttccctt caccaccacc cctctttctc cttcctatga agacaacgga tttgcgcctg    5160
```

```
gggtgagagt gtgtgcggga gagtggtgtg gagactgtcc tctctcaccg cgtctcctgc    5220
gcctctcccc gccatcccga gcgggcctag agagtcattc atgaatctta acctgagggc    5280
aggggaggaa ggtgcaggtc cctctgccct ttctgccaag gtgcagaata gcgcccgggc    5340
gtgtgttttg gttccagagc agttccacgt ggagcaactt cgtgtgtgtg tgtgtgtgtg    5400
tgtgtgtgtg ttgtgtactt gatctgtgag gaggtaacag gactctggtg ttcaaaccca    5460
gtgggccgtt ggccattagt ttgctttcct ggctgtcatt acagacactt ccaaaatctg    5520
atacctaaga gaaccaacag gttaggtttc acattaaggg ctcatactta acagttttct    5580
ttctccctta ccccttttgg cttggcaccc tgggatcaac gtaattgttg gagcgaaata    5640
cacctcctgg aatatggcat tttgttcctc ttctcatctg tggccacttt gtgaaccctc    5700
gggtgtttgt cagtttcagt gcgggctcct gcgggattta ggtgggagtc ttaggagcgt    5760
ttaacaaccg cgggctcccc atcagcagct tctgaagttt cacttacacg taggtgactg    5820
acaggattga aagttgacga tggtttttt gtttgttgcg ttgttttttgt ttttaaaacc    5880 ttagggaagg gattgtactt gaattccttt cccgggtacg gtttggttttt aagcagaatc    5940 agtgcctttt tttttttttt tgtcttttaa aatattattg gcaagcttaa acctgaagaa    6000
ccaaaaacta gaggggggtgg ggagagaatc cccccaaaaa atatttgata cgtgatacgg    6060
agcgttttag gagactgcat tcaaagacat ttgtgtattt ttaaaaataa cattatccca    6120
agaaacaaaa agcagtagta acaagagaca gattgttttg tgtggagcaa gactgccaga    6180
atctgatttt tatggcaaca atatcgaaag cagacataac tacacccaca tttattgtta    6240
taaaccgtaa aaatagtttg ttccacctga ttaaaagttg taagtcattc aaagttaaac    6300
ccgtatttag gaatgactgt acaagaatgt taaaacctt gacagctaca gctttgaaag    6360
caacataatt agatttgttg aaaatgtctc ctttctctga ttattagtga tatgtacttg    6420
tctttcataa taagtaaagg tctacaatca atatggtttt caaaagcctg ttttcctttg    6480
taaatttcct gaaaatagta tgtttcaata tttaaagacc attgtaacta ccggttggtt    6540
cacaattata actaaaataa gatttactca gttgttttct ttttattagt atttgttgaa    6600
tatttgaaat tgaatttctc atttccaaaa taaaacgtct cacatatatg tatgtactca    6660
caattaacac ttctttttaag tagtaggctt aagttttaaa attttttaaaa tcttaagatt    6720 tgtataaaaa ggagtgattg tataaaaagg aataataatt attaattgtt aagaaaaata    6780
gatgctgaat tcagagggt ttctagaagc tggagaaaaa aattgcatag aagtttcttt    6840
tttgacgggt gactggcaga tgagttactt gtcatttttgc tataatttat ttttttcttt    6900
taataaggct cttgggtta aaaaaaaaaa aggaaaaaca agtactccat ttctaagagt    6960
ttccttttta tttatgttgt actttggggt gtaaataaat tttacatagc cacgggaaat    7020
agagtatcca atttcatgtt ttcagtctct gttgcaagct ctaaatgact gatgtcgtgt    7080
ctaaaaatat atttatatgg cttgatattt cattttaaca ttttatgcac tggaattaga    7140
ttttttagga tttttagaaa gatagaatga cagaaagacg atgactattg ttataaaaag    7200
ttagaatgtt aggaagttca cattctaact ttcaaataat caaacttatt ttgccccaca    7260
aaaactcaca gttttatac agatttcaag aagagggtg ataatctttt tcactactta    7320
gttaagtgtt aagtaattta agaatgcaag tatgtattat gctttctcat tatcattttt    7380
ttctgttagg taaatgcaag aacactggac attctgtaaa aacaggcccc tctttataag    7440
gagtttattc accatagttc tgtattgcag ctgctgatca tatttcatgg agctgttaaa    7500
gcacttaaaa cctaaaatta ggtactgtct ggttgtaaat atttcagatc acttatttaa    7560
```

```
gaaataaata gaaaagtgtg ctatcaaaag taggagacgt tttgaatcct ctcattgaag    7620
agctgaacaa acctctatca aaacaccttc ttcttttttc agtgagaata taatcttgac    7680
agtttctttt tctaaatgga tattattctt acatgtacta aatgctaaac tcttataacg    7740
tgcctccctg tagagtatct taaactaatt atattcagaa atacagttgg gggatttttat   7800 tacaatggtt actaggtgaa ggaaatcaac accaggggaa tggggtggca ttgcagtgta    7860
cctgcttctc tcatgaattt ttcctgctaa actaagaaat gacatgctgt ttcaggcatt    7920
tgccctggag atgggtgaga tgcaatatgt gtaatgctgc atcttatagt tagatgtgtt    7980
ttaatgaagg ggacactgca tagtcattaa atcattttttg gagccaaact tggcgtcatt    8040
tagcttgaac ttaagtggaa gaaatgaac aagagttaca cattcaaaag aagtacaagc     8100
aactttgatt gcttttaaga ggtttgaaga ctttgtaaac attactgtca ctcaatattg    8160
cttgtggagc tgtacattaa tatatgcttt ggtgatatgt cattttacgc ttgaaatttg    8220
tcattcttag tgtttctcca tccatctttt tattagtaaa gagatactga aaatgaacac    8280
tactattctt actcccctaa ccccttttcac acctccagaa aaagagatga aactgattaa    8340
tttaaaatag aaaccatttt gtgttatcaa aaccacattt atatagtgat ttgagacagt    8400
ttcagagagt gcacctctga gtctcactgt aacctttttt gtcattgaaa ggtgctaatt    8460
gatcttaggg tactgacaca atagtatagt ttgatatttg aaacctttca gagttggtct    8520 ggccctttttc ttaccctgag atttcagtgc atggatgatg aagaaagaca ccattctaaa   8580
ataccagaaa ttctcatttt tttccaatat gaaatgtttt aatacagtat gttcatattt    8640 ttaaagctttt tatttacata cagtaagtaa atttatttta acgtacttttt ggacagtagg  8700 agaaagacct atatgttcta tcgtgttaga attttttagt tttttttttt ctgcacaggt    8760 agtttatttta ggttataatt tttaggcaaa gtctgattcc tattatcaca tgaatatttt   8820
caaagtgaaa ttgcgttaaa ccaatgtgga atagcttttg tatcaccaag gcatatatta   8880
atgtagatgt caaatatgag agcatatttt cttgagtata tttatatcct aaagtgtatt   8940
tttaaataaa agtggtcact gtagtcttta gataattaca atttggctgt cattattact   9000
ataatattaa tcactatcac catcataaca tcatagctag catttactca ggaatttcgt   9060
gcaaaacact gttttaagca tttatatgga ttagctaatt ttaatcttct taactatgcc    9120
gtaaattagg tacttttgtt attcctatttt tacagataag gaagctgaga cccagtcatg   9180
cagcacagtg gagccaggat cctaactccc cagtatgagg ccagcaccct tatccttaag   9240
cgtgtgctgg gctcttgctt ccatcagtca tataccacca ttttttaggtg gtacctgaac   9300 attttgtttt aataatactt atattttatg taaggataac tagatattag aaaaatttgt    9360
taaattttgt attaaacctg taacttcatg ggcaatattg tttgagacaa gaccaaacaa    9420
agtattgaag tcaaagaaaa aaaattaagt atctgaagaa acgtattaag taacagtgaa    9480
caagaatatg gcctaaataa ccacagtcat gaaggctgga cagcaaatga ctgaatttgg    9540
agaaatgctg tattttgtaa tgtttcccaa ttatcaagaa cttatgacca gatctttttaa   9600 atatttaact aacatgtgga atcttccttt gctcttcaag ccttatccaa attggttaaa    9660
tgttatcaac tttgtatttt ctttgttttt gttttttgtt gtttttaatgc tggttttgaa   9720 tctcaaatct gcacatttat gttgaaccaa ctaataaggc ttgaagagtt aaagagtgca    9780
tgatggactt ctggaggcag gtttaaatta taatggagct gcccatattt tggaaataca    9840
ttcaatttat ctggttatcg catgtgtaag gttttctgta ggtaaatact tttgctgtta    9900
ataacctgtt ttacaatttt atagtatttt tccactgaag cagtggtttt cattttttta   9960
```

```
tttacttata tactcagcca cggatccttt catttaaatg gaaactgatg atatgcccag    10020
tagagaaatg tgccactgct ctaggtgaag caggatgtag gtagcctgag aatgactcac    10080
caacagtacc ctctcacggt ggccgccgcc tctggagttc tctctaagtg tcttcaatgt    10140
atggaaactg ctgcaaaaaa attcaagtct tctgacaaaa ggggttaatt cagagtacct    10200
gccctaacat gttcatgtgg catcactaaa aaacagactg tcagatacgg taaaatatct    10260
cccagtgtga catatcagca gaaaggtgtg tctactctcc cttctataac ttgagtatcc    10320
gtattaacca gtcttcaaat tcgatttagc actgagaaaa ttaaaactga tcaaaatgtt    10380
ccctgtgtgt agttacaggt ctgaatgagg cacaaaggac ttgtacctgc aaaggttgac    10440
tttattaatt agaacatctt tcctccttta aagactgtaa gaagaaacac cagcagtggc    10500
ctaacttgac atgactttag attttcacgt aaattattgc tactatttct gttatccttt    10560 cccccttct ttttaaaatg aaagggacat tcttgtgaa agactacaat taaatcataa    10620
aaatttacat tcatgtgcca ttaagtttaa ttctactcac aaaagcaaca gtacagagtt    10680
tgaaattcta tccctaatca agtaggtgta ccacataccg ggagggctca ttatgcacaa    10740
ggtcatatat acaattcaca gacctctgca tatacccaac ggagtgatct attcattaca    10800
tttcacctct gactttgaac tccctaatgt taaaagattt gaaagaacc gaatgttctg    10860 attaagagat tgaatatttc taacttaatg ttttcagtat gttgaaagtg atgatgactt    10920
gggggaatca gcagatctct acattaccta attcttttct cttacatttg aatgcaaatg    10980
tatattcatg tgcggttatg actcaagtca ttccttgctaa atttaatgac gttgtaggtg    11040
aatcacattc agatttcctt ttgcaggttt tccagtaatc taaaacaatg cttctagtag    11100
gtaacttaag catgcaaacc tcaataaacc tgtcaagaac ggcaattcta ctgttttatt    11160
ttgttttttt ttttgtttgt tgttttttgc attaacttta gttgataaga tgatggtact    11220 gttattttc ttagttgact catgaagaat tttaatttag gtctagtttt ttcccttaat    11280
tgttgacttt agtttttaaa ggtttcgttc atgaaaatgg ttagcaaagt tgtgggtact    11340
tggtaaatgc ttgttaaatg cttttttcctt atcagtgttg ctgaagactt gcaaaattag    11400
agtgggatgg atagatttct tttctactct gcatggcttt gaagactttg gagcttttat    11460
tgtattctta tattttaca taccattccc aggaatattt agagagagaa tcattgtaac    11520
caaggtcaca ggtctaatcc tcaggtattc aaattagctt taggtggaca attgtcctat    11580
acacacttgt tcgtattaat gttgtcataa caaatatagt tataatatct tgatgcctct    11640
cctgggggcc cattctggac tgtgttgaag ctgtctctaa cactctctca cgtccctaag    11700
atattcaacc acatttgttc atgattttta tgaggtccct cctggactta aaattcctta    11760
aaaaatttgc ctgctgccta tagggcaaat tccaaaattc tctgcaggga agataaccct    11820
tcatactgag aaccttgctc aggttgctct tctcatctct cactccccac tcacaacaac    11880
tctcttttcc agctgtatgg aaaactgcag ttctcaaata caccttggac atttccactt    11940
catttctttg tgcgtggaat gcttttctc tggaaaacat cgcccctctc cccctgcaaa    12000
tatcttttct actgcttttt caatacttaa ggtgcaaaat gttagctcct ctgataagtt    12060
cctctgacct ccagagtctg agttgaacgt ttctttcttg ttactcccaa agcatccagc    12120
ttctacattt aacatagccc ttgccacatt gaaatgtaat agattacatt agtctaaatc    12180
ctgctttaag ctgagaattt actggaagga ttagctgtat ttgtcatttc tgtatcgcta    12240
atgcacagtg cactgctgga catatagtca gtaggtagtt gttatattcc cattgaatga    12300
atgagtagag gtactgggaa tgagagcaga gattgtgaca ctgaacatcc cctccttgag    12360
```

```
actgggaaca gtgagaaggg cagtgactat tacaaggtgg gactacctca ataacaacct   12420
cagggagttt tggtataaac ccagtagaat tgcagctgtg aatccaggct taggttatat   12480
gtatgtatac gtgaatgtag aaatgtgttt atttcttacc actgggaagt cagtgatctg   12540
gtggataagc caaggatcct gaaaatctct ggagatacgg taatttcata gtacttgaaa   12600
tctgagagac tcagttctta tagcacagtg agtaagtaga aagaatatgg gggctgggcg   12660
cggtggctca cacttgtaat cccagcactt tgggaggccg aggcggatgg atcacctgaa   12720
gtcaggagtt cgagaccagc ctgaccaaaa tggcaaaacc ccgtctctac taaaaataca   12780
aaaattagct gggcgtggtg gtgggcgcct gtaatcccag ctactcggga ggctgaggca   12840
ggagaatcac ttgaacccag aaggcagagg ttgcagtgag ctgagattgc accattgcac   12900
tccagcctgg acaacagagt gagactccat ctcaaaaata aataaataaa taaaaaggaa   12960
gaagaatatg gagccaggca cttgggttca gacctcagct ctaacattga tgagtttgta   13020
acatcaaaca cattactgaa acagattttg cttcagtttc tcatgtgtaa cagaacatgc   13080 ctcatgggt tctgatgaga attcaatgag taaatatatg taaatatatt tagagtagtg   13140
cttgatatga gtatcagttg ttattactat gattgggtat cttttcattag attaccccca   13200 aatgttccag agatatttag agctgaaggt cttttttggg gggctatgga ttggtgacca   13260
taaatggagt gtccagtagt ccaagtataa attagatact gtgggtcatc ttggcaaatc   13320
tgaggttgta tttggagcct taagagaaga cactataggt gctcaacagt tggcattggc   13380
catttacgtt gtgcagtaat atttctttta gtaaatattt ccgcatacag taatctagat   13440
tgttttagag ctttaatctg tgtggttcct taactacttt aagcaattat aagcacgttg   13500
tataatggta gtactttata gccaatattt aagtttcctc agttgctttt ttttcagccg   13560
taaggtacca attatgagaa tttgtataat tttcaatagt cagtgggcct gatgaactca   13620
atgtaaactt tttaaaaggt agctttacat attgctatga ttcttacctt tagagagaca   13680
gtaggaggta attagtacct ctacttacag aatttatcac ttggattcag atataatggc   13740
tatgtggcag gatggggctg aaggaaaaag gaaagttaaa atattaattg tcaaggtctc   13800 attttttacag cttgtctgga actgctacca ggtgtatctg tatagtttta aaaatgataa   13860
cgttgtacct gaattcttca gtatatttaa ataagagttt ttcaagctct ggttattgac   13920
attttgggct ggataatttta ttcaggggat actgtcctgt gcctggtagg atgcttagtg   13980
gcatcgctgg atgccaggga ccctccctcc cctggtaatg atggtgtctc cagacattgt   14040
caggtgatct ctgggagcaa aattgcctct tcttgagaac ccataaccta agcagatctt   14100
aatatcattt gatatagtca aaaaactccc agggctctgc ataagaggat tgttctattt   14160
ccagtcaagt gtggagaatc ctaatacctt cctcccaagt ttaaacatga agtcaaacaa   14220
ttctcattag tctgtgttga tagattaact ttgcacagag gggatttaca gatacgcttc   14280
acacagattg accatctcca gcatattttc cttttctgga aataatatat gagtgggagt   14340
aacagaatac ctgagagaga gtatgtagga agtaaatatt tatttgaatc atctatgtgt   14400
cttttcttcc ggttatttgt cagtagatag tttggattta tttttaaata atgaccattg   14460
cctttccatt tctgtgggta aatattcagt aataagaaac tttttatttta tttagtctgt   14520 agtgttagaa aaggtaaagt tactgataat cacaactgct gaagattaaa atacttagtg   14580
agttaaatta tttgtttgta atgagaaatt ttcaaaagaa ttatgtgtag ctttcagttg   14640
taaccacaag ttcaagatct tgagttaata acatttgtac agctagaaga aagtaaaaat   14700
aaatatatta catgtaaaaa ctctcttttg tgaattctca gatccaaact tttaagttct   14760
```

```
cattctatgg gtttgatgtt gaccaataca ttttatctat gaaatgatat ataattgatg    14820
taagtaaatt tgactgttgt ttgggcacca cccttacata atttaagcat atatgaaaca    14880
catttcaaaa atcacttgaa caaaatggga acaataatgt tcacataaag tgagagagga    14940
taacttttcc catatgagtt ttgggttgaa tttcaaaatt attctgaaat atgaaacatt    15000
aatattataa atatatgatt agactaattt tcttaagagt tctaaacagt agataatttt    15060
tatcttatta gaaattgcaa agatacttga aattccacac ttatgcattg tctaatttag    15120
tggttgtact ttaattgtat taggtagata atcatggaag cagtcagact aacctggaga    15180
tttcacatca tttactaatt gatgcctaag taggcagggt agaggtactt gaaaacacac    15240
acacacacac acacacacac acacacacac acacacacac actcactctc tctctctcac    15300
ttcctttgat ttgtgcttta attttgaaat gtgtgcttag gtggcaaagg gctgcaaata    15360
cagcatactg tgtttgacca aaatatttt ctgtttccta ggtggagaag gaccctgcat    15420
agctccttgt tagcagagag ataaagtggg tgctgggcaa cccaatgaca ggtggaggcc    15480
gttctcgggg agtgttgcgg agaatttgag acagggtttt aaatcacaga tagtggagga    15540
gagttctgct tcattcatgg acaggaagtc caaagaaggc acagcgaacc acaggtccat    15600
ccaggcactt tatgccagat attgaacggg aagcctagta gccctttagt tactggagaa    15660
cggccaaaaa cccagaggtt ctattttcc aaatgagcac ttcctgggtt cataaatcaa    15720
ggaaccccac agagtattca agtcacatat ctcctttctc aggttgattc tttgtatagt    15780
gggtcctaat gtggtaagac ttacttatga acattttatt tcttataatg ccgtcagtca    15840
cttccttttt tctccctggc atattctcac cacccttatc ctccatggcc ccaactccct    15900
taacctactt gcctagtgct cttttgctgc ctacctggac aaaataataa taataataat    15960
aatctactca tctttcaagg cttagctcaa atgtcacctc ctctgtgaag ccttccttaa    16020
ggctcaggca gaattagttc ttttctctgt gtaataccat agcactttt ttggactgtt    16080 aatataacag cagattgtgt tggggctcat tgtatgtgtc tgtcttctag agagactatg    16140
aactcacaga ggggagagat catatctttt tccctccgta acctcaacac ctggagatgt    16200
taatggaaat taagtgactg cactattcca tgcatatctt taaagggcat taggtcccaa    16260
accagacatc tgcaaaggat gaatcctgtt aacttttgg aaaactggtt ctcttttgct    16320
tgtggtcatg aaagctggtt tattggttat tttctactcc aacttattta agcctcatt    16380 tgtaccaaag tattactgat tttctagtgg aaaaacaggt atgtccggcg tacattggta    16440
ttttcaataa actgacattt aaaagacaga tttctcgttg aggttatgg tcttcataat    16500 tctagttttc tccagaaaca gaccttgatc tctttggttg ccttctgcta agatcgattt    16560
catgttattt tgaagaattt ttaaccctca gaattataga tttcatttga gagaaagcat    16620
gttctgtatt tgtttgtgtc agtgtttcaa aatgtgagga ccaaaaatcc cagatgtatc    16680
tattaaaaat atacgtggcc ttttgctgag ggaaattaca tcttttttt caggcacaat    16740 tgaggaagta aaaaaatttt gtttagtttt tagtggtttg ttttaggca ttttccatac    16800 aaagatgagc aagacccttc aaaaaccacc aatttgctta tttagggggg aaagtcttcc    16860
tatgtccaga aataacatta aattaagatt attgtttcca atagtttcaa aaattgtggt    16920 tttatttct tgtatgagtc attttttagc atagtgcagt acatgattgc actacatcat    16980
gacaaagcat atttgctctg tgtttcagtg ggtcacttta tttatcagcg tcagatgatc    17040
agatcagaag agagatctag cctaacccct ccatttgca gatgagatgt tgtattatgt    17100
gaccttaaga ccttaagtca tttactcaga acaaaacaga aaaagagaac ttcatgctgg    17160
```

```
ggacacttca tgctcccaac tctacatctt accactttat ttttatttgt ttgtttctga    17220
tgaggagttg agaatgctgg aatcagacta cctttgtgtg tatccaggct ctgccactca    17280
tcagcgatgt gactttggtc atgtaatttt ctgagtggct gtaagccata gttccagcat    17340
gtgtacatgg ggaataataa cagtactcgc ctcatggagt tgtaaggaat aattgaattc    17400
atgcaggaaa gacatttggt tcagtgcctg gcccactata aaagctcagg ttatagtttg    17460
aattgatatc ttggaataaa atgctgagtg tatttgatat tcagagaagg aaattcatgc    17520
tgctaaagca agttttttt tttaatctgt tacttaaaaa atacaaataa gtcatacttt    17580
gtataacata ttaaaacaga gatgatagag gttacttttg agaggaatga ccagagggag    17640
caagagagag gctttggaat gctgattatg tcttttatct tggtttggtt gctggtcatg    17700
tgaaagtgtt tattcaataa aaattcatca gtgatcaact tttgatttat gtattttatt    17760
ttactgtgca tatgttatac tttcttaaaa agttttaaaa atacggatat atttaaagta    17820
aaaagtggat ttactcattc ttattctctg caaatcagga taagttgtta tacttagatg    17880
tgcatctttt caggcatttt ttttttctata tatgtgtaaa tgtaataact atgtgaggat    17940
gtaatttatt ttcatttttac atttttaact ccaataggat cattgatttc cttaaaactt    18000
gcttttgatc tgctgaatct tgaatatttt tccacatcag tacatatagt tttgggtgct    18060
tctatttaat gtatgcagat atttcataat ttcactgttc ccctcttggt gtatgtttac    18120
attgcttcca tatttttact attactaagt atgttgcact gatgatttt atgtctcttc    18180 gtacatctgc caaaaatatc tgtagataaa actctagatg caatattaat agataaatat    18240
gtatgtgcat tttccataga aaataccaaa atgctttta aaaagattta tgaatcttgc    18300
atctttaagg taatattctc atctttctca caaaaaccag gtgcaaaaat ttcaacttaa    18360
ttgaaccttg taattatttg tgctctggtt aagaaaatg gttatagtag taaattcctt    18420
gaaactcata tagtaatcgg aatactccac tatgattagg ataaataatt ctattaacga    18480
tatatattta atatatacat ataatttata taattagttt ctcacttaag aatatttagt    18540
attcattttt atgaatgcat attatattta cttatggttc gtaagcccaa atgttaggaa    18600
gaaataaatc agtaatatta tattcactac attttttttt acttagtacc atcaaatatt    18660
taccagaatt attaggagaa atggttctaa ctctcatgtg attggtgaga acttatgagg    18720
aatgatatat tgttattcta gtaagagcct actctgtgcc aggcacagtt ctaagcacct    18780
tacatatatt acgatagctt tttaacatag agatgaaagg tatagacatt gtataagtaa    18840
taaatgacat tactccatta taaatgtgtt gataaatatt attatacatg tcacaatatc    18900
agttgtgtca tatcaatgac taatttataa atctgttact tattataatc tgtttaatgt    18960
ggaaataaaa gttaatgcat caaaatccag aaaaattgcta ctcaaatgct ggctaaagta    19020
atctgataga tacagtttta aaatgaagta tattaatcag ttgatttgt tgttcgattt    19080 ttatatgtag aaaattctgt ctccagaata ttcgttctt gtagttttg gttaagattt    19140 tgattaatct tcaatggtta tctagtgcct ttaaaagta gtccaactca gaatagctaa    19200
tgtattcctc ttgcattgaa taaatatggc tatcaatttt tgtggggttt ttttcctgc    19260 agaatttcct gttattctaa gggattcaat aggacttaca catataaaac tgaaaattat    19320
attactatgg ggaagctgct ttgtgccttt cagaaggaac tctcttgcta acttaagtac    19380
tgtatgtgtg tagaatagct aatatttcc tcccaagaaa tttcatgtat gcagttaaaa    19440
cactcttaaa ttgattaagg attttgttata tatttccaga agcactcaag agtacttta    19500 tggttataag agtagagtgc attagaatgc cagaaaccaa tgaatacgct agaggccttc    19560
```

```
aaaactgtgc ccaacattcc tgactttacc atataaacat gtggggtagc ctggaaaaac   19620
aaaacaactc tccttcccccc aacgtaggtg aggcctgtga tgataacact tcaactggct   19680
tgaatattaa tttgatactt ttctgttaga agtaattttt attacttagc aaatgaaatg   19740
gagaggtaat aaatatgact gatatttatt tcttgagtaa agtattattt tacatcagat   19800
tcgaccagtt acctttatcc tttttggaaa atgtattata caaactacca cagtattttg   19860
cctattaatc agggaagcta aaaaacgttt tataaacgtt gaatcaaaac tctcactgct   19920
gtgagggaat taaatttcaa gcaatatact cctttttatag ggtgagaaac tgaagtatgg   19980
agaaattaca aggttttccc aaagctatac actgagtcat ggcagacata gaaatctaca   20040
attctgtttg cctgattcaa tctgaaactt catgaaacgt aatttatcca tttcctgaca   20100
tgtgctttag aagtatatttt ccttatttgc ttatttatgc tctcattcat tcattcatgc   20160
atgcatttat gcactattga ctatttatgc actcattcac tcattcatgc attttaaaag   20220
aatcggtgtt tttgtatgat acagtcttga tttagggact atgaatattc tgaatttata   20280
tatcttagat atttcttcaa agaaactcat tgcattttt tcacgatcat gaaaaagaaa   20340
ttaagacatt aagaaaacca agctggattg tccaagtgtg ggccatagca gtgtctatgg   20400
gcagcacctg aagctaattc aggagtgaat ctagtttgtt caagtgcttg aacaagaact   20460
tggctgaagc cctggaggag atgcctgggg catagagtgg ggacgaggaa aaaccatagc   20520
actcttagag agtactgtaa ggactagtat ccacatctct accacctgat gtctttacat   20580
ttggttcagt caagagagag ggggcaaatt attctgcttc tcattctgcc atcttcctga   20640
tttcagttct cacgctttaa attctttttt attgcgatct ttttcttact agtttaacca   20700
gtattttccc gcgcttttctt caccaaattc gtttctttcc atcagcttgc ggagttatat   20760
tttttgatcg aactgctggg gttacaagta atttgaaatg aggaaagtgt ctagcaactt   20820
ccctcagtcc agtaccctgt aacagagact tcagagtacg tagtgatgac acctgccctc   20880 ctcccccttct atagagagtt tagtgggcaa cttttttggc ttgttctctt gttcttttct   20940
tgcagcccca agactaggga ctcagacttg gtttctgctt gtatggctct ccatctcttc   21000
ccttggaaga gttcttcccc gggggctttt taggtccaag agcatttgga cccctgggag   21060
atgaacttgt agattctaca aagaacatcc aagtaccagg caaaccacat cttcctgtag   21120
cttaaacgtt agtctttttt ccccccttcaa ttttactgaa gaataattta gtctccaaca   21180
aacaagcaaa cagaaccccta gggtctttct caaaggtgca ttcttgctgc tttgaagatt   21240
atcatcatta atttctattt cagctaattg gttttccttt acatttttat ttgggtataa   21300
atgtgatact ttggtataca ttaatgttga tctatattaa tacgtcaatt tataattgag   21360
tgatttaaaa ataatgatgc actatgacct agtttatatc tgccttccac ttaatgcatt   21420
tcctaagcaa ttatgctttt gtggctgact gaattccctt ataattccct gttgggaaac   21480
aaagattttt tttaaattg aagaagtggt cttgttaacc aggggcaccg tacttaactt   21540
gagagaaaaa gattaggaat gacaggaatg acagcatact cctaatatct aacagcctgc   21600
catacatgtg aaagcaggac acatagcagg gaagcataac gttgagttga ctcaaaacac   21660
caaatgtatt tgatacatta ttttctgaat tcttacaact tcagccctttt taaaggtctt   21720 tggatttta gaagctataa gggcagtttt tggtaaaggt ggccctactt ctaattcagt   21780
tacagagtca gtggaatgat ttttatattc aaatgctaca ggggaattta ttgagaggaa   21840
aaagggtact caaactttcc tggatgcctc aattaaaaat ctggatcaat aaaatttcct   21900
caagtgtccc aaatttaagg aaagcaaaca gcatcttatt taattacatt cttaattagt   21960
```

```
attcactata gacacaattc aaatcagtaa cttggcatta gatgaatcag atttattgcc   22020
atattatata actctcatgt ttactttgtt gtgtttggga cttctccctc cccataataa   22080
agaatatgac tcacaggtgt cacaccttga ttcctgagaa attaatgtta tagaaaagtt   22140
gtttggaaag atataattgt gattttgtta ttgttttgt tgtcattatt ttcttttatg    22200
gggatgggca cacacttctt gagatttacc agatttacct tgtagttcat aaattatttc   22260
tttagatgta tctaatttgc tgtttagttt gtttcttgta aaaaaattca gtgaatatat   22320
ttttaaaaac attttatgg ttctcttcca ggtttgtgtg tatatttttt tcgtgtgtgg    22380
cttttcaatt ttatttctgt ttcttttgtg tctgttttaa gtatacctat ctagtttttt   22440
ccacattgct ctgtagtttc acattcttag attcctaatt tgttgttgtg gctactctct   22500
actgtgtttt gtttctttat gtagcttata attttttttt tcttttgag atggagttgt    22560 gctctgttgc ccaggctgga gtgcagtggc acgatcttgg cttactgcaa tctctgcctc   22620
ctgggttcag gcgattctcc tgcctcagcc tcccgaatag ctgggatcac aggtgcccac   22680
caccatgccc agctaacttt tgtatttta gtagaaaagg ggtttcgcca tgttagccag    22740
gctggcctca aactcctgac ctcaagtgat ctgcctgcct gagcctccca atgtgctggg   22800
attacaggca tgagccaccg cacctcgcct gtagtttata acttttggtg gatttctctc   22860 ttagaacccct ttgtactctg tggagcaatt ttgcattccc ctggagtcta gggatttcaa  22920
acctctaggt cagtctttat tttattttat tttttgtct tgaggtttcc ataccacaga    22980
tgcagtaaac atttagaatt tacatcctgc aaggctgaag ttttgattta tctcactcaa   23040
gaaattattt tcttttattc tcttcccaaa ggctccatca taggacaggc ttcttttgctg  23100 aatctgatgg tgggccgagt ttttctatcc cccctccaat aaatgtgaca aacttttag    23160 actccttcct ctgtggattg cctcttgctt ttgcttcctg cccatcgcca taaaagaaga   23220
taatgacaac aaaacgataa caacacaaat gtaaacgtac cttttcctct taacttttcc   23280
atatcatcaa tttctcatga attaaggtgt gatacctgaa agtcacattt gccttatcag   23340
ttatattcat atagttcctt tgtcttattg atgtatctct catattatcc ctcatatcca   23400
cttctccagg ccttttttcca ccccatgtca gtctagattc tcttggcttc tcacttggag  23460
cgtcacagca gcctttaagt tgccacttaa ctccacttct tgttcatctt gtttgtcaga   23520
aatctgaagt agatgtgttg ttgcaatgat atcacatgtg ccattctttg ttttgggggt   23580
tttaaggctt ttaaggttat caaaatattg taataaccaa ttgtcttaat tgtattttgt   23640
acttattctc ctgcttttgc caacttaaaa tgtcttaaca tcctgttaat actgaatgct   23700
gatgctttcc tattcccttt tctttcacat gtccgtctat aattgtttat tgattatatc   23760
agtctctcaa cactaaaggc accagtcaca actttgatgt tatacagaat gacaactaaa   23820
aggtgacaaa tgctaatgac ttaatcgagg agttgttcat ttttacaagc ttacctgagt   23880
tcagagaatt ggtaaaagac tggtgacttt tggctactat ctaaatataa ttggttaatg   23940
tagctcctgg agatcagtgg ttagtataat actcttagtt gagcagggtt aaaaataatt   24000
acatttgttt aagttgcaga tactactcta ctgtacagca aagaatgtta aaatgtttta   24060
attcagtata tgaagagcaa aatataaaaa caggttttct tccactctca ctagcaagca   24120
aagtggtctg tattttgaa atatattttt tgtttaatca taacaaaata taatacaaat    24180
gttattaaaa gccctatttt atggatgaag acagtgatat ttagagatat taattagctt   24240
ttccaagatc atacatttat ccagtagtaa aagcaagttt tcacaagctg atctattta    24300 ttccagtctt tatttggaat cactaaactt acattccctt tagcaaaact atcgtttaca   24360
```

```
tttctagggt tcaagagtt caatgctaaa cttgggagat ctattcttaa attctctcaa   24420
agtgcaacac attttcctca ggatgatcat aaagtcatca gatgtgtgtt aagcaatata   24480
tatagtcata tactcttgat caaaaagat ttccaggtta cacagaagag agatttatgg    24540
ctgagaaaaa ggcagattgc ttctaagaaa ggcttcaaat atattctctt ctgacaggct   24600
acaggagagc cagctagatg aaccattaca gtgtgtacaa aatgctcagc agaataattt   24660
ctcagtactg gtagggaaga gcaataggag taacacaaga gaaggaaagt tggtctgcag   24720
agtctgcctt agtatccgta ggggtgatga ggttgcttgg gctaagaatt ctttcacatg   24780
tctccctggg acaattcact cagaattact tctgtgtttt ctaggctatc taggcaacca   24840
tcaccaatta gcaaacacag acaaaataga acaccttgtt tggacctgct tgtcaaaaat   24900
caaatgatca taatttataa ttccaggaag acttgccatc aaatgaactt atgacaaatg   24960
acccaaatga ttctcacaaa gtagagcttg ttgtaacttt tagcatgaga agtatgaacc   25020
ccattatcat tttttaaaca ttttgagtta aatggaccgt tttgcaaagt ccatgttcta   25080
tctttataga cagctcaaaa atagctcagc atctagtttg taggttggct ccatttaagg   25140
agcttgaagt caggcaaggt gctcattact attcatccag atctgtttct tggacacctc   25200
agctgttttt cttttctacg gccagggagg agagtcatgt gcatagtcca agaatgtgca   25260
tctccatgtc tctgaacagt tggccataga attggagcta ggtgttcttt gtgccattgg   25320
cttttcctctc tggcatgctt cccgggtggt tggagccagc cagtgcctga tccagcttca   25380
cagacccagt aatgaaattt ggagggcaga gtaggtaact aggtacacaa gaattgtaaa   25440
gcaatgccca tctggacagt tgatcacaac tataacttct caataatgta acaggaatat   25500
aaactgttag acttcctata ccattgcaat ataagaaga taattgaagg ccgtgaagat    25560
agctcatgaa atgcaaggaa gaattggaca actaagcaac aggaagagca gagaaacagt   25620
gagactttgg gagtcacaag atctgggtgc ttaaattctg ccaggacttt cttgccatct   25680
tcatttttgc tcctctttct cggtcagttc tcttctgtct ttccctacag accagctttt   25740
ttccacatgg atatgaaacg tttccaagtt ttatatccta ggggtttgc cactgaagga    25800
ggactagcct gatattttcc cagactcata tcctaaggaa gatgaatcat tagatccaag   25860
taatttcgtg caactggaga agacttgcag accctaccta atgggttaag ctggatatgc   25920
atctgtggga gggagatatg tttgtgggt ataatacaca tgcaagcaaa ccttaatatt    25980
gtacaagata cgcttctgaa aatttacttg cagtttgaaa atctggaagc caaacagtag   26040
accaactgtt gtgagtgtta gaattagtg taatggcact ttctgtgacc caggcaactc    26100
tgcataggca gaaagattct tgaaagcccc acccaggttg gaaagggtct gtgtcagagg   26160
tcatgagtgg gactcttcag gcacctgttt ccccatccca aggtctgcac atggactgga   26220
acaaaagttt tggcagctgc aattttaaaa tcttttccca agggtatcta gggatttaaa    26280
gcagtaggga atgtactccc ccactttccc ttgttttcct tttcactgca gcaagaggca   26340
agtatagccc tcagccctgc ttgtaccctc acaggagact catgtacagg tcccgggctc    26400
tggctgcagg acagtgtgag gctgctgaca gggcgagaga atggcagaa caatggaaca    26460
ggactgaggg agaaggaaga ggaatcgtcc ccagaactac tacttgggac ggtggtccca   26520
gggagcaaaa aacaccctg gagcccttc aaggggcctt ttggcagagc ggtactaccg    26580
ctagacactg ccatggctgc aggtaggact gattaaagaa tttctgattt cttctgagga   26640
cagggtaaag ctctgaattg tttttagaga ctgcattcag atctatattt cggaaccatc   26700
actctggttg cactgtgaac ggtaacgtcc agggagcagg actggaggga aggagaccat   26760
```

```
tacgtggctg ttgctcctgc ccaagcaggg aacaatgatg gcggaacgcc tgtactggca   26820
gagaggagag agaggaggga tttggcgaac ttttggaggt attggtagga cttggtaata   26880
tattgaatgt ggagagcaaa tgggcaggga gtcagtgaca aagcctaggt gtttggcttt   26940
gatgactggc tatgcctgtg ccggttgtgt acagaatcca gaggtttagc gtttccatgt   27000
gcagcgtcgg tcctcattcc gcggcagcct ggtgtggagt tgagatgtgc cccctccact   27060
ccatgttcac gtttctttag ccagagcaaa gcatgcctgg acaacctagg tttctttctt   27120
tctttctttc tttttctctag agagagaggg tctccgctct gtcacctaga agaagtgcag   27180
tgtcgtgatc atagctcact gcagccttga actcctggcc tcaagtgatc agaggattag   27240
gtgtacttct ctacaaactt ctcaaacctc cttcagcatc tcattcctta agggaccttta  27300 cagtctctcc cacctggacg gcgccatggt gcctcattcc atttctgaga attgtcttaa   27360
aactttatat agaaacttgc tattatgtat ttaaatgaga agaaatgttg aatttgtaat   27420
tctaattttc taagacaaga gtttgtagct cgcttctagc agagttaaag aaaaagatat   27480
gatgaatggt ctatatattg aaaactgcag aagaaataat ctaatatgga atgggtgagg   27540
ttgctacagg tggtgcaaaa ataattgcgg ttttgctgt tactttcagt ggcaaaaacc    27600
gcaattgttt ttgcacaaac ctaataatac tgtttgaaat tcatattttc tggtggaaca   27660
gtcttgagat agagcgggaa ctagattatt ggctcataaa acagcatgca gttactgtta   27720
ttccttaatc ttatatcttt attatgaggt aatgcttctc ttacttgatt tggagaatgt   27780
tctcatcttt ttctcatata tttgtgaaaa ctaaatgtta aaggaattaa cataacaacc   27840
attgctaaat tatgatgtaa aataatactg tgtctgcaat tagcctaggt agttttactt   27900
ggttcaataa tataaaatca ctaggctcat aatattttag taccttagtg tgattggcca   27960
agaaaaaaat tcacgttacc ataaaaagtc aaaccaagta acaattaatc taaatttcaa   28020
ggaaatataa agcaaagtat tatgttgtaa catggaacat taatgtaaat aactccccaa   28080
cagttcatga aatagattct gaactggcag ttgacaaaga aaggctagtt ttggcttaat   28140
tctcttatgc tccaatatct ttcctgaagt cttatttaat ttcacttgcg ttagcaacag   28200
tactctgaga tggtggtgca tctggaaaat tatcacttct ttcctgacaa tcagtatctt   28260
taatttaatt cttacatatg ctttctggaa atattacatt catactttga tgacgtctta   28320
aaaataattt caatgtaata attatacatg tgtggtgagt aaattgtgtt ccgtaaaaga   28380
tacttttaaa tcctaatgtc tgtatttggg aatgtgacct catttggaaa cagggtcttt   28440
gcaggtatga tcaagttaaa atgagatttt actggattag gatgggtcct aatacaatga   28500
ctgttgtact taagaggaaa atttgtacag agacatacac acacacaaaa gaatgccatg   28560
taacgttagg cacggagaac atcatgtgac aatgaaggca gagattggag tgatgcatct   28620
atgagccaag gatggccagc aaccccccaga agctggggag agacaaagga tgcttccta    28680 ggatctccag agcaagcata aatctgccag caccttgatt taggacttct ttcctccaga   28740
actgtgagaa tagatttcag ttctaagcca cccagtttgt ggtactttgt tataggagtc   28800
ctaggaaact aatgcaacat gctatgttgt aaataaacag tagttctaat tggtataaat   28860
aataatttta agtatatttt attattaggt caggtgagta ggaaattgcc tggtagacta   28920
attatcaatg ttgtattttc tgaaaagtta aaatattccc attcagtaaa taatacttgt   28980
ctaaaagttt ctatctgtat tgtcctaaaa caaagcaaaa attaaaatgg agtcagttat   29040
gtacctgaaa aatgtgaaaa aggaaagaaa aatcttttag gaaagatttt tcctaaaatg   29100
gctatacatt tgagaaagaa ttttaaaact taaatcatct ggctgtttat tccattttt    29160
```

```
tgtttacatt atcagataca ttatgtatga tttcatacat tatgtatgtt acattcaatc    29220
aatatttatt aaatacctaa aatttgctag gccttgagct aggtattgta gataggtaaa    29280
taagacaaac attcccttcc cctaaagaga ttattttggc atgaaattta atctgtagaa    29340
gaagtgaaag aggccatttg cagagtctac catgaaaatt cattttcact atctgctgta    29400
gttttacctg atcctgtgaa accatttttag catcatttgg ttttactttg tgcttctgta    29460
ttatattgga gaaataaaa tttacttatt gcacagacaa cataaaatta attaaagtat    29520
gtgaaaccaa aaatgtaatt gtttatcaaa tttttttttag tgtttcccat tcatcagtat    29580
ccaaatacat tcttagttgt gcatccatgt tagcataact aaaatgtggt gttcttattt    29640
tttcatctaa ttcacaatca acaatgttca cttttccact ttttttttttt gagacagagt    29700 ctcactctgt cacacccagg ctggagtgca gtggcatgat cttggcacac tgcaacctcc    29760
gcctcctggg ttcaagcgat tctcctgcct cagcctcctg agtaattggg attacaggcg    29820
cccgccacca tgcccggcta atttttttgta ttttagtaga cagggtttt caccatgttg    29880 gtcaggctgg tctcgaactc ctgacctcag gtgatccgcc cacctcggcc tcccaaagtg    29940
ctgggattac aggcatgaac caccacgcct ggcccctcat cattttata att             29993

<210> SEQ ID NO 2
<211> LENGTH: 29993
<212> TYPE: DNA
<213> ORGANISM: Artificial Sequence
<220> FEATURE:
<223> OTHER INFORMATION: chemically treated genomic DNA (Homo sapiens)

<400> SEQUENCE: 2
ttggtttttt tttttaaggtt gttttttaaat gaaattaaaa taaaaattat gttttggatt      60
atgagttttt agagcgtttt gtttaatttg atttatataa aatttaatgt taagatagtg     120
ttatgtacgt ttgaaaaata aataaatagt aaatggtaat tgtagaggta ttttatttta     180
gaggagttgg ttaagggaat tgttaataag tgaatttat atttttattg atttatttta     240
taaagtttta tatttttat tttttattt tttttaaaat atattttttt ttagattgag     300
ttgaatatgt ataaatattt tgagagtttg atttatgtta tgtagggttt attggtgttt     360
ttgaattatt ttaagaattt ggtagtaggt ttttgatttt aatttttttt atgtgttttt     420
ttaggttttt tgcgtttttt ttattgtttt atttttttt tttttttat tgtttgtatt     480 gtattgtatt attgggttaa tagatgttag ggaagggtaa tgagtaatcg gtataatatt     540
ttaggaaagt gatttgtttt ttaattgtgt atttatgaat tgtttgtatt ttattataaa     600
taagatagta agtaaaataa taaataatat atgaattta aaaagacgtt ttaatttag     660 agattttaag tatattttag ataagaaag taataattaa ataagtatag aatttaaaaa     720
gtaatatttt aaagtaaatt ggatataata ttttgtttcg gttatgaaaa ggggaggttt     780
gaaaatattt tttggtgagt ttgagggata tatggaatgt aatttttttaa attaatgttt     840 tttaaattgt atgtgagata attttaggtg gtatatgaga ataattttt atttttataa     900 tataggttt tttgtaagat tatttttttat ttatggcggg ttttattagt tttttatttta     960 tggtgattat aaaaaatgtt ttttattaga taaatttatt taataaaaat agattattta    1020
aagatatata ttaagttaat aatataggcg atatggttat aattataaaa gtgatattta    1080
atgtaaatgt tggaaataag gttttatttta agtaaataat atattttgt ttttataatt    1140 ttaaaattt gtttttatg ttaaatttat tttaaatgtg tattgaaaat tgacgttttta    1200 tttgatattt agtggtgttt atgttaatat atgtatattt aagataatta ttagaaggta    1260
```

```
gtaatatgaa gttaaataat taatatatta ttttggattt taaaaataat ttttgtatat   1320
gtatttttat ttagatgtat aaaaaattat gtaggagtaa agtgattttg aaagtaaggt   1380
tagtgtaatt gaaaaatttg attttagaag ggtataaaga aatatgttaa gaaaatttat   1440
tttatattta tgttaataat atgttaaagt atgaattttt attttattta aattatatat   1500
tttttatttt tatttgtagg tgaaattagt ataatgtt ttatgttaaa atgaaattta     1560
aaatgttgtt gttttttgag gatagtatta aattattat tgtatttaat ttttatatga    1620
tatttgttat agttatagaa tattttttaga tattatgatt tataaaatat ttaaattgta  1680
tatttggttt gtaatatatt atatatttaa aagaattatt attttttttga atattattaa  1740 tattaataat agtattatag tgattaagag tggatttaaa taaaggttgg tttgaaattt   1800
aggtttgtta tttattagta agttttttaaa aattttgagt ttttagtttt tttatatgtg  1860
aaatggagaa aataaatttg taaaattaat taaatttgtt tatttatatt ttttttttta   1920
gtgtatatta attggtattt ttcgttaggt tagaatgtgt ttttaattat gttttaaatt   1980
cgttttgtgt taatttttatt gttagaattt ttttttatttt gagaattaga aaaggaaata 2040
ttatgtttgg taatgtttat attttttaaa ataaatttgt aggaaagaat atttagtaag  2100
tgatgagagt agtaacgatt gttttttatta ttttaaattt ataatattat ttttttttaga 2160 gttttttaag tattgtagat aattttttat ttattaaaaa ataaattgta attataagta   2220
tttagggttg atattgtttt tgaattagat agtgtttata ttagttgtat aagattaatt  2280
taaagtagag gatgaaattt tttttttgaa tttttttttag aacgtaattt agtgaatata 2340
ttaaaattaa attttttttg aatgggagta attttttacgg attaatttgt aattttttag 2400
attatattta aggtaatgta gaggttgttg tattataggt tttgtgatta gagattattg  2460
gatttgtttt tggaaaagtt atttatgatt ttttgggttt tggttttttt attttttata   2520
tcggtttaat aatgattatc gtagagttgt tatggaagtt aaatgaattt atgtattata  2580
agtgattaat ataatgattg atatttagtg atttattaat aaattaaaat atttattatt   2640
aatatgatag agaaggtgtc gttaaaatag ataataggtt tttggaagag gtgattaaat  2700
ggatgtaaaa tttatggatt gttttatttcg tttattttttg ttgtgttttt tggttgtggt 2760
atatatacgt gtgggtataa aatcgtaaat tttatgtagt cgcgtagtgt atgcgtagaa  2820
ggtttagata cgaaatgtta ttttagtaat gtgtttagag aagttttgac gtcgttttgg  2880
aagtaagtcg ttgttgtttg attttttgggc gtttgggacg gatgtttata tttgtattta  2940
gtagtattgg aaggggttta ggttttttcgt agtatagttt attttttagat cgtttagttt 3000 tttataatat atattttttac ggaaaagggt attttttttc gttagaaaaa gcgttttagt  3060
ttggtttggg ttggttttta ttttacgttg ttgtaagtag gcgaagtttt ttttgttttt   3120 tttttgggg taagtggaaa ggagttcggt aggggttcg tagtggtttg tataggggaa    3180
ttgggtagcg agagagtttt aggtaatttc ggggggttgtt ttatagaagt aggtggggat 3240
cgatagtggt ttttcggttt agggaggaga gcgcggtcgc gggttttttt tttagttttg  3300
gaggttgtag tcgttcgagt cggttcgggt ggggcgggg tggggcggc gcggagggta    3360 cggagattac ggcggcgtta ttcgggatat ttagggtttc gaggttttgg gcggttttta  3420
cgcgagatcg taaattatga taataggtag ttattcgagg ttaaataaaa acggagtggg  3480 ttttcgcgc gtcgtcgttt ttcgcgtttt tggcggtttt tttcgaggtt ttcggcggtt   3540
ttacgagttc gtagtagtcg gtggcgacgt cgttttcgtt ttattttttt gcgtaagtgc   3600
gaggttgtcg gtagcgcggc gtacgtttcg gtcgttttcg gttttcgcgt aaaatttttta 3660
```

```
ttttgtttac gtgaagttgt cgttgttta gagaggggga aagagttgcg ggaaaagtcg    3720
gggagtgacg attgcggcgg ttgggcgcgt tttttatt tttttttt tttttttt     3780 tttgtcgtag ttcggagttt tggttttt ttttttttt tttttcgg agtcggttt     3840 ttttttcgtt tcgttttt ttcgtttgtg tacgttattc gttgtgggt ggtcgaaggg    3900 gatgttttgt ttttattaga ggtatagcgc aaggggaaa ttcgatatt ggaaggaacg    3960 agaataaata tttaattacg gacgtattga atcgcggttg ggatagatat ttcgggaatt   4020
cgaggcggat cgggcgacga ggtgagtgat tttttttt aattttcgtt ttagggttt     4080 cggggagtt tgagttgaga gaattttaa attttcggg aaagtgcgcg aggttcgtc     4140 ggggacgtcg agcgttgggt attgaggacg cgtagttgga cggtgcgtgg gcgtttgcgt   4200
tttcgggggg cgtttggagg tcgggtgtt tacgttgag ggttcgggtc gttcggatcg    4260
tagcggtgtt ttttgtttta gaagacgttt ttaagttta agggttttt tcgagtttgt    4320 ttgttttt cggggtcggc gcggagttg cgcgtaacgg agtttattta gtagtttagc    4380 gcgcggttt tatttgtatt tcgttttat ttggtagagg cgcgagtatc ggggtttt     4440 ttatattttt tttatgacgt gtattatttt ttgatgattt ttttagatggt ttaggcgcga   4500 ggatgttgat ttagagtttt tcggagggtt ataggcgttt gggttttc ggtgtcgggt    4560 gcgtgtgtat ttaaaggtt cgcgttttaa ttttaggta ttgatcgggt ttttaattg     4620 cggcgatttt attttaatag ttttatgtg gcgtggattg aatgttttt gtagtttgtt    4680 agggtcggtg aaattagagg cgtttgtta gagtagtcgc gtttattggt tcgagtagcg    4740
ggtgttatgg aaggtttata attttttaa aggaagggat ttggttgggt agagtaggtt    4800 tttttttt tttaagtttg ttgggtttgg ggaggtagtg gaatttgaaa tggttcggat    4860
ttttagcgtg gtgaagcgag gtttggaagt agacgtgtgt gtgtttgttt tattttgcgt    4920
cgtatagtaa ttcgaatttt cgtttggtag tatttgaaag agttttttt ttttgtttgc    4980 gagattttga atagttcgga gcgattaggg aatttgcgga tcgagttcgg tggtagagtt    5040
ggggcgaaag tagagagcgt aatttaattt ttgttatttt ttttttgttt gggaggatag    5100 tgttttttt tattattatt ttttttttt tttttatga agataacgga tttgcgtttg     5160
gggtgagagt gtgtgcggga gagtggtgtg gagattgttt ttttttatcg cgttttttgc    5220 gtttttttc gttatttcga gcgggttag agagttattt atgaattta atttgagggt     5280 aggggaggaa ggtgtaggtt ttttgttt tttgttaag gtgtagaata gcgttcgggc    5340
gtgtgttttg gtttagagt agttttacgt ggagtaattt cgtgtgtgtg tgtgtgtgtg    5400
tgtgtgtgtg ttgtgtattt gatttgtgag gaggtaatag gattttggtg tttaaattta    5460
gtgggtcgtt ggttattagt ttgttttt ggttgttatt atagatattt ttaaaatttg    5520
atatttaaga gaattaatag gttaggtttt atattaaggg tttatattta atagttttt    5580 tttttttta ttttttggg tttggtatt tgggattaac gtaattgttg gagcgaaata     5640 tatttttgg aatatggtat tttgttttt ttttatttg tggttatttt gtgaattttc    5700
gggtgtttgt tagtttagt gcggttttt gcgggattta ggtgggagtt ttaggagcgt    5760
ttaataatcg cgggttttt attagtagtt tttgaagttt tatttatacg taggtgattg    5820
ataggattga aagttgacga tggttttt gttttgtgcg ttgttttgt tttaaaatt     5880 ttagggaagg gattgtattt gaattttt ttcgggtacg gtttggttt aagtagaatt    5940 agtgtttttt ttttttttt tgttttaa aatattattg gtaagtttaa atttgaagaa    6000
ttaaaaatta gaggggtgg ggagagaatt ttttaaaa atatttgata cgtgatacgg    6060
```

```
agcgttttag gagattgtat ttaaagatat ttgtgtattt ttaaaaataa tattatttta    6120
agaaataaaa agtagtagta ataagagata gattgttttg tgtggagtaa gattgttaga    6180
atttgatttt tatggtaata atatcgaaag tagatataat tatatttata tttattgtta    6240
taaatcgtaa aaatagtttg ttttatttga ttaaaagttg taagttattt aaagttaaat    6300
tcgtatttag gaatgattgt ataagaatgt taaaatttt gatagttata gttttgaaag     6360
taatataatt agatttgttg aaaatgtttt ttttttttga ttattagtga tatgtatttg    6420 tttttataa taagtaaagg tttataatta atatggtttt taaaagtttg ttttttttg      6480 taaattttt gaaatagta tgttttaata tttaagatt attgtaatta tcggttggtt       6540
tataattata attaaaataa gatttattta gttgtttttt ttttattagt atttgttgaa    6600
tatttgaaat tgaattttt attttttaaaa taaaacgttt tatatatatg tatgtattta   6660
taattaatat ttttttttaag tagtaggttt aagttttaaa ttttttaaaa ttttaagatt  6720
tgtataaaaa ggagtgattg tataaaaagg aataataatt attaattgtt aagaaaaata   6780
gatgttgaat tttagagggt ttttagaagt tggagaaaaa aattgtatag agtttttttt   6840
tttgacgggt gattggtaga tgagttattt gttattttgt tataatttat tttttttttt   6900
taataaggtt ttttgggtta aaaaaaaaaa aggaaaaata agtattttat ttttaagagt   6960 tttttttta tttatgttgt attttggggt gtaaataaat tttatatagt tacgggaaat    7020
agagtattta attttatgtt tttagtttt gttgtaagtt ttaaatgatt gatgtcgtgt    7080
ttaaaaatat atttatatgg tttgatattt tattttaata ttttatgtat tggaattaga   7140
ttttttagga tttttagaaa gatagaatga tagaaagacg atgattattg ttataaaaag   7200
ttagaatgtt aggaagttta tattttaatt tttaaataat taaatttatt ttgttttata   7260
aaaatttata gttttatat agattttaag aagaggggtg ataattttt ttattattta    7320 gttaagtgtt aagtaattta agaatgtaag tatgtattat gtttttttat tattattttt   7380
ttttgttagg taaatgtaag aatattggat attttgtaaa aataggtttt tttttataag   7440
gagtttattt attatagttt tgtattgtag ttgttgatta tatttatgg agttgttaaa    7500 gtatttaaaa tttaaaatta ggtattgttt ggttgtaaat attttagatt atttatttaa   7560
gaaataaata gaaagtgtg ttattaaaag taggagacgt tttgaatttt tttattgaag    7620
agttgaataa attttatta aaatatttt ttttttttt agtgagaata taattttgat      7680
agtttttttt tttaaatgga tattatttt atatgtatta aatgttaaat tttataacg     7740 tgttttttg tagagtattt taaattaatt atatttagaa atatagttgg gggattttat    7800
tataatggtt attaggtgaa ggaaattaat attaggggaa tggggtggta ttgtagtgta   7860
tttgtttttt ttatgaattt ttttttgttaa attaagaaat gatatgttgt tttaggtatt  7920
tgttttggag atgggtgaga tgtaatatgt gtaatgttgt attttatagt tagatgtgtt   7980
ttaatgaagg ggatattgta tagttattaa attattttg gagttaaatt tggcgttatt    8040
tagtttgaat ttaagtggaa gaaaatgaat aagagttata tatttaaaag aagtataagt   8100
aattttgatt gttttaaga ggtttgaaga ttttgtaaat attattgtta tttaatattg    8160
tttgtggagt tgtatattaa tatatgtttt ggtgatatgt tattttacgt ttgaaatttg   8220
ttatttttag tgtttttta tttattttt tattagtaaa gagatattga aaatgaatat    8280
tattattttt atttttttaa tttttttat atttttagaa aaagagatga aattgattaa    8340
tttaaaatag aaattatttt gtgttattaa aattatattt atatagtgat ttgagatagt   8400
tttagagagt gtatttttga gttttattgt aatttttttt gttattgaaa ggtgttaatt   8460
```

```
gattttaggg tattgatata atagtatagt ttgatatttg aaattttttta gagttggttt    8520
ggttttttt  ttattttgag attttagtgt atggatgatg aagaaagata ttattttaaa    8580
atattagaaa ttttattttt ttttaatat  gaaatgtttt aatatagtat gtttatattt    8640
ttaaagtttt tatttatata tagtaagtaa atttatttta acgtatttt  ggatagtagg    8700
agaaagattt atatgtttta tcgtgttaga attttttagt ttttttttt  ttgtataggt    8760
agtttattta ggttataatt tttaggtaaa gtttgatttt tattattata tgaatatttt    8820
taaagtgaaa ttgcgttaaa ttaatgtgga atagttttg  tattattaag gtatatatta    8880
atgtagatgt taaatatgag agtatatttt tttgagtata tttatatttt aaagtgtatt    8940
tttaaataaa agtggttatt gtagttttta gataattata atttggttgt tattattatt    9000
ataatattaa ttattattat tattataata ttatagttag tatttattta ggaatttcgt    9060
gtaaaatatt gttttaagta tttatatgga ttagttaatt ttaattttt  taattatgtc    9120
gtaaattagg tattttttgtt attttttattt tatagataag gaagttgaga tttagttatg   9180
tagtatagtg gagttaggat tttaattttt tagtatgagg ttagtattttt tatttttaag   9240
cgtgtgttgg gtttttgttt ttattagtta tatattatta tttttaggtg gtatttgaat    9300
attttgttttt aataatattt atattttatg taaggataat tagatattag aaaaatttgt   9360
taaattttgt attaaattg  taatttttatg ggtaatattg tttgagataa gattaaataa   9420
agtattgaag ttaaagaaaa aaaattaagt atttgaagaa acgtattaag taatagtgaa    9480
taagaatatg gtttaaataa ttatagttat gaaggttgga tagtaaatga ttgaatttgg    9540
agaaatgttg tattttgtaa tgtttttaa  ttattaagaa tttatgatta gattttttaa    9600
atatttaatt aatatgtgga attttttttt gttttttaag ttttatttaa attggttaaa    9660
tgttattaat tttgtattt  ttttgttttt gtttttttgtt gttttaatgt tggttttgaa   9720
ttttaaattt gtatatttat gttgaattaa ttaataaggt ttgaagagtt aaagagtgta    9780
tgatggattt ttggaggtag gtttaaatta taatggagtt gtttatattt tggaaatata    9840
tttaatttat ttggttatcg tatgtgtaag gtttttttgta ggtaaatatt tttgttgtta   9900
ataatttgtt ttataatttt atagtatttt tttattgaag agtggttttt tatttttta    9960
tttattttata tatttagtta cggatttttt tatttaaatg gaaattgatg atatgtttag  10020
tagagaaatg tgttattgtt ttaggtgaag taggatgtag gtagtttgag aatgatttat   10080
taatagtatt tttttacggt ggtcgtcgtt tttggagttt tttttaagtg ttttttaatgt  10140
atggaaattg ttgtaaaaaa atttaagttt tttgataaaa ggggttaatt tagagtattt   10200
gttttaatat gtttatgtgg tattattaaa aaatagattg ttagatacgg taaaatattt   10260
tttagtgtga tatattagta gaaaggtgtg tttattttt  ttttttataat ttgagtattc  10320
gtattaatta gttttttaaat tcgatttagt attgagaaaa ttaaaattga ttaaaatgtt   10380
ttttgtgtgt agttataggt ttgaatgagg tataaaggat ttgtatttgt aaaggttgat   10440
tttattaatt agaatatttt tttttttta  aagattgtaa gaagaaatat tagtagtggt   10500
ttaatttgat atgatttag  attttttacgt aaattattgt tattatttt  gttatttttt   10560
tttttttttt ttttaaaatg aaagggatat tttttgtgaa agattataat taaattataa   10620
aaatttatat ttatgtgtta ttaagtttaa ttttatttat aaaagtaata gtatagagtt   10680
tgaaattttaa tttttaatta agtaggtgta ttatatatcg ggagggttta ttatgtataa   10740
ggttatatat ataatttata gattttttgta tatatttaac ggagtgattt atttattata  10800
ttttatttt  gatttgaat ttttttaatgt taaaagattt gaaaagaatc gaatgttttg    10860
```

```
attaagagat tgaatatttt taatttaatg ttttagtat gttgaaagtg atgatgattt    10920
gggggaatta gtagattttt atattatta attttttt tttatattg aatgtaaatg       10980
tatatttatg tgcggttatg atttaagtta tttttgttaa atttaatgac gttgtaggtg   11040
aattatattt agatttttt ttgtaggttt tttagtaatt taaaataatg ttttagtag    11100
gtaatttaag tatgtaaatt ttaataaatt tgttaagaac ggtaattta ttgttttatt    11160
ttgtttttt ttttgtttgt ttgttttgt attaatttta gttgataaga tgatggtatt    11220
gttatttttt ttagttgatt tatgaagaat tttaatttag gtttagtttt ttttttaat    11280
tgttgatttt agttttaaa ggtttcgttt atgaaaatgg ttagtaaagt tgtgggtatt    11340
tggtaaatgt ttgttaaatg ttttttttt attagtgttg ttgaagatt gtaaaattag    11400
agtgggatgg atagattttt tttttatttt gtatggtttt gaagattttg gagttttat    11460
tgtatttta tatttata tattatttt aggaatattt agagagagaa ttattgtaat       11520
taaggttata ggtttaattt ttaggtattt aaattagttt taggtggata attgttttat    11580
atatattgt tcgtattaat gttgttataa taaatatagt tataatattt tgatgttttt    11640
tttggggtt tattttggat tgtgttgaag ttgtttttaa tattttttta cgttttaag    11700
atatttaatt atatttgttt atgattttta tgaggttttt tttggattta aaattttta   11760
aaaaatttgt ttgttgttta tagggtaaat tttaaaattt tttgtaggga agataatttt    11820
ttatattgag aattttgttt aggttgtttt tttattttt tatttttat ttataataat     11880
ttttttttt agttgtatgg aaaattgtag ttttaaata tattttggat ttttttattt    11940
tatttttg tgcgtggaat gttttttt tggaaaatat cgttttttt tttttgtaaa       12000
tattttttt attgttttt taatatttaa ggtgtaaaat gttagttttt ttgataagtt    12060
tttgattt ttagagtttg agttgaacgt tttttttg ttatttttaa agtatttagt      12120
tttatattt aatatagttt ttgttatatt gaaatgtaat agattatatt agtttaaatt    12180
ttgttttaag ttgagaattt attggaagga ttagttgtat ttgttatttt tgtatcgtta   12240
atgtatagtg tattgttgga tatatagtta gtaggtagtt gttatatttt tattgaatga   12300
atgagtagag gtattgggaa tgagagtaga gattgtgata ttgaatattt ttttttgag    12360
attgggaata gtgagaaggg tagtgattat tataaggtgg gattattta ataataattt    12420
tagggagttt tggtataaat ttagtagaat tgtagttgtg aatttaggtt taggttatat   12480
gtatgtatac gtgaatgtag aaatgtgttt attttttatt attgggaagt tagtgatttg   12540
gtggataagt taaggatttt gaaaattttt ggagatacgg taattttata gtatttgaaa   12600
tttgagagat ttagttttta tagtatagtg agtaagtaga aagaatatgg gggttgggcg   12660
cggtggttta tatttgtaat tttagtattt tgggaggtcg aggcggatgg attatttgaa   12720
gttaggagtt cgagattagt ttgattaaaa tggtaaaatt tcgtttttat taaaaatata   12780
aaaattagtt gggcgtggtg gtgggcgttt gtaattttag ttattcggga ggttgaggta   12840
ggagaattat ttgaatttag aaggtagagg ttgtagtgag ttgagattgt attattgtat   12900
tttagtttgg ataatagagt gagatttat tttaaaata aataaataaa taaaaggaa     12960
gaagaatatg gagttaggta tttgggttta gattttagtt ttaatattga tgagtttgta   13020
atattaaata tattattgaa atagattttg ttttagttt ttatgtgtaa tagaaatgt     13080
tttatgggt tttgatgaga attaatgag taaatatatg taaatatatt tagagtagtg    13140
tttgatatga gtattagttg ttattattat gattgggtat ttttattag attattttta    13200
aatgttttag agatattag agttgaaggt tttttggg gggttatgga ttggtgatta     13260
```

```
taaatggagt gtttagtagt ttaagtataa attagatatt gtgggttatt ttggtaaatt    13320
tgaggttgta tttggagttt taagagaaga tattataggt gtttaatagt tggtattggt    13380
tatttacgtt gtgtagtaat attttttta gtaaatattt tcgtatatag taatttagat    13440
tgttttagag ttttaattg tgtggttttt taattatttt aagtaattat aagtacgttg    13500
tataatggta gtattttata gttaatattt aagtttttt agttgttttt tttttagtcg    13560
taaggtatta attatgagaa tttgtataat tttaatagt tagtgggttt gatgaattta    13620
atgtaaattt tttaaaaggt agttttatat attgttatga tttttatttt tagagagata    13680
gtaggaggta attagtattt ttatttatag aattattat ttggatttag atataatggt    13740
tatgtggtag gatggggttg aaggaaaaag gaaagttaaa atattaattg ttaaggtttt    13800
atttttatag tttgtttgga attgttatta ggtgtatttg tatagtttta aaatgataa    13860
cgttgtattt gaattttta gtatatttaa ataagagttt tttaagtttt ggttattgat    13920
attttgggtt ggataattta tttaggggat attgttttgt gtttggtagg atgtttagtg    13980
gtatcgttgg atgttaggga ttttttttt tttggtaatg atggtgtttt tagatattgt    14040
taggtgattt ttgggagtaa aattgttttt ttttgagaat ttataattta agtagatttt    14100
aatattattt gatatagtta aaaaatttt agggttttgt ataagaggat tgttttattt    14160
ttagttaagt gtggagaatt ttaatatttt tttttaagt ttaaatatga agttaaataa    14220
tttttattag tttgtgttga tagattaatt ttgtatagag gggatttata gatacgtttt    14280
atatagattg attattta gtatatttt ttttttgga aataatatat gagtgggagt    14340
aatagaatat ttgagagaga gtatgtagga agtaaatatt tatttgaatt atttatgtgt    14400
tttttttttc ggttatttgt tagtagatag tttggatta ttttaaata atgattattg    14460
ttttttatt tttgtgggta aatatttagt aataagaaat ttttatttta tttagtttgt    14520
agtgttagaa aaggtaaagt tattgataat tataattgtt gaagattaaa atatttagtg    14580
agttaaatta tttgtttgta atgagaaatt tttaaaagaa ttatgtgtag ttttagttg    14640
taattataag tttaagattt tgagttaata atatttgtat agttagaaga agtaaaaat    14700
aaatatatta tatgtaaaaa ttttttttg tgaattta gatttaaatt tttaagtttt    14760
tattttatgg gtttgatgtt gattaatata ttttatttat gaaatgatat ataattgatg    14820
taagtaaatt tgattgttgt ttgggtatta tttttatata atttaagtat atatgaaata    14880
tattttaaaa attatttgaa taaaatggga ataataatgt ttatataaag tgagagagga    14940
taattttt tatatgagtt ttgggttgaa ttttaaaatt attttgaaat atgaaatatt    15000
aatattataa atatatgatt agattaattt ttttaagagt tttaaatagt agataatttt    15060
tatttatta gaaattgtaa agatatttga aattttatat ttatgtattg tttaatttag    15120
tggttgtatt ttaattgtat taggtagata attatggaag tagttagatt aatttggaga    15180
ttttatatta tttattaatt gatgtttaag taggtagggt agaggtattt gaaaatatat    15240
atatatatat atatatatat atatatatat atatatatat atttattttt ttttttttat    15300
ttttttgat ttgtgttta attttgaaat gtgtgtttag gtggtaaagg gttgtaaata    15360
tagtatattg tgtttgatta aaatatttt ttgtttttta ggtggagaag gattttgtat    15420
agttttgt tagtagagag ataaagtggg tgttgggtaa tttaatgata ggtggaggtc    15480
gttttcgggg agtgttgcgg agaatttgag atagggttt aaattataga tagtggagga    15540
gagtttgtt ttatttatgg ataggaagtt taaagaaggt atagcgaatt ataggtttat    15600
ttaggtattt tatgttagat attgaacggg aagtttagta gttttttagt tattggagaa    15660
```

```
cggttaaaaa tttagaggtt ttattttttt aaatgagtat ttttgggtt tataaattaa   15720 ggaatttat  agagtattta agttatatat tttttttttt aggttgattt tttgtatagt   15780
gggttttaat gtggtaagat ttatttatga atatttatt  ttttataatg tcgttagtta   15840
tttttttttt ttttttggt  atatttttat tatttttatt ttttatggtt ttaattttt    15900 taatttattt gtttagtgtt tttttgttgt ttatttggat aaaataataa taataataat   15960
aatttattta tttttttaagg tttagtttaa atgttatttt ttttgtgaag tttttttaa    16020 ggtttaggta gaattagttt tttttttttgt gtaatattat agtatttttt ttggattgtt   16080
aatataatag tagattgtgt tggggtttat tgtatgtgtt tgttttttag agagattatg   16140
aatttataga ggggagagat tatattttt  ttttttcgta attttaatat ttggagatgt   16200
taatggaaat taagtgattg tattatttta tgtatatttt taaagggtat taggttttaa   16260
attagatatt tgtaaaggat gaattttgtt aatttttgg  aaaattggtt tttttttgtt   16320
tgtggttatg aaagtggtt  tattggttat tttttatttt aatttattta agtttttatt   16380
tgtattaaag tattattgat tttttagtgg aaaaataggt atgttcggcg tatattggta   16440 ttttaataa  attgatattt aaagatagat ttttcgttg  aggttatgg  ttttataat    16500 tttagttttt tttagaaata gattttgatt ttttgttg  ttttttgtta agatcgattt    16560
tatgttattt tgaagaattt ttaatttta  gaattataga ttttatttga gagaaagtat   16620
gttttgtatt tgtttgtgtt agtgttttaa aatgtgagga ttaaaatttt tagatgtatt   16680
tattaaaaat atacgtggtt ttttgttgag ggaaattata ttttttttt  taggtataat   16740 tgaggaagta aaaaattttt gtttagtttt tagtggtttg ttttaggta  tttttatat    16800 aaagatgagt aagattttt  aaaaattatt aatttgttta tttagggggg aaagttttt    16860 tatgtttaga aataatatta aattaagatt attgttttta atagttttaa aaattgtggt   16920 tttattttt  tgtatgagtt atttttttagt atagtgtagt atatgattgt attatattat   16980
gataaagtat atttgttttg tgtttagtg ggttattta  tttattagcg ttagatgatt    17040
agattagaag agagatttag tttaattttt ttatttgta gatgagatgt tgtattatgt    17100
gattttaaga ttttaagtta tttatttaga ataaaataga aaagagaat tttatgttgg    17160 ggatattta  tgtttttaat tttatatttt attattttat ttttatttgt tgttttga     17220 tgaggagttg agaatgttgg aattagatta tttttgtgtg tatttaggtt tgttatta     17280 ttagcgatgt gattttggtt atgtaatttt ttgagtggtt gtaagttata gttttagtat   17340
gtgtatatgg ggaataataa tagtattcgt tttatggagt tgtaaggaat aattgaattt   17400
atgtaggaaa gatatttggt ttagtgtttg gtttattata aaagtttagg ttatagtttg   17460
aattgatatt ttggaataaa atgttgagtg tatttgatat ttagagaagg aaatttatgt   17520
tgttaaagta agttttttt  tttaatttgt tatttaaaaa atataaataa gttatatttt   17580
gtataatata ttaaaataga gatgatagag gttattttttg agaggaatga ttagagggag  17640
taagagagag gttttggaat gttgattatg ttttttattt tggtttggtt gttggttatg   17700
tgaaagtgtt tatttaataa aaatttatta gtgattaatt tttgatttat gtattttatt   17760
ttattgtgta tatgttatat ttttttaaaa agttttaaaa atacggatat atttaaagta   17820
aaaagtggat ttatttattt ttattttttg taaattagga taagttgtta tatttagatg   17880
tgtatttttt taggtattt  tttttttata tatgtgtaaa tgtaataatt atgtgaggat   17940
gtaatttatt tttattttat atttttaatt ttaataggat tattgatttt tttaaaattt   18000 gttttttgatt tgttgaattt tgaatatttt tttatattag tatatatagt tttgggtgtt   18060
```

```
tttatttaat gtatgtagat atttttataat tttattgttt tttttttggt gtatgtttat   18120 attgtttttta tatttttatt attattaagt atgttgtatt gatgatttt atgtttttc    18180 gtatatttgt taaaaatatt tgtagataaa attttagatg taatattaat agataaatat   18240
gtatgtgtat tttttataga aaatattaaa atgtttttta aaaagattta tgaattttgt   18300
atttttaagg taatatttt attttttta taaaaattag gtgtaaaaat tttaatttaa    18360
ttgaattttg taattatttg tgttttggtt aagaaaaatg gttatagtag taatttttt    18420 gaaatttata tagtaatcgg aatattttat tatgattagg ataaataatt ttattaacga   18480
tatatattta atatatatat ataatttata taattagttt tttatttaag aatatttagt   18540 atttatttt atgaatgtat attatattta tttatggttc gtaagtttaa atgttaggaa    18600
gaaataaatt agtaatatta tatttattat atttttttt atttagtatt attaaatatt    18660
tattagaatt attaggagaa atggttttaa tttttatgtg attggtgaga atttatgagg   18720
aatgatatat tgttatttta gtaagagttt attttgtgtt aggtatagtt ttaagtattt   18780
tatatatatt acgatagttt tttaatatag agatgaaagg tatagatatt gtataagtaa   18840
taaatgatat tatttatta taaatgtgtt gataaatatt attatatatg ttataatatt    18900
agttgtgtta tattaatgat taatttataa atttgttatt tattataatt tgtttaatgt   18960
ggaaataaaa gttaatgtat taaaatttag aaaattgtta tttaaatgtt ggttaaagta   19020
atttgataga tatagttta aaatgaagta tattaattag ttgattttgt tgttcgattt    19080
ttatatgtag aaaattttgt ttttagaata tttagttttt gtagttttg gttaagattt   19140 tgattaattt ttaatggtta tttagtgttt ttaaaaagta gtttaattta gaatagttaa   19200
tgtatttttt ttgtattgaa taaatatggt tattaatttt tgtggggttt tttttttgt    19260 agaattttt gttatttaa gggatttaat aggatttata tatataaaat tgaaaattat    19320
attattatgg ggaagttgtt ttgtgttttt tagaaggaat ttttttgtta atttaagtat   19380
tgtatgtgtg tagaatagtt aatatttttt ttttaagaaa ttttatgtat gtagttaaaa   19440
tatttttaaa ttgattaagg atttgttata tatttttaga agtatttaag agtattttta   19500
tggttataag agtagagtgt attagaatgt tagaaattaa tgaatacgtt agaggttttt   19560
aaaattgtgt ttaatatttt tgattttatt atataaatat gtggggtagt ttggaaaaat   19620
aaaataattt ttttttttt aacgtaggtg aggtttgtga tgataatatt ttaattggtt   19680
tgaatattaa tttgatattt ttttgttaga agtaattttt attatttagt aaatgaaatg   19740
gagaggtaat aaatatgatt gatatttatt tttttgagtaa agtattattt tatattagat   19800
tcgattagtt attttattt tttttggaaa atgtattata taaattatta tagtattttg   19860
tttattaatt agggaagtta aaaaacgttt tataaacgtt gaattaaaat ttttattgtt   19920
gtgagggaat taaattttaa gtaatatatt tttttatag ggtgagaaat tgaagtatgg   19980
agaaattata aggttttttt aaagttatat attgagttat ggtagatata gaaatttata   20040
attttgtttg tttgatttaa tttgaaattt tatgaaacgt aatttattta ttttttgata   20100
tgtgttttag aagtatattt tttttatttgt ttatttatgt ttttatttat ttatttatgt   20160
atgtatttat gtattattga ttatttatgt atttatttat ttatttatgt attttaaaag   20220
aatcggtgtt tttgtatgat atagttttga tttagggatt atgaatattt tgaatttata   20280 tatttttagat atttttttaa agaaatttat tgtattttt ttacgattat gaaaaagaaa   20340
ttaagatatt aagaaaatta agttggattg tttaagtgtg ggttatagta gtgtttatgg   20400
gtagtatttg aagttaattt aggagtgaat ttagtttgtt taagtgtttg aataagaatt   20460
```

```
tggttgaagt tttggaggag atgtttgggg tatagagtgg ggacgaggaa aaattatagt   20520
atttttagag agtattgtaa ggattagtat ttatatttt  attatttgat gttttttatat  20580 ttggtttagt taagagagag ggggtaaatt attttgtttt ttattttgtt atttttttga   20640 ttttagttttt tacgttttaa attttttttt attgcgattt ttttttttatt agtttaatta  20700 gtatttttc  gcgttttttt tattaaattc gttttttttt attagtttgc ggagttatat   20760
tttttgatcg aattgttggg gttataagta atttgaaatg aggaaagtgt ttagtaattt   20820
tttttagttt agtattttgt aatagagatt ttagagtacg tagtgatgat atttgttttt   20880 ttttttttt  atagagagtt tagtgggtaa tttttttggt ttgttttttt gtttttttt    20940 tgtagtttta agatttagga tttagatttg ttttttgttt gtatggtttt ttatttttt    21000 ttttggaaga gttttttttc gggggttttt taggtttaag agtatttgga ttttggggag   21060
atgaatttgt agattttata aagaatattt aagtattagg taaattatat ttttttgtag   21120
tttaaacgtt agtttttttt tttttttaa  ttttattgaa gaataattta gttttttaata  21180 aataagtaaa tagaattttta gggttttttt taaaggtgta ttttttgttgt tttgaagatt  21240 attattatta attttttattt tagttaattg gttttttttt atattttta  ttgggtataa   21300 atgtgatatt ttggtatata ttaatgttga tttatattaa tacgttaatt tataattgag   21360
tgatttaaaa ataatgatgt attatgattt agtttatatt tgttttttat ttaatgtatt   21420
ttttaagtaa ttatgttttt gtggttgatt gaatttttt  ataattttt  gttgggaaat   21480 aaagattttt ttttaaattg aagaagtggt tttgttaatt aggggtatcg tatttaattt   21540
gagagaaaaa gattaggaat gataggaatg atagtatatt tttaatattt aatagtttgt   21600
tatatatgtg aaagtaggat atatagtagg gaagtataac gttgagttga tttaaaatat   21660
taaatgtatt tgatatatta ttttttgaat tttatataatt ttagtttttt taaaggtttt   21720 tggatttttta gaagttataa gggtagtttt tggtaaaggt ggtttatttt ttaatttagt   21780
tatagagtta gtggaatgat ttttatatttt aaatgttata ggggaattta ttgagaggaa   21840
aaagggtatt taaattttttt tggatgtttt aattaaaaat ttggattaat aaaattttt   21900 taagtgtttt aaatttaagg aaagtaaata gtatttatt  taattatatt tttaattagt   21960
atttattata gatataattt aaattagtaa tttggtatta gatgaattag atttattgtt   22020
atattatata attttatgt  ttattttgtt gtgtttggga tttttttttt tttataataa   22080
agaatatgat ttataggtgt tatattttga ttttgagaa  attaatgtta tagaaaagtt   22140
gtttggaaag atataattgt gatttgtta  ttgttttgt  tgttattatt ttttttatg    22200 gggatgggta tatattttt  gagatttatt agatttattt tgtagtttat aaattattt    22260 tttagatgta tttaatttgt tgtttagttt gttttttgta aaaaaattta gtgaatatat   22320
ttttaaaaat attttatgg  tttttttta  ggtttgtgtg tatattttt  tcgtgtgtgg   22380 ttttttaatt ttattttgt  tttttttgtg tttgttttaa gtatatttat ttagttttt    22440 ttatattgtt ttgtagtttt atattttag  attttaatt  tgttgttgtg gttattttt    22500 attgtgtttt gttttttat  gtagtttata atttttttt  tttttttgag atggagttgc   22560
gttttgttgt ttaggttgga gtgtagtggt acgattttgg tttattgtaa ttttttgtttt  22620 ttgggtttag gcgattttt  tgtttagttt tttcgaatag ttgggattat aggtgtttat   22680
tattatgttt agttaatttt tgtatttta  gtagaaaagg ggtttcgtta tgttagttag   22740 gttggttttta aattttgat  tttaagtgat ttgtttgttt gagtttttta atgtgttggg   22800
attataggta tgagttatcg tatttcgttt gtagtttata atttttggtg atttttttt    22860
```

```
ttagaatttt tgtattttg tggagtaatt ttgtatttt ttggagttta gggattttaa      22920
atttttaggt tagttttat tttatttat ttttttgttt tgaggttttt atattataga      22980
tgtagtaaat atttagaatt tatattttgt aaggttgaag ttttgattta ttttatttaa   23040
gaaattattt tttttattt ttttttaaa ggttttatta taggataggt tttttgttg      23100
aatttgatgg tgggtcgagt ttttttattt tttttaat aaatgtgata aatttttag       23160
atttttttt ttgtggattg tttttgttt ttgttttg tttatcgtta taaaagaaga         23220
taatgataat aaaacgataa taatataaat gtaaacgtat tttttttt taatttttt       23280
atattattaa ttttttatga attaaggtgt gatatttgaa agttatattt gttttattag    23340
ttatatttat atagtttttt tgttttattg atgtatttt tatattattt tttatattta    23400
tttttttagg tttttttta ttttatgtta gttagatt ttttggtttt ttatttggag       23460
cgttatagta gttttaagt tgttatttaa ttttattt tgtttatttt gtttgttaga        23520
aatttgaagt agatgtgttg ttgtaatgat attatatgtg ttattttg ttttgggggt      23580
tttaaggttt ttaaggttat taaaatattg taataattaa ttgttttaat tgtattttgt    23640
atttattttt ttgttttgt taatttaaaa tgttttaata ttttgttaat attgaatgtt    23700
gatgttttt tatttttt ttttatat gttcgtttat aattgtttat tgattatatt         23760
agtttttaa tattaaaggt attagttata attttgatgt tatatagaat gataattaaa    23820
aggtgataaa tgttaatgat ttaatcgagg agttgtttat ttttataagt ttatttgagt   23880
ttagagaatt ggtaaaagat tggtgatttt tggttattat ttaaatataa ttggttaatg   23940
tagttttgg agattagtgg ttagtataat atttttagtt gagtagggtt aaaaataatt    24000
atatttgttt aagttgtaga tattatttta ttgtatagta aagaatgtta aaatgtttta    24060
atttagtata tgaagagtaa aatataaaaa taggtttttt tttattttta ttagtaagta   24120
aagtggtttg tattttgaa atatattttt tgtttaatta taataaaata taatataaat     24180
gttattaaaa gttttatttt atggatgaag atagtgatat ttagagatat taattagttt   24240
ttttaagatt atatatttat ttagtagtaa aagtaagttt ttataagttg atttattta    24300
ttttagtttt tattggaat tattaaattt atattttt tagtaaaatt atcgtttata      24360
ttttagggt tttaagagtt taatgttaaa tttgggagat ttattttaa attttttaa      24420
agtgtaatat atttttta ggatgattat aaagttatta gatgtgtgtt aagtaatata     24480
tatagttata tatttgat taaaaagat tttaggtta tatagaagag agatttatgg       24540
ttgagaaaaa ggtagattgt ttttaagaaa ggtttaaat atattttt ttgataggtt      24600
ataggagagt tagttagatg aattattata gtgtgtataa aatgtttagt agaataattt   24660
tttagtattg gtagggaaga gtaataggag taatataaga gaaggaaagt tggtttgtag   24720
agtttgtttt agtattcgta ggggtgatga ggttgtttgg gttaagaatt tttttatatg   24780
ttttttggg ataatttatt tagaattatt tttgtgtttt ttaggttatt taggtaatta    24840
ttattaatta gtaaatatag ataaaataga atattttgtt tggatttgtt tgttaaaaat   24900
taaatgatta taatttataa ttttaggaag attttgttatt aaatgaattt atgataaatg  24960
atttaaatga ttttataaa gtagagtttg ttgtaatttt tagtatgaga agtatgaatt    25020
ttattattat ttttaaata ttttgagtta aatggatcgt tttgtaaagt ttatgtttta    25080
tttttataga tagtttaaaa atagtttagt atttagtttg taggttggtt ttatttaagg   25140
agtttgaagt taggtaaggt gtttattatt atttattag atttgttttt tggatatttt    25200
agttgttttt ttttttacg gttagggagg agagttatgt gtatagttta agaatgtgta    25260
```

```
ttttatgtt tttgaatagt tggttataga attggagtta ggtgttttt gtgttattgg    25320 ttttttttt tggtatgttt ttcgggtggt tggagttagt tagtgtttga tttagtttta   25380
tagatttagt aatgaaattt ggagggtaga gtaggtaatt aggtatataa gaattgtaaa   25440
gtaatgttta tttggatagt tgattataat tataattttt taataatgta ataggaatat   25500
aaattgttag attttttata ttattgtaat ataagaaga taattgaagg tcgtgaagat    25560
agtttatgaa atgtaaggaa gaattggata attaagtaat aggaagagta gagaaatagt   25620
gagattttgg gagttataag atttgggtgt ttaaattttg ttaggatttt tttgttattt   25680
ttatttttgt tttttttttt cggttagttt tttttttgttt tttttttatag attagttttt  25740 ttttatatgg atatgaaacg tttttaagtt ttatatttta ggggttttgt tattgaagga   25800
ggattagttt gatattttt tagatttata ttttaaggaa gatgaattat tagatttaag    25860
taatttcgtg taattggaga agatttgtag atttttattta atgggttaag ttggatatgt  25920
atttgtggga gggagatatg ttttgtgggt ataatatata tgtaagtaaa ttttaatatt   25980
gtataagata cgttttgaa aatttatttg tagtttgaaa atttggaagt taaatagtag    26040
attaattgtt gtgagtgtta gaattagtg taatggtatt ttttgtgatt taggtaattt    26100
tgtataggta gaaagatttt tgaaagtttt atttaggttg gaaagggttt gtgttagagg   26160
ttatgagtgg gatttttag gtatttgttt ttttattta aggtttgtat atggattgga    26220
ataaaagttt tggtagttgt aatttttaaa ttttttta agggtattta gggatttaaa    26280
gtagtaggga atgtattttt ttatttttt tgttttttt ttttattgta gtaagaggta    26340
agtatagttt ttagttttgt ttgtatttt ataggagatt tatgtatagg tttcgggttt   26400
tggttgtagg atagtgtgag gttgttgata gggcgagaga atggcgagaa taatggaata   26460
ggattgaggg agaaggaaga ggaatcgttt ttagaattat tatttgggac ggtggtttta   26520
gggagtaaaa aatatttttg gagttttttt aaggggtttt ttggtagagc ggtattatcg   26580
ttagatattg ttatggttgt aggtaggatt gattaaagaa ttttgatt tttttgagga    26640 tagggtaaag ttttgaattg ttttttagaga ttgtatttag atttatattt cggaattatt  26700
attttggttg tattgtgaac ggtaacgttt agggagtagg attggaggga aggagattat   26760
tacgtggttg ttgttttgt ttaagtaggg aataatgatg gcggaacgtt tgtattggta   26820
gagaggagag agaggaggga tttggcgaat ttttggaggt attggtagga tttggtaata   26880
tattgaatgt ggagagtaaa tgggtaggga gttagtgata aagtttaggt gtttggtttt   26940
gatgattggt tatgttgtg tcggttgtgt atagaattta gaggtttagc gttttatgt    27000 gtagcgtcgg tttttatttc gcggtagttt ggtgtggagt tgagatgtgt ttttttatt   27060 ttatgtttac gtttttttag ttagagtaaa gtatgtttgg ataatttagg ttttttttt   27120 ttttttttt tttttttag agagagaggg ttttcgtttt gttatttaga agaagtgtag   27180
tgtcgtgatt atagtttatt gtagtttga atttttggtt ttaagtgatt agaggattag   27240
gtgtattttt ttataaattt tttaaatttt tttagtatt ttattttta agggatttta   27300 tagtttttt tatttggacg gcgttatggt gtttatttt attttgaga attgttttaa    27360 aatttatat agaaatttgt tattatgtat ttaaatgaga agaaatgttg aatttgtaat   27420
tttaattttt taagataaga gtttgtagtt cgttttagt agagttaaag aaaaagatat   27480
gatgaatggt ttatatattg aaaattgtag aagaaataat ttaatatgga atgggtgagg   27540
ttgttatagg tggtgtaaaa ataattgcgg ttttgttgt tattttagt ggtaaaaatc    27600 gtaattgttt ttgtataaat ttaataatat tgtttgaaat ttatattttt tggtggaata   27660
```

```
gttttgagat agagcgggaa ttagattatt ggtttataaa atagtatgta gttattgtta   27720
ttttttaatt ttatatttt attatgaggt aatgttttt ttatttgatt tggagaatgt     27780
ttttatttt tttttatata tttgtgaaaa ttaaatgtta aaggaattaa tataataatt    27840
attgttaaat tatgatgtaa aataatattg tgtttgtaat tagtttaggt agttttattt   27900
ggtttaataa tataaaatta ttaggtttat aatattttag tattttagtg tgattggtta   27960
agaaaaaaat ttacgttatt ataaaaagtt aaattaagta ataattaatt taaattttaa   28020
ggaaatataa agtaaagtat tatgttgtaa tatggaatat taatgtaaat aattttttaa   28080
tagtttatga aatagatttt gaattggtag ttgataaaga aaggttagtt ttggtttaat   28140
tttttttatgt tttaatattt tttttgaagt tttatttaat tttatttgcg ttagtaatag  28200
tattttgaga tggtggtgta tttggaaaat tattattttt tttttgataa ttagtatttt   28260
taatttaatt tttatatatg tttttggaa atattatatt tatattttga tgacgtttta   28320
aaaataattt taatgtaata attatatatg tgtggtgagt aaattgtgtt tcgtaaaaga   28380
tatttttaaa ttttaatgtt tgtatttggg aatgtgattt tatttggaaa tagggttttt   28440
gtaggtatga ttaagttaaa atgagatttt attggattag gatgggtttt aatataatga   28500
ttgttgtatt taagaggaaa atttgtatag agatatatat atatataaaa gaatgttatg   28560
taacgttagg tacggagaat attatgtgat aatgaaggta gagattggag tgatgtatt    28620
atgagttaag gatggttagt aattttttaga agttgggag agataaagga tgtttttta    28680
ggattttag agtaagtata aatttgttag tattttgatt taggattttt ttttttaga    28740
attgtgagaa tagattttag ttttaagtta tttagtttgt ggtattttgt tataggagtt   28800
ttaggaaatt aatgtaatat gttatgttgt aaataaatag tagttttaat tggtataat    28860
aataatttta agtatatttt attattaggt taggtgagta ggaaattgtt tggtagatta   28920
attattaatg ttgtattttt tgaaaagtta aaatatttt atttagtaaa taatatttgt    28980
ttaaaagttt ttatttgtat tgtttaaaa taaagtaaaa attaaaatgg agttagttat    29040
gtatttgaaa aatgtgaaaa aggaaagaaa aatttttag gaaagatttt ttttaaaatg    29100
gttatatatt tgagaaagaa ttttaaaatt taaattattt ggttgtttat tttatttttt   29160
tgtttatatt attagatata ttatgtatga ttttatatat tatgtatgtt atatttaatt   29220
aatatttatt aaatatttaa aatttgttag gtttgagtt aggtattgta gataggtaaa    29280
taagataaat atttttttt tttaaagaga ttattttggt atgaaattta atttgtagaa    29340
gaagtgaaag aggttatttg tagagtttat tatgaaaatt tattttatt atttgttgta    29400
gttttatttg attttgtgaa attatttag tattatttgg ttttatttg tgttttgta     29460
ttatattgga gaaaataaaa tttatttatt gtatagaata tataaaatta attaaagtat   29520
gtgaaattaa aaatgtaatt gtttattaaa ttttttttag tgtttttat ttattagtat    29580
ttaaatatat tttagttgt gtatttatgt tagtataatt aaaatgtggt gtttttattt    29640
ttttatttaa tttataatta ataatgttta ttttttatt ttttttttt gagatagagt     29700
tttatttgt tatatttagg ttggagtgta gtggtatgat tttggtatat tgtaattttc    29760
gttttttggg tttaagcgat ttttttgttt tagtttttg agtaattggg attataggcg    29820
ttcgttatta tgttcggtta attttttgta ttttagtaga gatagggttt tattatgttg   29880
gttaggttgg tttcgaattt ttgattttag gtgattcgtt tatttcggtt ttttaaagtg   29940
ttgggattat aggtatgaat tattacgttt ggtttttttat tatttttata att          29993
```

<210> SEQ ID NO 3

<211> LENGTH: 29993
<212> TYPE: DNA
<213> ORGANISM: Artificial Sequence
<220> FEATURE:
<223> OTHER INFORMATION: chemically treated genomic DNA (Homo sapiens)

<400> SEQUENCE: 3

```
aattataaaa atgatgaggg gttaggcgtg gtggtttatg tttgtaattt tagtattttg      60
ggaggtcgag gtgggcggat tatttgaggt taggagttcg agattagttt gattaatatg     120
gtgaaatttt gttttattaa aaatataaaa aattagtcgg gtatggtggc gggcgtttgt     180
aattttaatt atttaggagg ttgaggtagg agaatcgttt gaatttagga ggcggaggtt     240
gtagtgtgtt aagattatgt tattgtattt tagtttgggt gtgatagagt gagattttgt     300
tttaaaaaaa aaaagtggaa aagtgaatat tgttgattgt gaattagatg aaaaaataag     360
aatattatat tttagttatg ttaatatgga tgtataatta agaatgtatt tggatattga     420
tgaatgggaa atattaaaaa aaatttgata aataattata tttttggttt tatatatttt     480
aattaatttt atgttgtttg tgtaataagt aaattttatt ttttttaata taatatagaa     540
gtataaagta aaattaaatg atgttaaaat ggttttatag gattaggtaa aattatagta     600
gatagtgaaa atgaatttt atggtagatt ttgtaaatgg ttttttttat ttttttata     660
gattaaattt tatgttaaaa taatttttt aggggaaggg aatgtttgtt ttatttattt     720
atttataata tttagtttaa ggtttagtaa attttaggta tttaataaat attgattgaa     780
tgtaatatat ataatgtatg aaattatata taatgtattt gataatgtaa ataaaaaaat     840
ggataaaata gttagatgat ttaagtttta aaattttttt ttaaatgtat agttatttta     900
ggaaaaattt tttttaaaag attttttttt ttttttttat attttttagg tatataattg     960
attttatttt aattttttgtt ttgttttagg ataatataga tagaaatttt tagataagta    1020
ttattattg aatgggaata ttttaatttt ttagaaaata taatattgat aattagttta    1080
ttaggtaatt ttttatttat ttgatttaat aataaaatat atttaaaatt attatttata    1140
ttaattagaa ttattgttta tttataatat agtatgttgt attagttttt taggattttt    1200
ataataaagt attataaatt gggtggttta gaattgaaat ttatttttat agttttggag    1260
gaaagaagtt ttaaattaag gtgttggtag atttatgttt gttttggaga ttttagggaa    1320
gtattttttg tttttttta gttttggggg ttgttggtt ttttggtt tatagatgta    1380
ttattttaat ttttgttttt attgttatat gatgttttc gtgtttaacg ttatatggta    1440
tttttttgtg tgtgtgtatg ttttttgtata aattttttt ttaagtataa tagttattgt    1500
attaggattt attttaattt agtaaaattt tattttaatt tgattatatt tgtaaagatt    1560
ttgttttaa atgaggttat attttaaat atagatatta ggatttaaaa gtattttta    1620
cggaatataa tttatttatt atatatgtat aattattata ttgaaattat tttaagacg    1680
ttattaaagt atgaatgtaa tattttaga aagtatatg aagaattaaa ttaaagatat    1740
tgattgttag gaaagaagtg ataatttttt agatgtatta ttatttaga gtattgttgt    1800
taacgtaagt gaaattaaat aagatttag gaaagatatt ggagtataag agaattaagt    1860
taaaattagt ttttttttgt taattgttag tttagaattt attttatgaa ttgttgggga    1920
gttatttata ttaatgtttt atgttataat ataatatttt gttttatatt ttttttgaaat   1980
ttagattaat tgttatttgg tttgatttt tatggtaacg tgaattttt ttttggttaa    2040
ttatattaag gtattaaaat attatgagtt tagtgatttt atattattga attaagtaaa    2100
attatttagg ttaattgtag atatagtatt attttatatt ataatttagt aatggttgtt    2160
```

```
atgttaattt ttttaatatt tagttttat  aaatatatga gaaaaagatg agaatatttt   2220
ttaaattaag taagagaagt attattttat aataaagata taagattaag gaataatagt   2280
aattgtatgt tgttttatga gttaataatt tagttttcgt tttattttaa gattgtttta   2340
ttagaaaata tgaattttaa atagtattat taggtttgtg taaaaataat tgcggttttt   2400
gttattgaaa gtaatagtaa aaatcgtaat tattttgta  ttatttgtag taattttatt   2460
tattttatat tagattattt tttttgtagt tttaatata  tagattattt attatatttt   2520 ttttttaat  tttgttagaa gcgagttata aattttgtt  ttagaaaatt agaattataa   2580
atttaatatt tttttttatt taaatatata atagtaagtt tttatataaa gttttaagat   2640
aatttttaga aatggaatga ggtattatgg cgtcgtttag gtgggagaga ttgtaaggtt   2700
ttttaaggaa tgagatgttg aaggaggttt gagaagtttg tagagaagta tatttaatt    2760 tttgattatt tgaggttagg agtttaaggt tgtagtgagt tatgattacg atattgtatt   2820 tttttaggt  gatagagcgg agatttttt  ttttagaaa  aaagaaagaa agaaagaaag   2880
aaatttaggt tgtttaggta tgttttgttt tggttaaaga aacgtgaata tggagtggag   2940
ggggtatatt ttaattttat attaggttgt cgcggaatga ggatcgacgt tgtatatgga   3000
aacgttaaat ttttggattt tgtatataat cggtataggt atagttagtt attaaagtta   3060
aatatttagg ttttgttatt gattttttgt ttatttgttt tttatattta atatattatt   3120
aagttttatt aatattttta aaagttcgtt aaattttttt tttttttttt ttttgttagt   3180
ataggcgttt cgttattatt gttttttgtt tgggtaggag taatagttac gtaatggttt   3240
tttttttttt agttttgttt tttggacgtt atcgtttata gtgtaattag agtgatggtt   3300
tcgaaatata gatttgaatg tagttttaa  aaataattta gagttttatt ttgtttttag   3360
aagaaattag aaatttttta attagtttta tttgtagtta tggtagtgtt tagcggtagt   3420
atcgttttgt taaaaggttt tttgaagggg tttagggt   gttttttgtt tttggatt    3480 atcgttttaa gtagtagttt tggggacgat tttttttttt tttttttag  ttttgttta   3540 ttgttttcgt tattttttcg ttttgttagt agttttatat tgttttgtag ttagagttcg   3600
ggatttgtat atgagttttt tgtgagggta taagtagggt tgagggttat atttgttttt   3660
tgttgtagtg aaaaggaaaa taagggaaag tggggagta  tattttttat tgttttaaat   3720
ttttagatat ttttgggaaa agatttaaaa attgtagttg ttaaaatttt tgttttagtt   3780
tatgtgtaga ttttgggatg gggaaatagg tgtttgaaga gttttattta tgattttga   3840 tatagatttt tttaatttg  ggtggggttt taagaatttt ttttgtttat gtagagttgt   3900
ttgggttata gaaagtgtta ttatattaaa tttaatatt  tataatagtt ggtttattgt   3960 ttggtttta  gattttaaa  ttgtaagtaa attttagaa  gcgtattttg tataatatta   4020
aggtttgttt gtatgtgtat tatatttata aaatatattt ttttttata  gatgtatatt   4080 tagtttaatt tattaggtag ggtttgtaag ttttttttag ttgtacgaaa ttatttggat   4140
ttaatgattt atttttttta ggatatgagt ttgggaaaat attaggttag tttttttta    4200 gtggtaaaat tttaggata  taaaatttgg aaacgtttta tatttatgtg gaaaaagtt    4260 ggtttgtagg gaaagataga agagaattga tcgagaaaga ggagtaaaaa tgaagatggt   4320
aagaagtttt tggtagaatt taagtatta  gatttgtga  tttttaaagt tttattgttt   4380
ttttgttttt tttgttgttt agttgtttaa ttttttttg  tattttatga gttattttta   4440
cggtttttaa ttattttttt tatattgtaa tggtataggg agtttaatag tttatatttt   4500
tgttatatta ttgagaagtt atagttgtga ttaattgttt agatgggtat tgttttataa   4560
```

```
tttttgtgta tttagttatt tattttgttt tttaaatttt attattgggt tgtgaagtt    4620 ggattaggta ttggttggtt ttaattattc gggaagtatg ttagagagga aagttaatgg   4680
tataaagaat atttagtttt aattttatgg ttaattgttt agagatatgg agatgtatat   4740
ttttggatta tgtatatgat ttttttttt ggtcgtagaa aagaaaaata gttgaggtgt    4800
ttaagaaata gatttggatg aatagtaatg agtattttgt ttgattttaa gttttttaaa   4860
tggagttaat ttataaatta gatgttgagt tattttgag ttgtttataa agatagaata   4920
tggattttgt aaaacggttt atttaattta aaatgtttaa aaaatgataa tggggtttat  4980
attttttatg ttaaaagtta taataagttt tattttgtga gaattatttg ggttatttgt  5040
tataagttta tttgatggta agttttttg gaattataaa ttatgattat ttgattttg   5100 ataagtaggt ttaaataagg tgttttattt tgtttgtgtt tgttaattgg tgatggttgt  5160
ttagatagtt tagaaaatat agaagtaatt ttgagtgaat tgttttaggg agatatgtga  5220
aagaattttt agtttaagta attttattat ttttacggat attaaggtag attttgtaga  5280
ttaatttttt ttttttgtg ttattttat tgtttttttt tattagtatt gagaaattat   5340
tttgttgagt attttgtata tattgtaatg gtttatttag ttggtttttt tgtagtttgt  5400
tagaagagaa tatatttgaa gtttttttta gaagtaattt gtttttttt tagttataaa  5460 ttttttttt gtgtaatttg gaaatttttt ttgattaaga gtatatgatt atatatattg   5520
tttaatatat atttgatgat tttatgatta ttttgaggaa aatgtgttgt attttgagag  5580
aatttaagaa tagattttt aagtttagta ttgaatttt gaattttag aaatgtaaac   5640 gatagttttg ttaaagggaa tgtaagttta gtgattttaa ataagattg gaataaaata  5700 gattagtttg tgaaaatttg ttttttattat tggataaatg tatgattttg gaaaagttaa  5760
ttaatatttt taaatattat tgtttttatt tataaaatag ggtttttaat aatatttgta  5820
ttatattttg ttatgattaa ataaaaaata tattttaaaa atatagatta ttttgtttgt  5880
tagtgagagt ggaagaaaat ttgttttttat attttgtttt ttatatattg aattaaaata  5940
ttttaatatt ttttgttgta tagtagagta gtatttgtaa tttaaataaa tgtaattatt  6000
tttaattttg tttaattaag agtattatat taattattga ttttttaggag ttatattaat  6060 taattatatt tagatagtag ttaaaagtta ttagttttttt attaattttt tgaatttagg  6120
taagtttgta aaaatgaata attttttcgat taagttatta gtatttgtta ttttttagtt  6180
gttattttgt ataatattaa agttgtgatt ggtgttttta gtgttgagag attgatataa  6240
ttaataaata attatagacg gatatgtgaa agaaagggga ataggaaagt attagtattt  6300
agtattaata ggatgttaag atattttaag ttggtaaaag taggagaata agtataaaat  6360
ataattaaga taattggtta ttataatatt ttgataattt taaagttttt aaaattttta  6420
aaataaagaa tggtatatgt gatattattg taataatata tttattttag attttttgata  6480 aataagatga ataagaagtg gagttaagtg gtaatttaaa ggttgttgtg acgttttaag  6540
tgagaagtta agagaattta gattgatatg gggtggaaaa aggtttggag aagtggatat  6600
gagggataat atgagagata tattaataag ataaggaat tatatgaata taattgataa   6660
ggtaaatgtg atttttaggt attatatttt aatttatgag aaattgatga tatggaaaag  6720
ttaagaggaa aagtacgtt tatatttgtg ttgttatcgt tttgttgtta ttatttttttt   6780 ttatggcgat gggtaggaag taaaagtaag aggtaattta tagaggaagg agtttaaaaa  6840
gtttgttata tttattggag gggggataga aaaattcggt ttattattag atttagtaaa  6900
gaagtttgtt ttatgatgga gtttttggga agagaataaa agaaaataat tttttgagtg  6960
```

```
agataaatta aaattttagt tttgtaggat gtaaatttta aatgtttatt gtatttgtgg     7020 tatgaaatt ttaagataaa aaaataaaat aaaataaaga ttgatttaga ggtttgaaat      7080
ttttagattt taggggaatg taaaattgtt ttatagagta taaagggttt taagagagaa    7140
atttattaaa agttataaat tataggcgag gtgcggtggt ttatgtttgt aattttagta    7200
tattgggagg tttaggtagg tagattattt gaggttagga gtttgaggtt agtttggtta    7260
atatggcgaa atttttttt tattaaaaat ataaaagtta gttgggtatg gtggtgggta     7320
tttgtgattt tagttattcg ggaggttgag gtaggagaat cgtttgaatt taggaggtag    7380
agattgtagt aagttaagat cgtgttattg tattttagtt tgggtaatag agtataattt    7440
tattttaaaa agaaaaaaaa aattataagt tatataaaga aataaaatat agtagagagt    7500
agttataata ataaattagg aatttaagaa tgtgaaatta tagagtaatg tggaaaaaat    7560
tagataggta tatttaaaat agatataaaa gaaatagaaa taaaattgaa aagttatata    7620
cgaaaaaaat atatatataa atttggaaga gaattataaa aatgttttta aaaatatatt    7680
tattgaattt ttttataaga aataaattaa atagtaaatt agatatattt aaagaaataa    7740
tttatgaatt ataaggtaaa tttggtaaat tttaagaagt gtgtgtttat ttttataaaa    7800
gaaaataatg ataataaaa taataataaa attataatta tattttttta aataattttt     7860
ttataatatt aatttttag gaattaaggt gtgatatttg tgagttatat tttttattat    7920
ggggagggag aagttttaaa tataataaag taaatatgag agttatataa tatggtaata    7980
aatttgattt atttaatgtt aagttattga tttgaattgt gtttatagtg aatattaatt    8040
aagaatgtaa ttaaataaga tgttgtttgt ttttttttaaa tttgggatat ttgaggaaat   8100
tttattgatt tagatttta attgaggtat ttaggaaagt ttgagtatttt tttttttttt    8160 taataaattt ttttgtagta tttgaatata aaaattattt tattgatttt gtaattgaat    8220
tagaagtagg gttattttta ttaaaaattg ttttttatagt ttttaaaaat ttaaagattt   8280
ttaaaagggt tgaagttgta agaatttaga aaataatgta ttaaatatat ttggtgtttt    8340 gagttaatt aacgttatgt ttttttgtta tgtgttttgt ttttatatgt atggtaggtt     8400
gttagatatt aggagtatgt tgttattttt gttattttta attttttttt tttaagttaa    8460
gtacggtgtt tttggttaat aagattattt ttttaattta aaaaaaaatt tttgtttttt    8520
aatagggaat tataagggaa tttagttagt tataaaagta taattgttta ggaaatgtat    8580
taagtggaag gtagatataa attaggttat agtgtattat tattttttaaa ttatttaatt   8640 ataaattgac gtattaatat agattaatat taatgtatat taaagtatta tatttatatt    8700
taaataaaaa tgtaaaggaa aattaattag ttgaaataga aattaatgat gataattttt    8760
aaagtagtaa gaatgtattt ttgagaaaga tttttagggtt ttgtttgttt gtttgttgga   8820
gattaaatta tttttttagta aaattgaagg gggaaaaaag attaacgttt aagttatagg   8880
aagatgtggt ttgtttggta tttggatgtt ttttgtagaa tttataagtt tattttttag    8940
gggtttaaat gttttggat ttaaaaagtt ttcgggaaag aatttttta agggaagaga      9000 tggagagtta tataagtaga aattaagttt gagttttaag ttttgggtt gtaagaaaag     9060 aataagagaa taagttaaaa aagttgttta ttaaattttt tatagaaggg gaggagggta    9120
ggtgttatta ttacgtattt tgaagttttt gttataggtt attggattga gggaagttgt    9180
tagatatttt ttttatttta aattatttgt aattttagta gttcgattaa aaaatataat    9240
ttcgtaagtt gatggaaaga aacgaatttg tgaagaaag cgcgggaaaa tattggttaa     9300
attagtaaga aaaagatcgt aataaaaaag aatttaaagc gtgagaattg aaattaggaa    9360
```

```
gatggtagaa tgagaagtag aataaatttgt ttttttttt ttgattgaat taaatgtaaa    9420
gatattaggt ggtagagatg tggatattag tttttatagt attttttaag agtgttatgg    9480 tttttttcg tttttatttt atgttttagg tattttttt agggttttag ttaagttttt    9540
gtttaagtat ttgaataaat tagatttatt tttgaattag ttttaggtgt tgtttataga    9600
tattgttatg gtttatattt ggataattta gtttggtttt tttaatgttt taattttttt    9660
tttatgatcg tgaaaaaaat gtaatgagtt ttttttgaaga aatatttaag atatataaat    9720
ttagaatatt tatagttttt aaattaagat tgtattatat aaaaatatcg attttttttaa    9780 aatgtatgaa tgagtgaatg agtgtataaa tagttaatag tgtataaatg tatgtatgaa    9840
tgaatgaatg agagtataaa taagtaaata aggaaatata tttttaaagt atatgttagg    9900
aaatggataa aattcgtttt atgaagtttt agattgaatt aggtaaatag aattgtagat    9960
ttttatgttt gttatgattt agtgtatagt tttgggaaaa ttttgtaatt tttttatatt   10020
ttagtttttt attttataaa aggagtatat tgtttgaaat ttaatttttt tatagtagtg   10080
agagttttga tttaacgttt ataaaacgtt tttagttttt tttgattaat aggtaaaata   10140
ttgtggtagt ttgtataata tatttttaa aaaggataaa ggtaattggt cgaatttgat   10200 gtaaataat attttatta agaaataaat attagttata tttattattt ttttatttta   10260
tttgttaagt aataaaaatt attttaata gaaaagtatt aaattaatat ttaagttagt   10320
tgaagtgtta ttattatagg ttttatttac gttgggggaa ggagagttgt tttgttttt   10380 taggttattt tatatgttta tatggtaaag ttaggaatgt tgggtatagt tttgaaggtt   10440
tttagcgtat ttattggttt ttggtatttt aatgtatttt attttataa ttataaagt   10500 attttgagt gttttggaa atatataata aattttaat taattaaga gtgttttaat   10560 tgtatatatg aaattttttg ggaggaaaat attagttatt ttatatatat atagtattta   10620
agttagtaag agagttttt ttgaaaggta taaagtagtt tttttatagt aatataattt   10680
ttagttttat atgtgtaagt tttattgaat tttttagaat aataggaaat tttgtaggaa   10740
aaaaaatttt ataaaaattg atagttatat ttatttaatg taagaggaat atattagtta   10800
ttttgagttg gattattttt taaaggtatt agataattat tgaagattaa ttaaaatttt   10860
aattaaaaat tataagaatt gaatattttg gagatagaat ttttttatata taaaaatcga   10920 ataataaaat taattgatta atatattta ttttaaaatt gtatttatta gattatttta   10980
gttagtattt gagtagtaat ttttttggatt ttgatgtatt aattttttatt ttatatttaa   11040 atagattata ataagtaata gatttataaa ttagttattg atatgatata attgatattg   11100
tgatatgtat aataatattt attaatatat ttataatgga gtaatgttat ttattattta   11160
tataatgttt atatttttta ttttatgtt aaaaagttat cgtaatatat gtaaggtgtt   11220
tagaattgtg tttggtatag agtaggtttt tattagaata ataatatatt atttttata   11280 agttttatt aattatatga gagttagaat tatttttttt aataaatttg gtaaatattt   11340
gatggtatta agtaaaaaaa aatgtagtga atataatatt attgatttat ttttttttaa   11400
tatttgggtt tacgaattat aagtaaatat aatatgtatt tataaaaatg aatattaaat   11460 attttaagt gagaaattaa ttatataaat tatatgtata tattaaatat atatcgttaa   11520
tagaattatt tatttttaatt atagtggagt atttcgatta ttatatgagt tttaaggaat   11580
ttattattat aattattttt tttaattaga gtataaataa ttataaggtt taattaagtt   11640 gaaattttttg tatttggttt ttgtgagaaa gatgagaata ttattttaaa gatgtaagat   11700
ttataaattt ttttaaaaag tatttggta tttttttatgg aaaatgtata tatatattta   11760
```

```
tttattaata ttgtatttag agttttattt atagatattt ttggtagatg tacgaagaga   11820
tataaaaatt attagtgtaa tatatttagt aatagtaaaa atatggaagt aatgtaaata   11880
tatattaaga ggggaatagt gaaattatga aatatttgta tatattaaat agaagtattt   11940
aaaattatat gtattgatgt ggaaaaatat ttaagattta gtagattaaa agtaagtttt   12000
aaggaaatta atgattttat tggagttaaa aatgtaaaat gaaaataaat tatattttta   12060
tatagttatt atatttatat atatatgaaa aaaaaaatgt ttgaaaagat gtatatttaa   12120
gtataataat ttattttgat ttgtagagaa taagaatgag taaatttatt ttttatttta   12180
aatatattcg tattttttaaa attttttaag aaagtatat atatgtatag taaaataaaa   12240
tatataaatt aaaagttgat tattgatgaa ttttttattga ataaatatttt ttatatgatt   12300 agtaattaaa ttaagataaa agatataatt agtattttaa agttttttt ttgttttttt   12360 tggttatttt ttttaaaagt aattttttatt attttttgttt taatatgtta tataaagtat   12420
gatttatttg tattttttaa gtaatagatt aaaaaaaaaa atttgtttta gtagtatgaa   12480
tttttttttt tgaatattaa atatatttag tatttttattt taagatatta attttaaatta   12540 taatttgagt tttttatagtg ggttaggtat tgaattaaat gttttttttg tatgaattta   12600
attatttttt ataattttat gaggcgagta ttgttattat ttttttatgta tatatgttgg   12660 aattatggtt tatagttatt tagaaaatta tatgattaaa gttatatcgt tgatgagtgg   12720
tagagtttgg atatatataa aggtagtttg attttagtat ttttaatttt ttattagaaa   12780
taaataaata aaaataaagt ggtaagatgt agagttggga gtatgaagtg ttttttagtat   12840 gaagtttttt tttttttgttt tgttttgagt aaatgatttta aggttttaag gttatataat   12900
ataatatttt atttgtaaaa tggaagggtt aggttagatt tttttttttga tttgattatt   12960 tgacgttgat aaataaagtg atttattgaa atatagagta aatatgtttt gttatgatgt   13020
agtgtaatta tgtattgtat tatgttaaaa aatgatttat ataagaaaat aaaattataa   13080
tttttgaaat tattggaaat aataattttta atttaatgtt attttttggat ataggaagat   13140 ttttttttttt aaataagtaa attggtggtt tttgaagggt tttgtttatt tttgtatgga   13200
aaatgtttaa aaataaatta ttaaaaatta aataaaattt ttttatttt ttaattgtgt   13260 ttgaaaaaaa agatgtaatt tttttttagta aaaggttacg tatattttta atagatatat   13320
ttgggatttt tggttttttat attttgaaat attgatataa ataaatatag aatatgttttt   13380 tttttaaatg aaatttataa ttttgagggt taaaaatttt ttaaaataat atgaaatcga   13440
ttttagtaga aggtaattaa agagattaag gtttgttttt ggagaaaatt agaattatga   13500
agattataaa ttttaacgag aaatttgttt tttaaatgtt agtttattga aaatattaat   13560
gtacgtcgga tatatttgtt tttttattag aaaattagta atattttggt ataaatgagg   13620
ttttaaataa gttggagtag aaaataatta ataaattagt ttttatgatt ataagtaaaa   13680
gagaattagt tttttaaaaa gttaatagga tttatttttt gtagatgttt ggtttgggat   13740
ttaatgtttt ttaaagatat gtatggaata gtgtagttat ttaattttta ttaatatttt   13800
taggtgttga ggttacggag ggaaaaagat atgattttt tttttgttga gtttatagtt   13860
tttttagaag atagatatat ataatgagtt ttaatataat ttgttgttat attaatagtt   13920
taaaaaaagt gttatggtat tatatagaga aaagaattaa ttttgtttga gttttaagga   13980
aggttttata gaggaggtga tatttgagtt aagttttgaa agatgagtag attattatta   14040
ttattattat tttgtttagg taggtagtaa aagagtatta ggtaagtagg ttaagggagt   14100
tggggttatg gaggataagg gtggtgagaa tatgttaggg agaaaaaagg aagtgattga   14160
```

```
cggtattata agaaataaaa tgtttataag taagttttat tatattagga tttattatat   14220
aaagaattaa tttgagaaag gagatatgtg atttgaaat  tttgtggggt tttttgattt   14280
atgaatttag gaagtgttta tttggaaaaa tagaatttt  gggttttgg  tcgtttttta   14340
gtaattaaag ggttattagg ttttcgttt  aatatttggt ataaagtgtt tggatggatt   14400
tgtggttcgt tgtgttttt  ttggatttt  tgtttatgaa tgaagtagaa ttttttttta   14460
ttatttgtga tttaaatttt tgttttaaat ttttcgtaat attttcgag  aacggttttt   14520
atttgttatt gggttgttta gtatttattt tatttttg   ttaataagga gttatgtagg   14580
gttttttttt atttaggaaa tagaaaaata ttttggttaa atatagtatg ttgtatttgt   14640
agttttttgt tatttaagta tatattttaa aattaaagta taaattaaag gaagtgagag   14700
agagagagtg agtgtgtgtg tgtgtgtgtg tgtgtgtgtg tgtgtgtgtt              14760
tttaagtatt tttattttgt ttatttaggt attaattagt aaatgatgtg aaattttag    14820
gttagtttga ttgttttat  gattatttat ttaatataat taaagtataa ttattaaatt   14880
agataatgta taagtgtgga attttaagta tttttgtaat ttttaataag ataaaaatta   14940
tttattgttt agaattttta agaaaattag tttaattata tatttataat attaatgttt   15000
tatattttag aataattttg aaatttaatt taaaatttat atgggaaaag ttatttttt    15060
ttatttatg  tgaatattat tgttttatt  ttgtttaagt gattttgaa  atgtgtttta   15120
tatatgttta aattatgtaa gggtggtgtt taaataatag ttaaatttat ttatattaat   15180
tatatattat tttatagata aaatgtattg gttaatatta aatttataga atgagaattt   15240
aaaagtttgg atttgagaat ttataaaga  gagtttttat atgtaatata tttatttta    15300
ttttttttta gttgtataaa tgttattaat ttaagatttt gaatttgtgg ttataattga   15360
aagttatata tatttttt   gaaattttt  tattataaat aaataattta atttattaag   15420
tatttaatt  tttagtagtt gtgattatta gtaattttat tttttttaat attatagatt   15480
aaataaaata aaagttttt  attattgaat atttatttat agaaatggaa aggtaatggt   15540
tattatttaa aaataaattt aaattattta ttgataaaata atcggaagaa aagatatata   15600
gatgattaa  ataaatattt attttttata tattttttt  taggtatttt gttattttta   15660
tttatatatt attttagaa  aaggaaaata tgttggagat ggttaatttg tgtgaagcgt   15720
atttgtaaat tttttttgtg taaagttaat ttattaaatat agattaatga gaattgtttg   15780
attttatgtt taaatttggg aggaaggtat taggatttt  tatatttgat tggaaataga   15840
ataatttttt tatgtagagt tttgggagtt tttttgattat attaaatgat attaagattt   15900
gtttaggtta tgggttttta agaagaggta attttgtttt tagagattat ttgataatgt   15960
ttggagatat tattattatt aggggaggga gggttttgg  tatttagcga tgttattaag   16020
tattttatta ggtataggat agtattttt  gaataaatta tttagtttaa aatgttaata   16080
attagagttt gaaaattttt tatttaaata tattgaagaa tttaggtata acgtattat    16140
ttttaaaatt atatagatat atttggtagt agttttagat aagttgtaaa aatgagattt   16200
tgataattaa tatttaatt  ttttttttt  tttagtttt  attttgtttat atagttatta  16260
tatttgaatt taagtgataa attttgtaag tagaggtatt aattattttt tattgttttt   16320
ttaaaggtaa gaattatagt aatatgtaaa gttattttt  aaaagttta  tattgagttt   16380
attaggttta ttgattattg aaaattatat aaattttat  aattggtatt ttacggttga   16440
aaaaaaagta attgaggaaa tttaaatatt ggttataaag tattattatt atataacgtg   16500
tttataattg tttaaagtag ttaaggaatt atatagatta aagttttaaa ataatttaga   16560
```

```
ttattgtatg cggaaatatt tattaaaaga aatattattg tataacgtaa atggttaatg    16620
ttaattgttg agtatttata gtgttttttt ttaaggtttt aaatataatt ttagatttgt    16680
taagatgatt tatagtattt aatttatatt tggattattg gatattttat ttatggttat    16740
taatttatag ttttttaaaa aagattttta gttttaaata tttttggaat atttgggggt    16800
aatttaatga aagatattta attatagtaa taataattga tatttatatt aagtattatt    16860
ttaaatatat ttatatatat ttatttattg aattttattt agaattttat gaggtatgtt    16920
ttgttatata tgagaaattg aagtaaaatt tgttttagta atgtgtttga tgttataaat    16980
ttattaatgt tagagttgag gtttgaattt aagtgtttgg ttttatattt tttttttttt    17040
ttatttattt atttattttt gagatggagt tttattttgt tgtttaggtt ggagtgtaat    17100
ggtgtaattt tagtttattg taattttttgt tttttgggtt taagtgattt ttttgtttta    17160 gttttttcgag tagttgggat tataggcgtt tattattacg tttagttaat ttttgtattt    17220
ttagtagaga cggggttttg ttattttggt taggttggtt tcgaattttt gattttaggt    17280 gattattcg tttcggtttt ttaaagtgtt gggattataa gtgtgagtta tcgcgtttag    17340
tttttatatt ttttttattt atttattgtg ttataagaat tgagtttttt agattttaag    17400
tattatgaaa ttatcgtatt tttagagatt tttaggattt ttggtttatt tattagatta    17460
ttgatttttt agtggtaaga aataaatata ttttttatatt tacgtatata tatatataat    17520
ttaagtttgg atttatagtt gtaattttat tgggtttata ttaaaatttt ttgaggttgt    17580
tattgaggta gttttatttt gtaatagtta ttgttttttt tattgttttt agttttaagg    17640
aggggatgtt tagtgttata attttttgttt ttattttttag tatttttatt tatttattta    17700
atgggaatat aataattatt tattgattat atgtttagta gtgtattgtg tattagcgat    17760
atagaaatga taaatatagt taattttttt agtaaattttt tagtttaaag taggatttag    17820
attaatgtaa tttattatat tttaatgtgg taagggttat gttaaatgta gaagttggat    17880
gttttgggag taataagaaa gaaacgttta atttagattt tggaggttag aggaatttat    17940
tagaggagtt aatatttttgt attttaagta ttgaaaaagt agtagaaaag atatttgtag    18000
ggggagaggg gcgatgtttt ttagagaaaa agtattttac gtataaagaa atgaagtgga    18060
aatgtttaag gtgtatttga gaattgtagt ttttttatata gttggaaaag agagttgttg    18120
tgagtgggga gtgagagatg agaagagtaa tttgagtaag gtttttagta tgaagggtta    18180
ttttttttgt agagaattttt ggaatttgtt ttataggtag taggtaaatt ttttaaggaa    18240
ttttaagttt aggagggatt ttataaaaat tatgaataaa tgtggttgaa tatttttaggg    18300 acgtgagaga gtgttagaga tagtttttaat atagtttaga atgggttttt aggagaggta    18360
ttaagatatt ataattatat ttgttatgat aatatttaata cgaataagtg tgtataggat    18420
aattgtttat ttaaagttaa tttgaatatt tgaggattag atttgtgatt ttggttataa    18480
tgattttttt tttaaatatt tttgggaatg gtatgtaaaa atataagaat ataataaaag    18540
ttttaaagtt tttaaagtta tgtagagtag aaaagaaatt tatttatttt attttaattt    18600
tgtaagtttt tagtaatatt gataaggaaa aagtatttaa taagtatttta ttaagtattt    18660 ataattttgt taattattttt tatgaacgaa attttttaaaa attaaagtta ataattaagg    18720
gaaaaaatta gatttaaatt aaaatttttt atgagttaat taagaaaaat aatagtatta    18780
ttatttattt aattaaagtt aatgtaaaaa taaataaata aaaaaaaaaa taaaataaaa    18840
tagtagaatt gtcgttttttg ataggttat tgaggtttgt atgtttaagt tatttattag    18900
aagtattgtt ttagattatt ggaaaatttg taaaaggaaa tttgaatgtg atttatttat    18960
```

```
aacgttatta aatttagtaa gaatgatttg agttataatc gtatatgaat atatatttgt  19020
atttaaatgt aagagaaaag aattaggtaa tgtagagatt tgttgatttt tttaagttat  19080
tattattttt aatatattga aaatattaag ttagaaatat ttaattttt aattagaata   19140
ttcggttttt tttaaatttt ttaatattag ggagtttaaa gttagaggtg aaatgtaatg  19200
aatagattat ttcgttgggt atatgtagag gtttgtgaat tgtatatatg atttgtgta   19260
taatgagttt tttcggtatg tggtatattt atttgattag ggatagaatt ttaaattttg  19320
tattgttgtt tttgtgagta gaattaaatt taatggtata tgaatgtaaa tttttatgat  19380
ttaattgtag ttttttataa gaaatgtttt tttattttta aaagaaagg gggaaaggat   19440
aatagaaata gtagtaataa tttacgtgaa aatttaaagt tatgttaagt taggttattg   19500
ttggtgtttt tttttatagt ttttaaagga ggaaagatgt tttaattaat aaagttaatt  19560
tttgtaggta taagtttttt gtgttttatt tagatttgta attatatata gggaatattt  19620
tgattagttt taatttttt agtgttaaat cgaatttgaa gattggttaa tacggatatt   19680
taagttatag aagggagagt agatatattt ttttgttgat atgttatatt gggagatatt  19740
ttatcgtatt tgatagtttg ttttttagtg atgttatatg aatatgttag ggtaggtatt  19800
ttgaattaat ttttttgtt agaagatttg aattttttg tagtagtttt tatatattga   19860
agatatttag agagaatttt agaggcggcg gttatcgtga gagggtattg ttggtgagtt  19920
attttaggt tatttatatt ttgttttatt tagagtagtg gtatatttt ttattgggta   19980
tattattagt ttttattta atgaaaggat tcgtggttga gtatataagt aaataaaaaa  20040
atgaaaatta ttgttttagt ggaaaaatat tataaaattg taaaataggt tattaatagt  20100
aaaagtattt atttataaga aatttttatat atgcgataat tagataaatt gaatgtattt  20160
ttaaaatatg ggtagttta tatataatta aatttgtttt tagaagttta ttatgtattt   20220
tttaattttt taagtttat tagttggttt aatataaatg tgtagatttg agatttaaaa    20280
ttagtattaa aataataaa aataaaaata aagaaaatat aaagttgata atatttaatt  20340
aatttggata aggtttgaag agtaaaggaa gatttttatat gttagttaaa tatttaaaag  20400
atttggttat aagttttga taattgggaa atattataaa atatagtatt ttttaaatt   20460
tagttatttg ttgtttagtt tttatgattg tggttatta ggttatattt ttgtttattg    20520
ttatttaata cgttttta gatatttaat ttttttttt tgattttaat attttgtttg       20580
gttttgtttt aaataatatt gtttatgaag ttataggttt aatataaaat ttaataaatt  20640
ttttaatat ttagttattt ttatataaaa tataagtatt attaaaataa aatgtttagg   20700
tattatttaa aaatggtggt atatgattga tggaagtaag agtttagtat acgtttaagg  20760
ataagggtgt tggtttatat ttgggagtt aggattttgg tttattgtg ttgtatgatt     20820
gggtttagt tttttatt gtaaaatagg aataataaaa gtatttaatt tacggtatag     20880
ttaagaagat taaaattagt taatttatat aaatgtttaa aatagtgttt tgtacgaaat  20940
ttttgagtaa atgttagtta tgatgttatg atggtgatag tgattaatat tatagtaata  21000
atgatagtta aattgtaatt atttaaagat tatagtgatt ttttttattt aaaaatatat  21060
tttaggatat aaatatattt aagaaaatat gtttttatat ttgatattta tattaatata  21120
tgttttggtg atataaaagt tattttatat tggtttaacg taattttatt ttgaaaatat  21180
ttatgtgata ataggaatta gattttgttt aaaaattata atttaaataa attatttgtg  21240
tagaaaaaaa aaaattaaaa aattttaata cgatagaata tataggtttt tttttattg   21300
tttaaaagta cgttaaaata aatttatta ttgtatgtaa ataaaagttt taaaaatatg    21360
```

-continued

```
aatatattgt attaaaatat tttatattgg aaaaaaatga gaattttttgg tatttttagaa    21420
tggtgttttt tttatattat tatgtattga aattttaggg taagaaaagg gttagattaa    21480
ttttgaaagg ttttaaatat taaattatat tattgtgtta gtattttaag attaattagt    21540
atttttaat gataaaaaag gttatagtga gatttagagg tgtatttttt gaaattgttt    21600
taaattatta tataaatgtg gttttgataa tataaaatgg tttttatttt aaattaatta    21660
gttttatttt ttttttttgga ggtgtgaaag ggggttagggg agtaagaata gtagtgttta    21720
tttttagtat ttttttatta ataaaaagat ggatggagaa atattaagaa tgataaattt    21780
taagcgtaaa atgatatatt attaaagtat atattaatgt atagtttat aagtaatatt    21840
gagtgatagt aatgtttata aagttttttaa attttttaaa agtaattaaa gttgtttgta    21900
ttttttttga atgtgtaatt tttgtttatt ttttttttatt taagtttaag ttaaatgacg    21960
ttaagtttgg ttttaaaaat gatttaatga ttatgtagtg ttttttttttat taaaatatat    22020
ttaattataa gatgtagtat tatatatatt gtattttatt tatttttagg gtaaatgttt    22080
gaaatagtat gttattttttt agtttagtag gaaaaattta tgagagaagt aggtatattg    22140
taatgttatt ttatttttttt ggtgttgatt tttttttattt agtaattatt gtaataaaat    22200
tttttaattg tatttttgaa tataattagt ttaagatatt ttataggggag gtacgttata    22260
agagtttagt atttagtata tgtaagaata atatttattt agaaaaagaa attgttaaga    22320
ttatattttt attgaaaaaa gaagaaggtg tttttgataga ggtttgttta gttttttaat    22380
gagaggattt aaaacgtttt ttattttttga tagtatattt tttatttat tttttaaata    22440
agtgatttga aatatttata attagatagt atttaatttt aggttttaag tgttttaata    22500
gttttatgaa atatgattag tagttgtaat atagaattat ggtgaataaa ttttttataa    22560
agagggtttt gttttttatag aatgtttagt gtttttgtat ttatttaata gaaaaaaatg    22620
ataatgagaa agtataatat atatttgtat ttttaaatta tttaatattt aattaagtag    22680
tgaaaaagat tattattttt tttttttgaaa tttgtataaa aattgtgagt ttttgtgggg    22740
taaaataagt ttgattattt gaaagttaga atgtgaattt tttaatattt taattttttta    22800
taataatagt tatcgttttt ttgttatttt attttttttaa aaattttaaa aaattaatt    22860
ttagtgtata aaatgttaaa atgaaatatt aagttatata aatatatttt tagatacgat    22920
attagttatt tagagtttgt aatagagatt gaaaatatga aattggatat tttattttttc    22980
gtggttatgt aaaatttatt tatattttaa agtataatat aaataaaaag gaattttttta    23040
gaaatggagt atttgttttt ttttttttttt ttttaattta aagagttttta ttaaaagaaa    23100
aaaataaatt atagtaaaat gataagtaat ttatttgtta gttattcgtt aaaaaagaaa    23160
tttttatgta atttttttttt ttagttttta gaattttttt gaaattttagt atttattttt    23220
ttttaataatt aataattatt atttttttttt atataattat ttttttttat ataaattta    23280
agatttttaaa aattttaaaa tttaagttta ttattttaaaa gaagtgttaa ttgtgagtat    23340
atatatatat gtgagacgtt ttattttgga aatgagaaat ttaattttaa atatttaata    23400
aatattaata aaaagaaaat aattgagtaa atttttatttt agttataatt gtgaattaat    23460
cggtagttat aatggttttt aaatattgaa atatattatt tttaggaaat ttataaagga    23520
aaataggttt ttgaaaatta tattgattgt agatttttat ttattatgaa agataagtat    23580
atattattaa taattagaga aaggagatat ttttaataaa tttaattatg ttgttttttaa    23640
agttgtagtt gttaaaggtt ttaatatttt tgtatagtta ttttttaaata cgggtttaat    23700
tttgaatgat ttataatttt taattaggtg gaataaaatta ttttttacggt ttataataat    23760
```

```
aaatgtgggt gtagttatgt ttgttttcga tattgttgtt ataaaaatta gattttggta   23820
gttttgtttt atataaaata atttgttttt tgttattatt gtttttgtt ttttgggata    23880 atgttatttt taaaaatata taaatgtttt tgaatgtagt ttttaaaac gtttcgtatt    23940 acgtattaaa tatttttgg ggggattttt ttttatttt tttagtttt ggttttta       24000 ggtttaagtt tgttaataat attttaaaag ataaaaaaa aaaaaaggt attgattttg     24060 tttaaaatta aatcgtattc gggaaaggaa tttaagtata atttttttt taaggtttta    24120 aaataaaaa taacgtaata aataaaaaaa ttatcgttaa tttttaattt tgttagttat    24180
ttacgtgtaa gtgaaatttt agaagttgtt gatggggagt tcgcggttgt taaacgtttt   24240
taagattttt atttaaattt cgtaggagtt cgtattgaaa ttgataaata ttcgagggtt   24300
tataaagtgg ttatagatga gaagaggaat aaaatgttat attttaggag gtgtatttcg   24360
ttttaataat tacgttgatt ttagggtgtt aagttaaaag gggtaaggga gaaagaaaat   24420
tgttaagtat gagttttaa tgtgaaattt aatttgttgg ttttttttagg tattagattt   24480 tggaagtgtt tgtaatgata gttaggaaag taaattaatg gttaacggtt tattgggttt   24540
gaatattaga gttttgttat tttttttatag attaagtata taatatatat atatatatat   24600
atatatatat acgaagttgt tttacgtgga attgttttgg aattaaaata tacgttcggg   24660 cgttatttg tattttggta gaaagggtag agggatttgt attttttttt tttgttttta    24720
ggttaagatt tatgaatgat ttttaggtt cgttcgggat ggcggggaga ggcgtaggag    24780
acgcggtgag agaggatagt ttttatatta tttttcgta tatattttta ttttaggcgt    24840
aaattcgttg ttttttatagg aaggagaaag aggggtggtg gtgaagggaa atattatttt  24900
tttaagtagg gaagagatga taaaaattaa attgcgtttt ttgttttcgt tttagttttg   24960
ttatcggatt cggttcgtaa attttttaat cgtttcgagt tgtttagaat ttcgtaaata   25020
aagggagaaa atttttttaa gtgttattaa acgaaagttc gggttgttgt gcggcgtaga   25080
ataaaataag tatatatacg tttattttta aatttcgttt tattacgtta aaaattcgag   25140
ttattttaag ttttattgtt tttttagatt tagtaggttt ggaaggagag aaaaatttgt   25200
tttatttagt taggtttttt tttttggaga agttataagt ttttatggt attcgttatt    25260 cgagttaatg aacgcgattg ttttgataag gcgttttta ttttatcgat tttggtaaat    25320
tgtaggagat atttagttta cgttatataa aaattattaa agtgggatcg tcgtagttga   25380
aaagttcgat tagtgtttgg agattagaac gcgagttttt aaagtatata cgtattcggt   25440
atcgggaaag tttaggcgtt tgtgattttt cgaaggattt tgggttagta ttttcgcgtt   25500
tggattattt aggggttat tagaaagtaa tatacgttat aagaaagatg tggggagat    25560 ttcgatgttc gcgtttttgt taggtggagg cggggtgtag gtagaagtcg cgcgttggat   25620
tgttggatga atttcgttac gcgtaggttt cgcgtcgatt tcggaaggga taggtaggtt   25680
cggaagggat ttttgggtt tgggacgtt tttagggta gagagtatcg ttgcggttcg      25740
agcggttcgg gtttttaggc gtgggtatt cggttttaa gcgtttttcg gggacgtagg    25800
cgtttacgta tcgtttagtt gcgcgttttt agtatttagc gttcggcgtt ttcggcggag   25860
tttcgcgtat tttttcggaa agtttggggg ttttttaat ttaggttttt tcgggagttt    25920
tggggcgggg gttggaagaa ggggttattt attcgtcgt tcggttcgtt tcgggttttc    25980
gaagtgtttg ttttagtcgc ggtttagtgc gttcgtaatt aagtatttat tttcgttttt   26040
tttagtgtcg aagtttttt ttcgcgttgt gttttggtg aaaataggat atttttttcg     26100
gttattttat aataaatagc gtatataagc gggggagaag cggggcggag ggagaagtcg   26160
```

```
gtttcgaggg ggaggaggaa aggagaggag ttaaaatttc ggattgcgat agggggaaa    26220 ggagaagaaa agaaaatgag agagcgcgtt tagtcgtcgt agtcgttatt tttcggtttt    26280
tttcgtagtt tttttttttt ttttaaggta gcgataattt tacgtggata ggatggaagt    26340
tttgcgcgga agtcgggaac ggtcggagcg tgcgtcgcgt tgtcggtagt ttcgtatttg    26400
cgtagggagg tggggcgggg gcgacgtcgt tatcggttat tgcgggttcg tgaggtcgtc    26460
gggggtttcg ggggaggtcg ttagggacgc ggggggcggc ggcgcgcggg ggatttattt    26520
cgttttattt tgatttcggg tgattgttta ttgttatggt ttgcgatttc gcgtggggat    26580
cgtttagggt ttcggggttt tggatgtttc gggtggcgtc gtcgtaattt tcgtgttttt    26640
cgcgtcgttt ttatttcgtt tttattcggg tcgattcgag cggttgtagt ttttaggttg    26700
agggagggga ttcgcgatcg cgttttttttt tttgggtcgg agagttattg tcgattttta    26760 tttgttttg tggggtagtt ttcggaattg tttggaattt tttcgttatt tagttttttt    26820
gtgtaggtta ttgcgggttt tttgtcggat tttttttttat ttattttaag ggaggagata    26880
gaagggattt cgtttatttg taataacgtg aaataaaaat taatttagat tagattgggg    26940 cgttttttt gacgggagga aatatttttt ttcgtggaga tatatgttat gaaggattaa    27000
gcggtttggg gataggttgt gttgcgaagg gtttgggttt tttttagtgt tgttgggtgt    27060
aggtataggt attcgtttta gacgtttaaa ggttaggtag taacgattta ttttttaaggc    27120 ggcgttagag tttttttagg tatattgttg aaatgatatt tcgtgtttaa gttttttgcg    27180
tatgtattac gcgattatat aggatttacg attttatatt tatacgtgtg tatgttataa    27240
ttaggggata tagtaaaggt agacggaata aataatttat aaattttgta tttatttaat    27300 tattttttt aaaaatttat tgtttatttt agcggtattt ttttttgttat attgataata    27360 aatgttttaa tttattgata aattattgag tgttaattat tgtattggtt atttatggta    27420
tatgagttta tttaattttt atgataattt tacggtggtt attattaagt cggtataaaa    27480
gatgaggaaa ttaaagttta aagaattatg agtgattttt ttaaagataa atttagtggt    27540
ttttaattat aaagttttatg atataataat ttttatatta ttttaggtgt ggtttaagag    27600
attatagatt aattcgtaga aattattttt atttaaagaa agtttagttt taatatattt    27660
attaagttac gttttgaaaa aggtttagaa aaaagatttt attttttatt ttaggttggt    27720
tttatgtaat tgatatgagt attgtttaat ttaaagtag tattaatttt gaatatttat    27780
ggttataatt tatttttaa tgagtgggga attatttata atgtttaaga ggttttagaa    27840
aaggtggtgt tgtaaattta aaatgataaa ggtagtcgtt gttgttttta ttatttattg    27900
ggtgtttttt tttgtagatt tattttggag ggtgtaggta ttgttaggta taatgttttt    27960
ttttttggtt tttaaggtag aaaggggttt ggtagtgggg ttggtataaa gcggatttgg    28020
agtatggttg agagtatatt ttggtttaac gaggaatgtt agtaatata tattggagag    28080 aaaaatatga atggatagat ttaattaatt ttgtagattt attttttttta ttttatatgt    28140 gagaaaatta agggtttaga attttttagaa gtttgttaat aaatggtaga tttgagtttt    28200
aagtagtttt ttatttaagt ttattttttag ttattgtgat gttattatta gtattaatgg    28260 tattttagaaa aatagtaatt tttttaaata tgtaatatat taagttaa atatgtaatt    28320 taaatgttttt gtgaattata gtgtttaaga atgttttgtg gttatagtaa atattatgta    28380
aggattaagt ataatgatga attaatatt gttttttaaaa ggtaataata ttttgaattt    28440
tattttggta taaaatatta tgtgttagtt ttatttataa ataaaggtgg gagatgtatg    28500
atttgaataa aataaaaatt tatattttag tatattgtta atataaatat agggtggggtt    28560
```

```
tttttagtat gtttttttgt atttttttaa agttagattt tttagttata ttgattttgt    28620
ttttaaggtt attttgtttt tgtatagttt tttgtatatt tagataagaa tatatgtata    28680
gaaattattt ttaaaattta ggataatata ttagttattt gattttatat tattattttt    28740
taatagttgt tttaaatata tatatattaa tatggatatt attaggtgtt agataaaacg    28800
ttaattttta gtatatattt gaataagtt taatatagga aatagaattt tagggttata     28860
aaggtaaaaa tgtattgttt gtttaaatga ggttttattt ttagtattta tattgaatat    28920 tattttata attatagtta tatcgtttat attattgatt taatatgtat tttaaataa     28980 tttatttta ttaaataagt ttatttgata aaggatattt tttatagtta ttataaatgg     29040
aaaattaata aaattcgtta tgaatagaag atgattttgt aaaggaattt atattgtaga    29100
aataaaagtt attttttatg tattatttaa aattattttta tatatagttt gagaaatatt   29160
ggtttaaaga attatatttt atatgttttt taggtttatt aagagatatt tttaagtttt    29220 tttttttat aatcggaata aaatgttgtg tttaatttat tttgaggtat tatttttaa      29280 attttgtgtt tatttaatta ttgtttttttt tgtttaaaat atatttgaag ttttttgaagt  29340 tgaggcgttt ttttaaaatt tatgtattat ttattgtttt atttattatt ttatttgtgg    29400
taaaatgtaa ataatttata aatgtataat taaaaagtaa attattttttt tgaaatattg   29460 tatcggttat ttattatttt tttttagtat ttattagttt agtagtgtaa tatagtatag    29520
ataatgaaga agagagggaa agtagaatag tgggagaaac gtaaagggtt tagaaagata    29580 tatggggaa attgaagtta gagatttgtt gttagatttt tgaagtgatt taaaaatatt     29640
agtgggtttt gtatgatatg agttaggttt ttagaatatt tgtatatgtt taatttagtt    29700
tgaaaaggga tgtgttttgg gaggagtggg gagataaaaa atataagatt ttatagggta    29760
aattagtgga aatataagat ttatttatta gtaattttttt taattaattt ttttggaatg   29820
ggatgttttt gtagttatta tttattattt gtttattttt taaacgtgta tggtattgtt    29880
ttggtattag atttttgtata agttaaatta aataaagcgt tttaggagtt tataaatttaa  29940 aatataattt ttgtttaat tttatttaaa agtaattttta agggaaaaat tag            29993
```

<210> SEQ ID NO 4
<211> LENGTH: 29993
<212> TYPE: DNA
<213> ORGANISM: Artificial Sequence
<220> FEATURE:
<223> OTHER INFORMATION: chemically treated genomic DNA (Homo sapiens)

<400> SEQUENCE: 4

```
ttggttttttt ttttaaggtt gttttttaaat gaaattaaaa taaaaattat gttttggatt    60
atgagttttt agagtgtttt gtttaatttg atttatataa aatttaatgt taagatagtg    120
ttatgtatgt ttgaaaaata aataaatagt aaatggtaat tgtagaggta ttttattttta   180 gaggagttgg ttaagggaat tgttaataag tgaattttat attttttattg atttatttta   240 taaagtttta tatttttat ttttttattt ttttaaaat atatttttttt ttagattgag     300 ttgaatatgt ataaatattt tgagagtttg atttatgtta tgtagggttt attggtgttt    360
ttgaattatt ttaagaattt ggtagtaggt ttttgatttt aatttttttt atgtgttttt    420
ttaggttttt tgtgttttttt ttattgtttt atttttttttt ttttttttat tgtttgtatt  480
gtattgtatt attgggttaa tagatgttag ggaagggtaa tgagtaattg gtataatatt    540
ttaggaaagt gatttgtttt ttaattgtgt atttatgaat tgtttgtatt ttattataaa    600
taagatagta agtaaaataa taataatat atgaattta aaaagatgtt ttaatttag       660
```

```
agattttaag tatattttag ataagaaaag taataattaa ataagtatag aatttaaaaa    720
gtaatatttt aaagtaaatt ggatataata ttttgttttg gttatgaaaa ggggaggttt    780
gaaaatattt tttggtgagt tgagggata tatggaatgt aattttttaa attaatgttt    840
tttaaattgt atgtgagata attttaggtg gtatatgaga aataatttt attttatat    900
tataggtttt tttgtaagat tatttttat ttatggtggg ttttattagt tttttattta    960
tggtgattat aaaaaatgtt ttttattaga taaatttatt taataaaaat agattattta   1020
aagatatata ttaagttaat aatataggtg atatggttat aattataaaa gtgatattta   1080
atgtaaatgt tggaaataag gttttattta agtaaataat atattttgt ttttataatt   1140
ttaaaatttt gtttttatg ttaaatttat tttaaatgtg tattgaaaat tgatgtttta   1200
tttgatattt agtggtgttt atgttaatat atgtatattt aagataatta ttagaaggta   1260
gtaatatgaa gttaaataat taatatatta ttttggattt taaaaataat ttttgtatat   1320
gtatttttat ttagatgtat aaaaaattat gtaggagtaa agtgattttg aaagtaaggt   1380
tagtgtaatt gaaaaatttg attttagaag ggtataaaga aatatgttaa gaaaatttat   1440
tttatattta tgttaataat atgttaaagt atgaattttt attttattta aattatatat   1500
tttttatttt tatttgtagg tgaaattagt atataatgtt ttatgttaaa atgaaattta   1560
aaatgttgtt gtttttgag gatagtatta aatttattat tgtatttaat ttttatatga   1620
tatttgttat agttatagaa tattttaga tattatgatt tataaaatat ttaaattgta   1680
tatttggttt gtaatatatt atatatttaa aagaattatt attttttga atattattaa   1740
tattaataat agtattatag tgattaagag tggatttaaa taaaggttgg tttgaaattt   1800
aggtttgtta tttattagta agttttaaa aattttgagt ttttagtttt tttatatgtg   1860
aaatggagaa aataaatttg taaaattaat taaatttgtt tatttatatt ttttttta   1920
gtgtatatta attggtattt tttgttaggt tagaatgtgt ttttaattat gttttaaatt   1980
tgttttgtgt taattttatt gttagaattt ttttatttt gagaattaga aaaggaaata   2040
ttatgtttgg taatgtttat attttttaaa ataaatttgt aggaaagaat atttagtaag   2100
tgatgagagt agtaatgatt gttttatta ttttaaattt ataatattat ttttttaga   2160
gttttttaag tattgtagat aattttttat ttattaaaaa ataaattgta attataagta   2220
tttagggttg atattgtttt tgaattagat agtgtttata ttagttgtat aagattaatt   2280
taaagtagag gatgaaattt ttttttgaa ttttttttag aatgtaattt agtgaatata   2340
ttaaaattaa atttttttg aatgggagta attttatgg attaatttgt aattttttag   2400
attatattta aggtaatgta gaggttgttg tattataggt tttgtgatta gagattattg   2460
gatttgtttt tggaaaagtt atttatgatt ttttgggttt tggttttttt attttttata   2520
ttggtttaat aatgattatt gtagagttgt tatggaagtt aaatgaattt atgtattata   2580
agtgattaat ataatgattg atatttagtg atttattaat aaattaaaat atttattatt   2640
aatatgatag agaaggtgtt gttaaaatag ataataggtt tttggaagag gtgattaaat   2700
ggatgtaaaa tttatggatt gtttattttg tttattttg ttgtgttttt tggttgtggt   2760
atatatatgt gtgggtataa aattgtaaat tttatgtagt tgtgtagtgt atgtgtagaa   2820
ggtttagata tgaaatgtta ttttagtaat gtgtttagag aagttttgat gttgttttgg   2880
aagtaagttg ttgttgtttg attttttggg gtttgggatg gatgtttata tttgtattta   2940
gtagtattgg aaggggttta ggttttttgt agtatagttt attttagat tgtttagttt   3000
tttataatat atatttttat ggaaaagggt atttttttt gttagaaaaa gtgttttagt   3060
```

```
ttggtttggg ttggttttta ttttatgttg ttgtaagtag gtgaagtttt ttttgttttt    3120
tttttttggg taagtggaaa ggagtttggt aggggggtttg tagtggtttg tagggggaa    3180
ttgggtagtg agagagttttt aggtaatttt ggggggttgtt ttatagaagt aggtggggat    3240
tgatagtggt ttttttggttt agggaggaga gtgtggttgt gggtttttttt ttttagtttg    3300
gaggttgtag ttgtttgagt tggtttgggt gggggtgggg tgggggtggt gtggagggta    3360
tggagattat ggtggtgtta tttgggatat ttagggtttt gaggttttgg gtggttttta    3420
tgtgagattg taaattatga taataggtag ttatttgagg ttaaataaaa atggagtggg    3480
ttttttgtgt gttgttgttt tttgtgtttt ggtggttttt ttttgaggtt tttggtggtt    3540
ttatgagttt gtagtagttg gtggtgatgt tgttttttgtt ttatttttttt gtgtaagtgt    3600
gaggttgttg gtagtgtggt gtatgttttg gttgttttttg gttttttgtgt aaaattttta    3660
ttttgtttat gtgaagttgt tgttgttttta gagagggggga aagagttgtg ggaaaagttg    3720
gggagtgatg attgtggtgg ttgggtgtgt ttttttattt tttttttttt tttttttttt    3780
tttgttgtag tttggagttt tggtttttttt tttttttttt ttttttttgg agttggtttt    3840
ttttttttgtt ttgttttttt tttgtttgtg tatgttattt gttgtggggt ggttgaaggg    3900
gatgttttgt ttttattaga ggtatagtgt gaaggggaaa ttttgatatt ggaaggaatg    3960
agaataaata tttaattatg gatgtattga attgtggttg ggatagatat tttgggaatt    4020
tgaggtggat tgggtgatga ggtgagtgat ttttttttttt aatttttgtt ttagggtttt    4080
tggggggagtt tgagttgaga gaattttttaa attttttggg aaagtgtgtg aggttttgtt    4140
ggggatgttg agtgttgggt attgaggatg tgtagttgga tggtgtgtgg gtgtttgtgt    4200
ttttgggggg tgtttggagg ttgggtgttt tatgtttgag ggtttgggtt gtttggattg    4260
tagtggtgtt ttttgtttta gaagatgttt ttaagttttta agggttttttt ttgagtttgt    4320
ttgtttttttt tggggttggt gtggagtttg tgtgtaatgg agtttatttta gtagtttagt    4380
gtgtggtttt tatttgtatt ttgttttttat ttggtagagg tgtgagtatt ggggtttttt    4440
ttatatttttt tttatgatgt gtattatttt ttgatgattt tttagatggt ttaggtgtga    4500
ggatgttgat ttagagttttt ttggagggggt ataggtgttt gggtttttttt ggtgttgggt    4560
gtgtgtgtat tttaaaggtt tgtgttttaa ttttttaggta ttgattgggt tttttaattg    4620
tggtgatttt attttaatag ttttttatgtg gtgtggattg aatgttttttt gtagtttgtt    4680
agggttggtg aaattagagg tgttttgtta gagtagttgt gtttattggt ttgagtagtg    4740
ggtgttatgg aaggtttata attttttttaa aggaagggat ttggttgggt agagtaggtt    4800
tttttttttt tttaagtttg ttgggtttgg ggaggtagtg gaatttgaaa tggtttggat    4860
ttttagtgtg gtgaagtgag gtttggaagt agatgtgtgt gtgtttgttt tattttgtgt    4920
tgtatagtaa tttgaatttt tgtttggtag tatttgaaag agttttttttt ttttgtttgt    4980
gagatttttga atagtttgga gtgattaggg aatttgtgga ttgagtttgg tggtagagtt    5040
ggggtgaaag tagagagtgt aatttaatttt ttgttattttt tttttttgttt gggaggatag    5100
tgttttttttt tattattatt tttttttttt tttttttatga agataatgga tttgtgtttg    5160
gggtgagagt gtgtgtggga gagtggtgtg gagattgttt ttttttattg tgttttttgt    5220
gtttttttttt gttatttttga gtgggtttag agagttattg atgaatttta atttgagggt    5280
agggaggaa ggtgtaggtt tttttgtttt ttttgttaag gtgtagaata gtgtttgggt    5340
gtgtgttttg gttttagagt agttttatgt ggagtaattt tgtgtgtgtg tgtgtgtgtg    5400
tgtgtgtgtg ttgtgtatttt gatttgtgag gaggtaatag gattttggtg tttaaattta    5460
```

```
gtgggttgtt ggttattagt ttgttttttt ggttgttatt atagatattt ttaaaatttg    5520
atatttaaga gaattaatag gttaggtttt atattaaggg tttatattta atagtttttt    5580
ttttttttta tttttttttgg tttggtattt tgggattaat gtaattgttg gagtgaaata   5640
tatttttgg aatatggtat tttgttttttt ttttatttg tggttatttt gtgaattttt    5700
gggtgtttgt tagttttagt gtgggttttt gtgggattta ggtgggagtt ttaggagtgt    5760
ttaataattg tgggttttttt attagtagtt tttgaagttt tatttatatg taggtgattg   5820
ataggattga aagttgatga tggtttttttt gtttgttgtg ttgttttttgt ttttaaaatt  5880
ttagggaagg gattgtattt gaattttttt tttgggtatg gtttggtttt aagtagaatt    5940
agtgttttttt ttttttttttt tgttttttaa aatattattg gtaagtttaa atttgaagaa  6000
ttaaaaatta gaggggtgg ggagagaatt ttttaaaaa atatttgata tgtgatatgg      6060
agtgttttag gagattgtat ttaaagatat ttgtgtattt ttaaaaataa tattattttta   6120
agaaataaaa agtagtagta ataagagata gattgttttg tgtggagtaa gattgttaga    6180
atttgatttt tatggtaata atattgaaag tagatataat tatatttata tttattgtta    6240
taaattgtaa aaatagtttg tttttatttga ttaaaagttg taagttattt aaagttaaat   6300
ttgtatttag gaatgattgt ataagaatgt taaaattttt gatagttata gttttgaaag    6360
taatataatt agatttgttg aaaatgtttt ttttttttga ttattagtga tatgtatttg    6420
tttttttataa taagtaaagg tttataatta atatggtttt taaaagtttg tttttttttg   6480
taaattttttt gaaaatagta tgttttaata tttaaagatt attgtaatta ttggttggtt   6540
tataattata attaaaataa gatttattta gttgttttttt ttttattagt atttgttgaa   6600
tatttgaaat tgaatttttt attttttaaaa taaaatgttt tatatatatg tatgtattta   6660
taattaatat ttttttttaag tagtaggttt aagttttaaa attttttaaaa ttttaagatt  6720
tgtataaaaa ggagtgattg tataaaaagg aataataatt attaattgtt aagaaaaata   6780
gatgttgaat tttagagggt ttttagaagt tggagaaaaa aattgtatag aagttttttt   6840
tttgatgggt gattggtaga tgagttattt gttattttgt tataatttat ttttttttttt  6900
taataaggtt ttttgggtta aaaaaaaaaa aggaaaaata agtattttat ttttaagagt    6960
tttttttttta tttatgttgt attttggggt gtaaataaat tttatatagt tatgggaaat   7020
agagtattta attttatgtt tttagttttt gttgtaagtt ttaaatgatt gatgttgtgt    7080
ttaaaaatat atttatatgg tttgatattt tatttttaata ttttatgtat tggaattaga  7140
tttttttagga ttttttagaaa gatagaatga tagaaagatg atgattattg ttataaaaag  7200
ttagaatgtt aggaagttta tatttttaatt tttaaataat taaatttatt ttgttttata  7260
aaaatttata gttttttatat agatttttaag aagaggggtg ataattttttt ttattattta 7320
gttaagtgtt aagtaattta agaatgtaag tatgtattat gttttttttat tattattttt  7380
ttttgttagg taaatgtaag aatattggat attttgtaaa aataggtttt tttttataag   7440
gagtttattt attatagttt tgtattgtag ttgttgatta tattttatgg agttgttaaa    7500
gtatttaaaa tttaaaatta ggtattgttt ggttgtaaat attttagatt attttatttaa  7560
gaaataaata gaaagtgtg ttattaaaag taggagatgt tttgaattttt tttattgaag   7620
agttgaataa attttttatta aaatattttt ttttttttttt agtgagaata taattttgat  7680
agttttttttt tttaaatgga tattattttt atatgtatta aatgttaaat ttttataatg  7740
tgtttttttg tagagtattt taaattaatt atatttagaa atatagttgg gggattttat    7800
tataatggtt attaggtgaa ggaaattaat attaggggaa tggggtggta ttgtagtgta   7860
```

```
tttgttttttt ttatgaattt tttttgttaa attaagaaat gatatgttgt tttaggtatt    7920
tgttttggag atgggtgaga tgtaatatgt gtaatgttgt atttatagt tagatgtgtt     7980 ttaatgaagg ggatattgta tagttattaa attattttg gagttaaatt tggtgttatt    8040
tagtttgaat ttaagtggaa gaaatgaat aagagttata tatttaaaag aagtataagt    8100
aattttgatt gttttaaga ggtttgaaga ttttgtaaat attattgtta tttaatattg    8160
tttgtggagt tgtatattaa tatatgtttt ggtgatatgt tattttatgt ttgaaatttg    8220
ttatttttag tgttttttta tttatttttt tattagtaaa gagatattga aaatgaatat    8280 tattatttt atttttttaa tttttttat atttttagaa aaagagatga aattgattaa     8340
tttaaaatag aaattatttt gtgttattaa aattatattt atatagtgat ttgagatagt    8400
tttagagagt gtatttttga gttttattgt aattttttt gttattgaaa ggtgttaatt    8460
gattttaggg tattgatata atagtatagt ttgatatttg aaatttttta gagttggttt    8520 ggttttttt ttattttgag attttagtgt atggatgatg aagaaagata ttatttaaa    8580 atattagaaa tttttatttt tttttaatat gaaatgtttt aatatagtat gtttatattt    8640
ttaaagtttt tatttatata tagtaagtaa atttattta atgtattttt ggatagtagg    8700
agaaagattt atatgtttta ttgtgttaga attttttagt tttttttt ttgtataggt     8760 agtttatttta ggttataatt tttaggtaaa gtttgatttt tattattata tgaatatttt    8820
taaagtgaaa ttgtgttaaa ttaatgtgga atagttttg tattattaag gtatatatta    8880
atgtagatgt taaatatgag agtatattt tttgagtata tttatatttt aaagtgtatt    8940
tttaaataaa agtggttatt gtagttttta gataattata atttggttgt tattattatt    9000
ataatattaa ttattattat tattataata ttatagttag tatttatta ggaattttgt     9060 gtaaaatatt gttttaagta tttatatgga ttagttaatt ttaattttt taattatgtt    9120 gtaaattagg tattttgtt atttttattt tatagataag gaagttgaga tttagttatg    9180
tagtatagtg gagttaggat tttaattttt tagtatgagg ttagtatttt tatttttaag    9240
tgtgtgttgg gtttttgttt ttattagtta tatattatta tttttaggtg gtatttgaat    9300
attttgtttt aataatattt atatttatg taaggataat tagatattag aaaaatttgt     9360
taaattttgt attaaatttg taattttatg ggtaatattg tttgagataa gattaaataa    9420
agtattgaag ttaagaaaa aaaattaagt atttgaagaa atgtattaag taatagtgaa    9480
taagaatatg gtttaaataa ttatagttat gaaggttgga tagtaaatga ttgaatttgg    9540
agaaatgttg tattttgtaa tgttttttaa ttattaagaa tttatgatta gatttttaa     9600 atatttaatt aatatgtgga atttttttt gttttttaag ttttatttaa attggttaaa    9660
tgttattaat tttgtatttt ttttgttttt gttttttgtt gttttaatgt tggttttgaa    9720
ttttaaattt gtatatttat gttgaattaa ttaataaggt ttgaagagtt aaagagtgta    9780
tgatggattt ttggaggtag gttaaatta taatggagtt gtttatattt tggaaatata    9840
tttaatttat ttggttattg tatgtgtaag gtttttgta ggtaaatatt tttgttgtta     9900
ataatttgtt ttataatttt atagtatttt tttattgaag tagtggtttt tatttttta    9960 tttatttata tatttagtta tggatttttt tatttaaatg gaaattgatg atatgtttag   10020
tagagaaatg tgttattgtt ttaggtgaag taggatgtag gtagtttgag aatgatttat   10080
taatagtatt tttttatggt ggttgttgtt tttggagttt tttttaagtg tttttaatgt   10140
atggaaattg ttgtaaaaaa atttaagttt tttgataaaa ggggtaatt tagagtatttt   10200 gttttaatat gtttatgtgg tattattaaa aaatagattg ttagatatgg taaaatattt   10260
```

```
tttagtgtga tatattagta gaaaggtgtg tttattttt  tttttataat ttgagtattt  10320
gtattaatta gttttaaat  ttgatttagt attgagaaaa ttaaaattga ttaaaatgtt  10380
ttttgtgtgt agttataggt ttgaatgagg tataaaggat ttgtatttgt aaaggttgat  10440
tttattaatt agaatatttt ttttttttta aagattgtaa gaagaaatat tagtagtggt  10500
ttaatttgat atgattttag attttatgt  aaattattgt tattatttt  gttattttt   10560
ttttttttt  ttttaaaatg aaagggatat ttttgtgaa  agattataat taaattataa  10620
aaatttatat ttatgtgtta ttaagtttaa tttatttat  aaaagtaata gtatagagtt  10680
tgaaattta  ttttaatta  agtaggtgta ttatatattg ggagggttta ttatgtataa  10740
ggttatatat ataatttata gattttgta  tatatttaat ggagtgattt atttattata  10800
ttttattttt gattttgaat tttttaatgt taaaagattt gaaaagaatt gaatgttttg  10860
attaagagat tgaatatttt taatttaatg tttttagtat gttgaaagtg atgatgattt  10920
gggggaatta gtagatttt  atattattta attttttt   tttatatttg aatgtaaatg  10980
tatatttatg tgtggttatg atttaagtta tttttgttaa atttaatgat gttgtaggtg  11040
aattatattt agatttttt  ttgtaggttt tttagtaatt taaaataatg ttttagtag   11100
gtaatttaag tatgtaaatt ttaataaatt tgttaagaat ggtaatttta ttgttttatt  11160
ttgttttttt tttgtttgt  ttgttttgt  attaattta  gttgataaga tgatggtatt  11220
gttatttt   ttagttgatt tatgaagaat tttaatttag gtttagttt  tttttttaat  11280
tgttgattt  agttttaaa  ggttttgttt atgaaaatgg ttagtaaagt tgtgggtatt  11340
tggtaaatgt ttgttaaatg tttttttttt attagtgttg ttgaagattt gtaaaattag  11400
agtgggatgg atagatttt  ttttattt   gtatggtttt gaagattttg gagtttttat  11460
tgtattta   tattttata  tattattttt aggaatattt agagagagaa ttattgtaat  11520
taaggttata ggtttaattt ttaggtattt aaattagttt taggtggata attgttttat  11580
atatatttgt ttgtattaat gttgttataa taaatatagt tataatattt tgatgtttt   11640
tttggggtt  tattttggat tgtgttgaag ttgttttaa  tatttttta  tgttttaag   11700
atatttaatt atatttgttt atgattttta tgaggttttt tttggattta aaattttta   11760
aaaaatttgt ttgttgttta tagggtaaat tttaaattt  tttgtaggga agataatttt  11820
ttatattgag aattttgttt aggttgtttt tttatttt  tatttttat  ttataataat  11880
ttttttttt  agttgtatgg aaaattgtag ttttttaaata tattttggat attttatt   11940
tatttttg  tgtgtggaat gtttttttt  tggaaaatat tgtttttt   tttttgtaaa  12000
tatttttt  attgttttt  taatatttaa ggtgtaaaat gttagttttt ttgataagtt  12060
ttttgattt  ttagagtttg agttgaatgt ttttttttg  ttatttaa  agtatttagt   12120
tttatattt  aatatagttt ttgttatatt gaaatgtaat agattatatt agtttaaatt  12180
ttgttaag  ttgagaattt attggaagga ttagttgtat ttgttatttt tgtattgtta  12240
atgtatagtg tattgttgga tatatagtta gtaggtagtt gttatattt  tattgaatga  12300
atgagtagag gtattgggaa tgagagtaga gattgtgata ttgaatattt tttttttgag  12360
attgggaata gtgagaaggg tagtgattat tataaggtgg gattatttta ataataattt  12420
tagggagttt tggtataaat ttagtagaat tgtagttgtg aatttaggtt taggttatat  12480
gtatgtatat gtgaatgtag aaatgtgttt attttttatt attgggaagt tagtgatttg  12540
gtggataagt taaggatttt gaaaattt   ggagatatgg taatttata  gtatttgaaa  12600
tttgagagat ttagtttta  tagtatagtg agtaagtaga aagaatatgg gggttgggtg  12660
```

```
tggtggttta tatttgtaat tttagtatttt tgggaggttg aggtggatgg attatttgaa  12720
gttaggagtt tgagattagt ttgattaaaa tggtaaaatt ttgttttttat taaaaatata  12780 aaaattagtt gggtgtggtg gtgggtgttt gtaattttag ttatttggga ggttgaggta  12840
ggagaattat ttgaatttag aaggtagagg ttgtagtgag ttgagattgt attattgtat  12900
tttagtttgg ataatagagt gagattttat tttaaaaata aataaataaa taaaaggaa  12960 gaagaatatg gagttaggta tttgggttta gattttagtt ttaatattga tgagtttgta  13020
atattaaata tattattgaa atagattttg ttttagtttt ttatgtgtaa tagaatatgt  13080
tttatggggt tttgatgaga atttaatgag taaatatatg taaatatatt tagagtagtg  13140
tttgatatga gtattagttg ttattattat gattgggtat tttttattag attatttta  13200 aatgttttag agatatttag agttgaaggt ttttttggg gggttatgga ttggtgatta  13260
taaatggagt gtttagtagt ttaagtataa attagatatt gtgggttatt ttggtaaatt  13320
tgaggttgta tttggagttt taagagaaga tattataggt gtttaatagt tggtattggt  13380
tatttatgtt gtgtagtaat attttttta gtaaatattt ttgtatatag taatttagat  13440
tgttttagag ttttaatttg tgtggttttt taattatttt aagtaattat aagtatgttg  13500
tataatggta gtattttata gttaatattt aagtttttt agttgttttt ttttagttg  13560 taaggtatta attatgagaa tttgtataat ttttaatagt tagtgggttt gatgaattta  13620
atgtaaattt tttaaaaggt agttttatat attgttatga ttttatttt tagagagata  13680 gtaggaggta attagtattt ttatttatag aatttattat ttggatttag atataatggt  13740
tatgtggtag gatgggttg aaggaaaaag gaaagttaaa atattaattg ttaaggtttt  13800 attttatag tttgtttgga attgttatta ggtgtatttg tatagtttta aaatgataa  13860 tgttgtattt gaattttta gtatatttaa ataagagttt tttaagtttt ggttattgat  13920 attgggtt ggataattta tttagggat attgttttgt gtttggtagg atgtttagtg  13980
gtattgttgg atgttaggga tttttttttt tttggtaatg atggtgtttt tagatattgt  14040
taggtgattt tgggagtaa aattgttttt ttttgagaat ttataattta agtagatttt  14100
aatattattt gatatagtta aaaaattttt agggttttgt ataagaggat tgttttattt  14160
ttagttaagt gtggagaatt ttaatatttt tttttaagt ttaaatatga agttaaataa  14220
tttttattag tttgtgttga tagattaatt ttgtatagag gggatttata gatatgtttt  14280
atatagattg attattttta gtatattttt ttttttgga aataatatat gagtgggagt  14340
aatagaatat ttgagagaga gtatgtagga agtaaatatt tatttgaatt atttatgtgt  14400 ttttttttt ggttatttgt tagtagatag tttggattta ttttaaata atgattattg  14460 tttttttatt tttgtgggta aatatttagt aataagaaat ttttatttta tttagtttgt  14520
agtgttagaa aaggtaaagt tattgataat tataattgtt gaagattaaa atatttagtg  14580
agttaaatta tttgtttgta atgagaaatt tttaaaagaa ttatgtgtag tttttagttg  14640
taattataag tttaagattt tgagttaata atatttgtat agttagaaga agtaaaaat  14700 aaatatatta tatgtaaaaa tttttttttg tgaattttta gatttaaatt tttaagtttt  14760 tatttatgg gtttgatgtt gattaatata tttttattat gaaatgatat ataattgatg  14820
taagtaaatt tgattgttgt ttgggtatta tttttatata atttaagtat atatgaaata  14880
tattttaaaa attatttgaa taaaatggga ataataatgt ttatataaag tgagagagga  14940 taatttttt tatatgagtt ttgggttgaa ttttaaaatt attttgaaat atgaaatatt  15000
aatattataa atatatgatt agattaattt ttttaagagt tttaaatagt agataatttt  15060
```

```
tattttatta gaaattgtaa agatatttga aattttatat ttatgtattg tttaatttag    15120
tggttgtatt ttaattgtat taggtagata attatggaag tagttagatt aatttggaga    15180
ttttatatta tttattaatt gatgtttaag taggtagggt agaggtattt gaaaatatat    15240
atatatatat atatatatat atatatatat atatatatat atttattttt tttttttat    15300
ttttttgat tgtgttttaa attttgaaat gtgtgtttag gtggtaaagg gttgtaaata    15360
tagtatattg tgtttgatta aaatattttt ttgtttttta ggtggagaag gattttgtat    15420
agttttttgt tagtagagag ataaagtggg tgttgggtaa tttaatgata ggtggaggtt    15480
gttttggg agtgttgtgg agaatttgag ataggggttt aaattataga tagtggagga    15540
gagttttgtt ttatttatgg ataggaagtt taaagaaggt atagtgaatt ataggtttat    15600
ttaggtattt tatgttagat attgaatggg aagtttagta gtttttttagt tattggagaa    15660
tggttaaaaa tttagaggtt ttattttttt aaatgagtat ttttggggtt tataaattaa    15720
ggaattttat agagtattta agttatatat tttttttttt aggttgattt tttgtatagt    15780
gggttttaat gtggtaagat ttatttatga atattttatt ttttataatg ttgttagtta    15840
tttttttttt ttttttggt atattttat tatttttatt ttttatggtt ttaatttttt    15900
taatttattt gtttagtgtt tttttgttgt ttatttggat aaaataataa taataataat   15960
aatttattta tttttaagg tttagtttaa atgttatttt ttttgtgaag ttttttttaa    16020
ggtttaggta gaattagttt ttttttttgt gtaatattat agtattttt ttggattgtt    16080
aatataatag tagattgtgt tggggtttat tgtatgtgtt tgttttttag agagattatg    16140
aatttataga ggggagagat tatattttt ttttttttgta attttaatat ttggagatgt    16200
taatggaaat taagtgattg tattatttta tgtatatttt taaagggtat taggttttaa    16260
attagatatt tgtaaaggat gaattttgtt aattttttgg aaaattggtt tttttttgtt    16320
tgtggttatg aaagttggtt tattggttat ttttttattt aatttattta agtttttatt    16380
tgtattaaag tattattgat ttttagtgg aaaaataggt atgtttggtg tatattggta    16440
tttttaataa attgatattt aaaagataga ttttttgttg aggtttatgg ttttttataat    16500
tttagttttt tttagaaata gattttgatt tttttggttg tttttttgtta agattgattt    16560
tatgttattt tgaagaattt ttaattttta gaattataga ttttatttga gagaaagtat    16620
gttttgtatt tgtttgtgtt agtgttttaa aatgtgagga ttaaaaattt tagatgtatt    16680
tattaaaaat atatgtggtt ttttgttgag ggaaattata ttttttttt taggtataat    16740
tgaggaagta aaaaattttt gtttagttt tagtggtttg ttttttaggta ttttttatat    16800
aaagatgagt aagattttt aaaaattatt aatttgtta tttaggggg aaagttttt    16860
tatgttaga aataatatta aattaagatt attgttttta atagttttaa aaattgtggt    16920
tttatttttt tgtatgagtt atttttagt atagtgtagt atatgattgt attatattat    16980
gataaagtat atttgttttg tgttttagtg ggttattta tttattagtg ttagatgatt    17040
agattagaag agagatttag tttaatttt ttatttgta gatgagatgt tgtattatgt    17100
gattttaaga ttttaagtta tttatttaga ataaaataga aaagagaat tttatgttgg    17160
ggatattta tgttttaat tttatatttt attattttat ttttatttgt ttgtttttga    17220
tgaggagttg agaatgttgg aattagatta tttttgtgtg tatttaggtt ttgttattta    17280
ttagtgatgt gattttggtt atgtaatttt ttgagtggtt gtaagttata gttttagtat    17340
gtgtatatgg ggaataataa tagtatttgt tttatgggat tgtaaggaat aattgaattt    17400
atgtaggaaa gatatttggt ttagtgtttg gtttattata aaagtttagg ttatagtttg    17460
```

```
aattgatatt ttggaataaa atgttgagtg tatttgatat ttagagaagg aaatttatgt   17520
tgttaaagta agttttttt tttaatttgt tatttaaaaa atataaataa gttatatttt    17580 gtataaatata ttaaaataga gatgatagag gttattttttg agaggaatga ttagagggag  17640
taagagagag gttttggaat gttgattatg ttttttattt tggtttggtt gttggttatg   17700
tgaaagtgtt tatttaataa aaatttatta gtgattaatt tttgatttat gtattttatt   17760
ttattgtgta tatgttatat tttttaaaa agttttaaaa atatggatat atttaaagta    17820
aaaagtggat ttatttattt ttatttttg taaattagga taagttgtta tatttagatg   17880
tgtatttttt taggtatttt tttttttata tatgtgtaaa tgtaataatt atgtgaggat  17940
gtaatttatt tttattttat attttttaatt ttaataggat tattgatttt tttaaaattt  18000 gttttgatt tgttgaattt tgaatatttt tttatattag tatatatagt tttgggtgtt   18060
tttatttaat gtatgtagat attttataat tttattgttt ttttttggt gtatgtttat   18120 attgttttta tatttttatt attattaagt atgttgtatt gatgattttt atgttttttt  18180
gtatatttgt taaaaatatt tgtagataaa attttagatg taatattaat agataaatat   18240
gtatgtgtat ttttttataga aaatattaaa atgtttttta aaaagattta tgaatttgt   18300 attttttaagg taatatttt attttttta taaaaattag gtgtaaaaat tttaatttaa  18360
ttgaattttg taattatttg tgttttggtt aagaaaaatg gttatagtag taaattttt   18420 gaaatttata tagtaattgg aatattttat tatgattagg ataaataatt ttattaatga  18480
tatatattta atatatatat aatttata taattagttt tttatttaag aatatttagt   18540
atttattttt atgaatgtat attatattta tttatggttt gtaagtttaa atgttaggaa   18600
gaaataaatt agtaatatta tatttattat attttttttt atttagtatt attaaatatt   18660
tattagaatt attaggagaa atggttttaa ttttatgtg attggtgaga atttatgagg   18720
aatgatatat tgttattta gtaagagttt attttgtgtt aggtatagtt ttaagtattt   18780
tatatatatt atgatagttt tttaatatag agatgaaagg tatagatatt gtataagtaa   18840
taaatgatat tattttatta taaatgtgtt gataaatatt attatatatg ttataatatt  18900
agttgtgtta tattaatgat taatttataa atttgttatt tattataatt tgtttaatgt   18960
ggaaataaaa gttaatgtat taaaatttag aaaattgtta tttaaatgtt ggttaaagta  19020
atttgataga tatagttttta aaatgaagta tattaattag ttgattttgt tgtttgattt   19080
ttatatgtag aaaattttgt tttagaata tttagttttt gtagttttg gttaagattt    19140 tgattaattt ttaatggtta tttagtgttt ttaaaaagta gtttaattta gaatagttaa   19200
tgtatttttt ttgtattgaa taaatatggt tattaatttt tgtggggttt ttttttttgt   19260 agaattttt gttatttaa gggatttaat aggatttata tatataaaat tgaaaattat   19320
attattatgg ggaagttgtt ttgtgttttt tagaaggaat ttttttgtta atttaagtat  19380
tgtatgtgtg tagaatagtt aatatttttt ttttaagaaa tttatgtat gtagttaaaa   19440 tattttaaa ttgattaagg atttgttata tattttaga agtatttaag agtattttta  19500
tggttataag agtagagtgt attagaatgt tagaaattaa tgaatatgtt agaggttttt   19560
aaaattgtgt ttaatatttt tgattttatt atataaatat gtggggtagt ttggaaaaat  19620
aaaataattt ttttttttt aatgtaggtg aggtttgtga tgtaatatt ttaattggtt   19680 tgaatattaa tttgatattt ttttgttaga agtaattttt attatttagt aaatgaaatg   19740
gagaggtaat aaatatgatt gatatttatt ttttgagtaa agtattattt tatattagat   19800
ttgattagtt attttattt tttttggaaa atgtattata taaattatta tagtattttg   19860
```

```
tttattaatt agggaagtta aaaaatgttt tataaatgtt gaattaaaat ttttattgtt    19920
gtgagggaat taaattttaa gtaatatatt ttttttatag ggtgagaaat tgaagtatgg    19980
agaaattata aggttttttt aaagttatat attgagttat ggtagatata gaaatttata    20040
attttgtttg tttgatttaa tttgaaattt tatgaaatgt aatttattta ttttttgata    20100
tgtgttttag aagtatattt ttttatttgt ttatttatgt ttttatttat ttatttatgt    20160
atgtatttat gtattattga ttatttatgt atttatttat ttatttatgt attttaaaag    20220
aattggtgtt tttgtatgat atagttttga tttagggatt atgaatattt tgaatttata    20280
tattttagat atttttttaa agaaatttat tgtatttttt ttatgattat gaaaagaaa    20340
ttaagatatt aagaaaatta agttggattg tttaagtgtg ggttatagta gtgtttatgg    20400
gtagtatttg aagttaattt aggagtgaat ttagtttgtt taagtgtttg aataagaatt    20460
tggttgaagt tttggaggag atgtttgggg tatagagtgg ggatgaggaa aaattatagt    20520
attttagag agtattgtaa ggattagtat ttatattttt attatttgat gtttttatat    20580
ttggtttagt taagagagag ggggtaaatt attttgtttt ttattttgtt attttttga    20640
ttttagtttt tatgttttaa atttttttttt attgtgattt ttttttttatt agttaatta    20700
gtattttttt gtgtttttt tattaaattt gtttttttt attagtttgt ggagttatat    20760
tttttgattg aattgttggg gttataagta atttgaaatg aggaaagtgt ttagtaattt    20820
tttttagttt agtatttgt aatagagatt ttagagtatg tagtgatgat atttgttttt    20880
tttttttttt atagagagtt tagtgggtaa ttttttttggt ttgttttttt gtttttttt    20940
tgtagttta agatttagga tttagatttg ttttttgttt gtatggtttt ttatttttt    21000
ttttggaaga gtttttttttt ggggggtttt taggtttaag agtatttgga tttttgggag    21060
atgaatttgt agatttttata aagaatatttt aagtattagg taaattatat tttttttgtag  21120
tttaaatgtt agtttttttt tttttttttaa ttttattgaa gaataattta gttttaata    21180
aataagtaaa tagaatttta gggtttttttt taaaggtgta ttttttgttgt tttgaagatt    21240
attattatta atttttattt tagttaattg gttttttttt atattttttаt ttgggtataa    21300
atgtgatatt ttgtatata ttaatgttga tttatattaa tatgttaatt tataattgag    21360
tgatttaaaa ataatgatgt attatgattt agtttatatt tgttttttat ttaatgtatt    21420
ttttaagtaa ttatgttttt gtggttgatt gaattttttt ataattttt gttgggaaat    21480
aaagatttttt tttaaattg aagaagtggt tttgttaatt aggggtattg tatttaattt    21540
gagagaaaaa gattaggaat gataggaatg atagtatatt tttaatattt aatagtttgt    21600
tatatatgtg aaagtaggat atatagtagg gaagtataat gttgagttga tttaaaatat    21660
taaatgtatt tgatatatta ttttttgaat ttttataatt ttagtttttt taaaggtttt    21720
tggattttta gaagttataa gggtagtttt tggtaaaggt ggttttattt ttaatttagt    21780
tatagagtta gtggaatgat ttttatattt aaatgttata ggggaattta ttgagaggaa    21840
aaagggtatt taaatttttt tggatgtttt aattaaaaat ttggattaat aaaattttttt    21900
taagtgtttt aaatttaagg aaagtaaata gtatttatt taattatatt tttaattagt    21960
atttattata gatataattt aaattagtaa tttggtatta gatgaattag atttattgtt    22020
atattatata atttttatgt ttattttgtt gtgtttggga ttttttttttt tttataataa    22080
agaatatgat ttataggtgt tatattttga ttttttgagaa attaatgtta tagaaaagtt    22140
gtttggaaag atataattgt gattttgtta ttgttttttgt tgttattatt ttttttttatg    22200
gggatgggta tatattttttt gagatttatt agattttattt tgtagtttat aaattattttt    22260
```

```
tttagatgta tttaatttgt tgtttagttt gttttttgta aaaaaattta gtgaatatat    22320
ttttaaaaat attttatgg ttttttttta ggtttgtgtg tatattttt ttgtgtgtgg      22380 tttttaatt ttattttgt tttttttgtg tttgttttaa gtatatttat ttagttttt       22440 ttatattgtt ttgtagtttt atatttag atttttaatt tgttgttgtg gttatttttt      22500
attgtgtttt gttttttat gtagtttata attttttttt tttttttgag atggagttgt     22560
gttttgttgt ttaggttgga gtgtagtggt atgattttgg tttattgtaa ttttgtttt     22620 ttgggtttag gtgattttt tgtttagtt ttttgaatag ttgggattat aggtgtttat      22680
tattatgttt agttaatttt tgtatttta gtagaaaagg ggttttgtta tgttagttag    22740 gttggttta aattttgat tttaagtgat ttgtttgttt gagtttta atgtgttggg       22800 attataggta tgagttattg tattttgttt gtagttata attttggtg gattttttt       22860 ttagaattt ttgtatttg tggagtaatt ttgtattttt ttggagttta gggattttaa     22920
atttttaggt tagtttttat tttatttat tttttgttt tgaggtttt atattataga      22980 tgtagtaaat atttagaatt tatattttgt aaggttgaag ttttgattta ttttatttaa   23040
gaaattattt ttttttattt ttttttaaa ggttttatta taggataggt ttttttgttg    23100
aatttgatgg tgggttgagt ttttattt ttttttaat aaatgtgata aatttttag       23160 attttttttt ttgtggattg tttttgttt tgtttttg tttattgtta taaagaaga       23220 taatgataat aaaatgataa taatataaat gtaaatgtat ttttttttt taatttttt     23280 atattattaa ttttttatga attaaggtgt gatatttgaa agttatattt gttttattag   23340
ttatatttat atagtttttt tgtttattg atgtatttt tatattattt tttatatta     23400 ttttttagg tttttttta ttttatgtta gtttagattt tttggtttt ttatttggag      23460 tgttatagta gtttttaagt tgttatttaa ttttatttt tgttttattt gtttgttaga   23520
aatttgaagt agatgtgttg ttgtaatgat attatatgtg ttatttttg tttggggt      23580 tttaaggttt ttaaggttat taaaatattg taataattaa ttgttttaat tgtatttgt    23640 atttattttt ttgttttgt taattaaaa tgttttaata ttttgttaat attgaatgtt     23700 gatgttttt tattttttt tttttatat gtttgtttat aattgtttat tgattatatt      23760 agttttaa tattaaaggt attagttata attttgatgt tatatagaat gataattaaa    23820
aggtgataaa tgttaatgat ttaattgagg agttgtttat tttataagt ttatttgagt   23880 ttagagaatt ggtaaaagat tggtgatttt tggttattat ttaaatataa ttggttaatg   23940 tagttttgg agattagtgg ttagtataat attttagtt gagtagggtt aaaaataatt   24000
atatttgttt aagttgtaga tattatttta ttgtatagta aagaatgtta aaatgttta   24060 atttagtata tgaagagtaa aatataaaaa taggtttttt ttattttta ttagtaagta   24120 aagtggtttg tattttgaa atatattttt tgtttaatta taataaaata taatataaat   24180
gttattaaaa gttttatttt atggatgaag atagtgatat ttagagatat taattagttt   24240
ttttaagatt atatatttat ttagtagtaa aagtaagttt ttataagttg atttatttta   24300
ttttagtttt tatttggaat tattaaattt atattttttt tagtaaaatt attgtttata   24360
tttttagggt tttaagagtt taatgttaaa tttgggagat ttattttaa attttttaa   24420 agtgtaaatat attttttta ggatgattat aaagttatta gatgtgtgtt aagtaatata   24480
tatagttata tattttgat taaaaagat ttttaggtta tatagaagag agatttatgg    24540
ttgagaaaaa ggtagattgt ttttaagaaa ggttttaaat atatttttt ttgataggtt   24600 ataggagagt tagttagatg aattattata gtgtgtataa aatgtttagt agaataattt   24660
```

```
tttagtattg gtagggaaga gtaataggag taatataaga gaaggaaagt tggtttgtag    24720
agtttgtttt agtatttgta ggggtgatga ggttgtttgg gttaagaatt ttttatatg    24780 ttttttgggg ataatttatt tagaattatt tttgtgtttt ttaggttatt taggtaatta    24840
ttattaatta gtaaatatag ataaaataga atattttgtt tggatttgtt tgttaaaaat    24900
taaatgatta taatttataa ttttaggaag atttgttatt aaatgaattt atgataaatg    24960
atttaaatga ttttttataaa gtagagtttg ttgtaatttt tagtatgaga agtatgaatt    25020
ttattattat tttttaaata ttttgagtta aatggattgt tttgtaaagt ttatgtttta    25080
tttttataga tagtttaaaa atagtttagt atttagtttg taggttggtt ttatttaagg    25140
agtttgaagt taggtaaggt gtttattatt atttatttag atttgttttt tggatatttt    25200
agttgttttt tttttttatg gttagggagg agagttatgt gtatagttta agaatgtgta    25260
tttttatgtt tttgaatagt tggttataga attggagtta ggtgttttt gtgttattgg    25320 tttttttttt tggtatgttt tttgggtggt tggagttagt tagtgtttga tttagtttta    25380
tagatttagt aatgaaattt ggagggtaga gtaggtaatt aggtatataa gaattgtaaa    25440
gtaatgttta tttggatagt tgattataat tataattttt taataatgta ataggaatat    25500
aaattgttag attttttata ttattgtaat ataaagaaga taattgaagg ttgtgaagat    25560
agtttatgaa atgtaaggaa gaattggata attaagtaat aggaagagta gagaaatagt    25620
gagattttgg gagttataag atttgggtgt ttaaattttg ttaggatttt tttgttattt    25680 ttattttgt tttttttttt tggttagttt ttttttgttt tttttatag attagttttt      25740 ttttatatgg atatgaaatg tttttaagtt ttatatttta ggggttttgt tattgaagga    25800
ggattagttt gatattttt tagatttata ttttaaggaa gatgaattat tagatttaag     25860
taattttgtg taattggaga agatttgtag atttttattta atgggttaag ttggatatgt    25920
atttgtggga gggagatatg ttttgtgggt ataatatata tgtaagtaaa ttttaatatt    25980
gtataagata tgtttttgaa aatttatttg tagtttgaaa atttggaagt taaatagtag    26040
attaattgtt gtgagtgtta gaatttagtg taatggtatt ttttgtgatt taggtaatt     26100 tgtataggta gaaagatttt tgaaagtttt atttaggttg gaaagggttt tgttagagg     26160 ttatgagtgg gattttttag gtatttgttt ttttatttta aggtttgtat atggattgga    26220
ataaaagttt tggtagttgt aattttttaaa tttttttta agggtattta gggatttaaa    26280
gtagtaggga atgtatttt ttatttttt ttgtttttt ttttattgta gtaagaggta       26340
agtatagttt ttagttttgt ttgtattttt ataggagatt tatgtatagg ttttgggttt    26400
tggttgtagg atagtgtgag gttgttgata gggtgagaga atggtgagaa taatggaata    26460
ggattgaggg agaaggaaga ggaattgttt ttagaattat tatttgggat ggtggtttta    26520
gggagtaaaa aatattttttg gagttttttt aaggggtttt ttggtagagt ggtattattg    26580
ttagatattg ttatggttgt aggtaggatt gattaaagaa ttttgattt ttttgtagga     26640 tagggtaaag ttttgaattg tttttagaga ttgtatttag atttatattt tggaattatt    26700
attttggttg tattgtgaat ggtaatgttt agggagtagg attggaggga aggagattat    26760
tatgtggttg ttgttttttgt ttaagtaggg aataatgatg gtggaatgtt tgtattggta    26820
gagaggagag agaggaggga tttggtgaat ttttggaggt attggtagga tttggtaata    26880
tattgaatgt ggagagtaaa tgggtaggga gttagtgata aagtttaggt gtttggtttt    26940
gatgattggt tatgtttgtg ttggttgtgt atagaattta gaggtttagt gttttttatgt    27000 gtagtgttgg ttttttatttt gtggtagttt ggtgtggagt tgagatgtgt tttttttatt    27060
```

```
ttatgtttat gttttttag ttagagtaaa gtatgtttgg ataatttagg ttttttttt   27120
tttttttttt ttttttttag agagagaggg ttttgtttt gttatttaga agaagtgtag   27180
tgttgtgatt atagtttatt gtagttttga attttggtt ttaagtgatt agaggattag   27240
gtgtattttt ttataaattt tttaaattt tttagtatt ttatttta agggattta   27300
tagtttttt tatttggatg gtgttatggt gttttattt attttgaga attgttttaa   27360
aattttatat agaaatttgt tattatgtat ttaaatgaga agaaatgttg aatttgtaat   27420
tttaattttt taagataaga gtttgtagtt tgtttttagt agagttaaag aaaagatat   27480
gatgaatggt ttatatattg aaaattgtag aagaaataat ttaatatgga atgggtgagg   27540
ttgttatagg tggtgtaaaa ataattgtgg tttttgttgt tattttagt ggtaaaaatt   27600
gtaattgttt ttgtataaat ttaataatat tgtttgaaat ttatattttt tggtggaata   27660
gttttgagat agagtgggaa ttagattatt ggtttataaa atagtatgta gttattgtta   27720
tttttttaatt ttatatttt attatgaggt aatgttttt ttatttgatt tggagaatgt   27780
ttttatttt tttttatata tttgtgaaaa ttaaatgtta aaggaattaa tataataatt   27840
attgttaaat tatgatgtaa aataatattg tgtttgtaat tagtttaggt agttttattt   27900
ggtttaataa tataaaatta ttaggtttat aatatttag tattttagtg tgattggtta   27960
agaaaaaat ttatgttatt ataaaagtt aaattaagta ataattaatt taaatttaa   28020
ggaaatataa agtaaagtat tatgttgtaa tatggaatat taatgtaaat aattttttaa   28080
tagtttatga aatagatttt gaattggtag ttgataaaga aaggttagtt ttggtttaat   28140
tttttttatgt tttaatattt tttttgaagt tttatttaat tttatttgtg ttagtaatag   28200
tattttgaga tggtggtgta tttggaaaat tattatttt ttttgataa ttagtatttt   28260
taatttaatt tttatatatg ttttttggaa atattatatt tatatttga tgatgtttta   28320
aaaataattt taatgtaata attatatatg tgtggtgagt aaattgtgtt ttgtaaaaga   28380
tattttaaa ttttaatgtt tgtatttggg aatgtgattt tatttggaaa tagggttttt   28440
gtaggtatga ttaagttaaa atgagatttt attggattag gatgggtttt aatataatga   28500
ttgttgtatt taagaggaaa atttgtatag agatatatat atatataaaa gaatgttatg   28560
taatgttagg tatggagaat attatgtgat aatgaaggta gagattggag tgatgtattt   28620
atgagttaag gatggttagt aattttaga agttggggag agataaagga tgtttttta   28680
ggatttttag agtaagtata aatttgttag tattttgatt taggatttt ttttttaga   28740
attgtgagaa tagattttag ttttaagtta tttagtttgt ggtattttgt tataggagtt   28800
ttaggaaatt aatgtaatat gttatgttgt aaataaatag tagttttaat tggtataaat   28860
aataatttta agtatatttt attattaggt taggtgagta ggaaattgtt tggtagatta   28920
attattaatg ttgtatttt tgaaaagtta aaatattttt atttagtaaa taatatttgt   28980
ttaaagttt ttatttgtat tgttttaaaa taaagtaaaa attaaaatgg agttagttat   29040
gtatttgaaa aatgtgaaaa aggaaagaaa aattttttag gaaagatttt ttttaaaatg   29100
gttatatatt tgagaaagaa ttttaaaatt taaattattt ggttgtttat tttatttttt   29160
tgtttatatt attagatata ttatgtatga ttttatatat tatgtatgtt atatttaatt   29220
aatatttatt aaatatttaa aatttgttag gtttgagtt aggtattgta gataggtaaa   29280
taagataaat atttttttt tttaaagaga ttattttggt atgaaattta atttgtagaa   29340
gaagtgaaag aggttatttg tagagtttat tatgaaaatt tatttttatt atttgttgta   29400
gttttatttg atttgtgaa attatttag tattatttgg ttttattttg tgttttgta   29460
```

```
ttatattgga gaaaataaaa tttatttatt gtatagataa tataaaatta attaaagtat   29520
gtgaaattaa aaatgtaatt gtttattaaa ttttttttag tgtttttat ttattagtat    29580 ttaaatatat ttttagttgt gtatttatgt tagtataatt aaaatgtggt gttttattt    29640 ttttatttaa tttataatta ataatgttta ttttttttatt ttttttttt gagatagagt   29700 tttattttgt tatatttagg ttggagtgta gtggtatgat tttggtatat tgtaatttt    29760 gtttttggg tttaagtgat ttttttgttt tagttttttg agtaattggg attataggtg    29820
tttgttatta tgtttggtta attttttgta ttttagtaga gatagggttt tattatgttg    29880
gttaggttgg ttttgaattt ttgattttag gtgatttgtt tattttggtt ttttaaagtg   29940
ttgggattat aggtatgaat tattatgttt ggttttttat tattttata att            29993
```

<210> SEQ ID NO 5
<211> LENGTH: 29993
<212> TYPE: DNA
<213> ORGANISM: Artificial Sequence
<220> FEATURE:
<223> OTHER INFORMATION: chemically treated genomic DNA (Homo sapiens)

<400> SEQUENCE: 5

```
aattataaaa atgatgaggg gttaggtgtg gtggtttatg tttgtaattt tagtattttg      60
ggaggttgag gtgggtggat tatttgaggt taggagtttg agattagttt gattaatatg     120
gtgaaatttt gttttatta aaatataaaa aattagttgg gtatggtggt gggtgtttgt      180
aattttaatt atttaggagg ttgaggtagg agaattgttt gaattaggga ggtggaggtt     240
gtagtgtgtt aagattatgt tattgtattt tagtttgggt gtgatagagt gagattttgt     300
tttaaaaaaa aaaagtggaa aagtgaatat tgttgattgt gaattagatg aaaaaataag     360
aatattatat tttagttatg ttaatatgga tgtataatta agaatgtatt tggatattga     420
tgaatgggaa atattaaaaa aaatttgata aataattata ttttggtttt tatatatttt    480
aattaatttt atgttgtttg tgtaataagt aaatttttatt ttttttaata taatatagaa    540
gtataaagta aaattaaatg atgttaaaat ggttttatag gattaggtaa aattatagta     600
gatagtgaaa atgaattttt atggtagatt ttgtaaatgg tttttttttat ttttttttata   660 gattaaattt tatgttaaaa taattttttt aggggaaggg aatgtttgtt ttatttattt     720 attttataata tttagtttaa ggtttagtaa attttaggta tttaataaat attgattgaa    780
tgtaatatat ataatgtatg aaattatata taatgtattt gataatgtaa ataaaaaaat     840
ggaataaata gttagatgat ttaagtttta aaatttttt ttaaatgtat agttatttta      900
ggaaaaattt ttttttaaaag atttttttt tttttttat atttttagg tatataattg       960 attttattt aattttgtt ttgttttagg ataatataga tagaaattt tagataagta        1020 ttatttattg aatgggaata ttttaatttt ttagaaaata taatattgat aattagttta     1080
ttaggtaatt ttttattat ttgatttaat aataaaatat atttaaaatt attatttata      1140
ttaattagaa ttattgttta tttataatat agtatgttgt attagttttt taggatttt      1200 ataataaagt attataaatt gggtggttta gaattgaaat ttattttat agttttggag      1260 gaaagaagtt ttaaattaag gtgttggtag atttatgttt gttttggaga ttttagggaa     1320
gtattttttg ttttttttta gttttgggg ttgttggtt attttggtt tatagatgta        1380 ttattttaat ttttgttttt attgttatat gatgtttttt gtgtttaatg ttatatggta    1440 ttttttttgtg tgtgtgtatg ttttttgtata aattttttt ttaagtataa tagttattgt    1500
attaggattt atttaattt agtaaaattt tattttaatt tgattatatt tgtaaagatt      1560
```

```
ttgttttaa atgaggttat attttaaat atagatatta ggatttaaaa gtattttta    1620
tggaatataa tttatttat atatatgtat aattattata ttgaaattat tttaagatg    1680
ttattaaagt atgaatgtaa tattttaga aagtatatgt aagaattaaa ttaaagatat    1740
tgattgttag gaaagaagtg ataatttttt agatgtatta ttattttaga gtattgttgt    1800
taatgtaagt gaaattaaat aagatttag gaaagatatt ggagtataag agaattaagt    1860
taaaattagt ttttttttgt taattgttag tttagaattt attttatgaa ttgttgggga    1920
gttatttata ttaatgtttt atgttataat ataatatttt gttttatatt tttttgaaat    1980
ttagattaat tgttatttgg tttgatttt tatggtaatg tgaattttt tttggttaa     2040
ttatattaag gtattaaaat attatgagtt tagtgatttt atattattga attaagtaaa    2100
attatttagg ttaattgtag atatagtatt atttatatt ataatttagt aatggttgtt    2160
atgttaattt ttttaatatt tagtttttat aaatatatga gaaaagatg agaatatttt    2220
ttaaattaag taagagaagt attatttat aataaagata taagattaag gaataatagt    2280
aattgtatgt tgttttatga gttaataatt tagtttttgt tttattttaa gattgtttta    2340
ttagaaaata tgaattttaa atagtattat taggtttgtg taaaaataat tgtggttttt    2400
gttattgaaa gtaatagtaa aaattgtaat tattttttgta ttatttgtag taatttatt    2460
tatttttatat tagattattt ttttttgtagt ttttaatata tagattattt attatatttt    2520
ttttttaat tttgttagaa gtgagttata aatttttgtt ttagaaaatt agaattataa    2580
atttaatatt tttttttatt taaatatata atagtaagtt tttatataaa gttttaagat    2640
aatttttaga aatggaatga ggtattatgg tgttgtttag gtgggagaga ttgtaaggtt    2700
ttttaaggaa tgagatgttg aaggaggttt gagaagtttg tagagaagta tatttaattt    2760
tttgattatt tgaggttagg agtttaaggt tgtagtgagt tatgattatg atattgtatt    2820
ttttttaggt gatagagtgg agattttttt tttttagaga aagaaagaa agaaagaaag    2880
aaatttaggt tgtttaggta tgttttgttt tggttaaaga aatgtgaata tggagtggag    2940
ggggtatatt ttaattttat attaggttgt tgtggaatga ggattgatgt tgtatatgga    3000
aatgttaaat ttttggattt tgtatataat tggtataggt atagttagtt attaaagtta    3060
aatatttagg ttttgttatt gatttttgt ttatttgttt tttatattta atatattatt    3120
aagtttatt aatattttta aagtttgtt aaatttttt tttttttttt tttgttagt      3180
ataggtgttt tgttattatt gtttttgtt tgggtaggag taatagttat gtaatggttt    3240
ttttttttt agttttgttt tttggatgtt attgttata gtgtaattag agtgatggtt    3300
ttgaaatata gatttgaatg tagttttaa aataattta gagttttatt ttgttttag      3360
aagaaattag aaattttta attagtttta tttgtagtta tggtagtgtt tagtggtagt    3420
attgttttgt taaaaggttt tttgaagggg tttaggggt gtttttgtt tttgggatt      3480
attgttttaa gtagtagttt tgggatgat ttttttttt tttttttag ttttgttta      3540
ttgttttgt tatttttg ttttgttagt agttttatat tgttttgtag ttagagtttg      3600
ggatttgtat atgagttttt tgtgagggta aagtagggt tgagggttat atttgttttt    3660
tgttgtagtg aaaaggaaaa taagggaaag tgggggagta tatttttat tgtttaaat     3720
ttttagatat ttttgggaaa agatttaaaa attgtagttg ttaaaatttt tgttttagtt    3780
tatgtgtaga ttttgggatg gggaaatagg tgtttgaaga gttttattta tgattttga    3840
tatagatttt ttttaatttg ggtggggttt taagaatttt ttttgtttat gtagagttgt    3900
ttgggttata gaaagtgtta ttatattaaa ttttaatatt tataatagtt ggtttattgt    3960
```

```
ttggtttta gatttttaaa ttgtaagtaa attttagaa gtgtattttg tataatatta    4020
aggtttgttt gtatgtgtat tatatttata aaatatattt tttttttata gatgtatatt    4080
tagtttaatt tattaggtag ggtttgtaag tttttttag ttgtatgaaa ttatttggat    4140
ttaatgattt attttttta ggatatgagt ttgggaaaat attaggttag ttttttttta    4200
gtggtaaaat tttaggata taaaatttgg aaatgttta tatttatgtg gaaaaaagtt    4260
ggtttgtagg gaaagataga agagaattga ttgagaaaga ggagtaaaaa tgaagatggt    4320
aagaaagttt tggtagaatt taagtattta gattttgtga tttttaaagt tttattgttt    4380
ttttgttttt tttgttgttt agttgttaa tttttttttg tattttatga gttattttta    4440
tggtttttaa ttattttttt tatattgtaa tggtatagga agtttaatag tttatatttt    4500
tgttatatta ttgagaagtt atagttgtga ttaattgttt agatgggtat tgttttataa    4560
tttttgtgta tttagttatt tatttgttt tttaaatttt attattgggt ttgtgaagtt    4620
ggattaggta ttggttggtt ttaattattt gggaagtatg ttagagagga aagttaatgg    4680
tataaagaat atttagtttt aatttatgg ttaattgttt agagatatgg agatgtatat    4740
ttttggatta tgtatatgat ttttttttt ggttgtagaa aagaaaaata gttgaggtgt    4800
ttaagaaata gatttggatg aatagtaatg agtattttgt ttgattttaa gtttttaaa    4860 tggagttaat ttataaatta gatgttgagt tattttgag ttgtttataa agatagaata    4920
tggattttgt aaaatggtt atttaattta aaatgtttaa aaatgataa tggggtttat    4980 attttttatg ttaaaagtta taataagttt tattttgtga gaattatttg ggttatttgt    5040
tataagttta tttgatggta agtttttttg gaattataaa ttatgattat ttgatttttg    5100
ataagtaggt ttaaataagg tgttttattt tgtttgtgtt tgttaattgg tgatggttgt    5160
ttagatagtt tagaaaatat agaagtaatt ttgagtgaat tgttttaggg agatatgtga    5220
aagaattttt agtttaagta atttattat ttttatggat attaaggtag attttgtaga    5280 ttaattttt tttttttgtg ttattttat tgttttttt tattagtatt gagaaattat    5340
tttgttgagt attttgtata tattgtaatg gtttatttag ttggtttttt tgtagtttgt    5400
tagaagagaa tatatttgaa gttttttta gaagtaattt gttttttttt tagttataaa    5460
tttttttttt gtgtaatttg gaaatttttt ttgattaaga gtatatgatt atatatattg    5520
tttaatatat atttgatgat tttatgatta ttttgaggaa aatgtgttgt atttgagag    5580 aatttaagaa tagattttt aagtttagta ttgaattttt gaaatttag aaatgtaaat    5640 gatagttttg ttaagggaa tgtaagttta gtgattttaa ataagattg gaataaaata    5700 gattagtttg tgaaaatttg tttttattat tggataaatg tatgattttg gaaaagttaa    5760
ttaatatttt taaatattat tgtttttatt tataaaatag ggtttttaat aatatttgta    5820
ttatattttg ttatgattaa ataaaaaata tatttaaaa atatagatta ttttgtttgt    5880
tagtgagagt ggaagaaaat ttgttttat attttgtttt ttatatattg aattaaaata    5940
ttttaatatt ttttgttgta tagtagagta gtatttgtaa tttaaataaa tgtaattatt    6000
tttaattttg tttaattaag agtattatat taattattga tttttaggag ttatattaat    6060
taattatatt tagatagtag ttaaaagtta ttagttttt attaattttt tgaatttagg    6120
taagtttgta aaaatgaata attttttgat taagttatta gtatttgtta ttttttagtt    6180
gttattttgt ataatattaa agttgtgatt ggtgttttta gtgttgagag attgatataa    6240
ttaataaata attatagatg gatatgtgaa agaaagggga ataggaaagt attagtatttt    6300 agtattaata ggatgttaag atattttaag ttggtaaaag taggagaata agtataaaat    6360
```

```
ataattaaga taattggtta ttataatatt ttgataattt taaaagttttt aaaatttttta   6420 aaataaagaa tggtatatgt gatattattg taataatata tttattttag atttttgata   6480
aataagatga ataagaagtg gagttaagtg gtaatttaaa ggttgttgtg atgttttaag   6540
tgagaagtta agagaattta gattgatatg gggtggaaaa aggtttggag aagtggatat   6600
gagggataat atgagagata tattaataag ataaggaat tatatgaata taattgataa   6660
ggtaaatgtg atttttaggt attatatttt aatttatgag aaattgatga tatggaaaag   6720
ttaagaggaa aaggtatgtt tatatttgtg ttgttattgt tttgttgtta ttattttttt   6780
ttatggtgat gggtaggaag taaaagtaag aggtaattta tagaggaagg agtttaaaaa   6840
gtttgttata tttattggag gggggataga aaaatttggt ttattattag atttagtaaa   6900
gaagtttgtt ttatgatgga gttttttggga agagaataaa agaaaataat tttttgagtg   6960
agataaatta aaattttagt tttgtaggat gtaaattttta aatgtttatt gtatttgtgg   7020
tatgaaaatt ttaagataaa aaaataaat aaaataaaga ttgatttaga ggtttgaaat   7080
ttttagattt taggggaatg taaaattgtt ttatagagta taaagggttt taagagagaa   7140
atttattaaa agttataaat tataggtgag gtgtggtggt ttatgtttgt aattttagta   7200
tattgggagg tttaggtagg tagattattt gaggttagga gtttgaggtt agtttggtta   7260
atatggtgaa atttttttt tattaaaaat ataaaagtta gttgggtatg gtggtgggta   7320
tttgtgattt tagttatttg ggaggttgag gtaggagaat tgtttgaatt taggaggtag   7380
agattgtagt aagttaagat tgtgttattg tatttagtt tgggtaatag agtataattt   7440 tatttaaaa agaaaaaaaa aattataagt tatataaga aataaaatat agtagagagt   7500
agttataata ataaattagg aatttaagaa tgtgaaatta tagagtaatg tggaaaaaat   7560
tagataggta tatttaaaat agatataaaa gaaatagaaa taaaattgaa aagttatata   7620
tgaaaaaaat atatatataa atttggaaga gaattataaa aatgttttta aaatatatt   7680 tattgaattt ttttataaga aataaattaa atagtaaatt agatatattt aaagaaataa   7740
tttatgaatt ataaggtaaa tttggtaaat tttaagaagt gtgtgtttat tttttataaaa   7800 gaaaataatg ataataaaaa taataataaa attataatta tattttttta aataattttt   7860
ttataatatt aattttttag gaattaaggt gtgatatttg tgagttatat tttttattat   7920
ggggagggag aagttttaaa tataataaag taaatgagag agttatataa tatggtaata   7980
aatttgattt atttaatgtt aagttattga tttgaattgt gtttatagtg aatattaatt   8040
aagaatgtaa ttaaataaga tgttgtttgt ttttttttaaa tttgggatat ttgaggaaat   8100
tttattgatt tagattttta attgaggtat ttaggaaagt ttgagtattt tttttttttt   8160
taataaattt ttttgtagta tttgaatata aaaattattt tattgattt gtaattgaat   8220 tagaagtagg gttattttta ttaaaaattg ttttatagt ttttaaaaat ttaaagattt   8280 ttaaagggt tgaagttgta agaatttaga aaataatgta ttaaatatat ttggtgtttt   8340
gagttaattt aatgttatgt ttttttgtta tgtgttttgt ttttatatgt atggtaggtt   8400
gttagatatt aggagtatgt tgttattttt gttattttta attttttttt tttaagttaa   8460
gtatggtgtt tttggttaat aagattattt ttttaattta aaaaaaaatt tttgttttt   8520 aatagggaat tataagggaa tttagttagt tataaaagta taattgttta ggaaatgtat   8580
taagtggaag gtagatataa attaggttat agtgtattat tattttaaa ttatttaatt   8640 ataaattgat gtattaatat agattaatat taatgtatat taaagtatta tatttatatt   8700
taaataaaaa tgtaaaggaa aattaattag ttgaaataga aattaatgat gataattttt   8760
```

```
aaagtagtaa gaatgtattt ttgagaaaga ttttagggtt ttgtttgttt gtttgttgga    8820
gattaaatta ttttttagta aaattgaagg gggaaaaaag attaatgttt aagttatagg    8880
aagatgtggt ttgtttggta tttggatgtt ttttgtagaa tttataagtt tatttttag     8940
gggtttaaat gttttggat ttaaaaagtt tttgggaaag aatttttta agggaagaga      9000
tggagagtta tataagtaga aattaagttt gagttttaag ttttggggtt gtaagaaaag    9060
aataagagaa taagttaaaa aagttgttta ttaaattttt tatagaaggg gaggagggta    9120
ggtgttatta ttatgtattt tgaagttttt gttatagggt attggattga gggaagttgt    9180
tagatatttt ttttattta aattatttgt aattttagta gtttgattaa aaaatataat    9240
tttgtaagtt gatggaaaga aatgaatttg gtgaagaaag tgtgggaaaa tattggttaa    9300
attagtaaga aaaagattgt aataaaaaag aattaaagt gtgagaattg aaattaggaa     9360
gatggtagaa tgagaagtag aataatttgt tttttttttt ttgattgaat taaatgtaaa    9420
gatattaggt ggtagagatg tggatattag ttttttatagt attttttaag agtgttatgg   9480
ttttttttg ttttttatttt atgttttagg tatttttttt agggttttag ttaagttttt    9540
gtttaagtat ttgaataaat tagatttatt tttgaattag ttttaggtgt tgtttataga    9600
tattgttatg gtttatattt ggataattta gtttggtttt tttaatgttt taatttttt    9660
tttatgattg tgaaaaaaat gtaatgagtt tttttgaaga aatatttaag atatataaat    9720
ttagaatatt tatagttttt aaattaagat tgtattatat aaaaatattg attttttaa    9780
aatgtatgaa tgagtgaatg agtgtataaa tagttaatag tgtataaatg tatgtatgaa   9840
tgaatgaatg agagtataaa taagtaaata aggaaatata tttttaaagt atatgttagg    9900
aaatggataa attatgtttt atgaagttttt agattgaatt aggtaaatag aattgtagat    9960
ttttatgttt gttatgattt agtgtatagt tttgggaaaa ttttgtaatt tttttatatt   10020
ttagttttttt attttataaa aggagtatat tgtttgaaat ttaatttttt tatagtagtg   10080
agagttttga tttaatgttt ataaaatgtt ttttagttttt ttttgattaat aggtaaaata   10140
ttgtggtagt ttgtataata tattttttaa aaaggataaa ggtaattggt tgaatttgat    10200
gtaaaataat attttattta agaaataaat attagttata tttattattt ttttattta     10260
tttgttaagt aataaaaatt attttttaata gaaaagtatt aaattaatat ttaagttagt    10320
tgaagtgtta ttattatagg ttttatttat gttgggggaa ggagagttgt tttgtttttt    10380
taggttatt tatatgttta tatggtaaag ttaggaatgt tgggtatagt tttgaaggtt    10440
tttagtgtat ttattggttt ttggtatttt aatgtatttt attttataa ttataaaagt     10500
attttgagt gttttggaa atatataata aattttaat taatttaaga gtgttttaat      10560
tgtatatatg aaaattttg ggaggaaaat attagttatt ttatatatat atagtattta     10620
agttagtaag agagtttttt ttgaaaggta taaagtagtt ttttatagt aatataattt     10680
ttagttttat atgtgtaagt tttattgaat ttttagaat aataggaaat tttgtaggaa     10740
aaaaatttt ataaaaattg atagttatat ttatttaatg taagaggaat atattagtta     10800
ttttgagttg gattattttt taaaggtatt agataattat tgaagattaa ttaaattttt    10860
aattaaaaat tataagaatt gaatatttg gagatagaat tttttatata taaaaattga    10920
ataataaaat taattgatta atatatttta ttttaaaatt gtatttatta gatttttta    10980
gttagtattt gagtagtaat tttttggatt ttgatgtatt aattttatt tttatattaa    11040
atagattata ataagtaata gatttataaa ttagttattg atatgatata attgatattg   11100
tgatatgtat aataatattt attaatatat ttataatgga gtaatgttat ttattattta   11160
```

```
tataatgttt atatttttta tttttatgtt aaaaagttat tgtaatatat gtaaggtgtt    11220
tagaattgtg tttggtatag agtaggtttt tattagaata ataatatatt attttttata    11280 agttttatt aattatatga gagttagaat tatttttttt aataattttg gtaaatattt    11340
gatggtatta agtaaaaaaa aatgtagtga atataatatt attgatttat tttttttaa    11400 tatttgggtt tatgaattat aagtaaatat aatatgtatt tataaaaatg aatattaaat    11460 attttaagt gagaaattaa ttatataaat tatatgtata tattaaatat atattgttaa    11520
tagaattatt tattttaatt atagtggagt attttgatta ttatatgagt tttaaggaat    11580
ttattattat aattattttt tttaattaga gtataaataa ttataaggtt taattaagtt    11640 gaaattttg tatttggttt ttgtgagaaa gatgagaata ttattttaaa gatgtaagat    11700
ttataaattt ttttaaaaag tattttggta ttttttatgg aaaatgtata tatatattta    11760
tttattaata ttgtatttag agttttattt atagatattt ttggtagatg tatgaagaga    11820
tataaaaatt attagtgtaa tatatttagt aatagtaaaa atatggaagt aatgtaaata    11880
tatattaaga ggggaatagt gaaattatga aatatttgta tatattaaat agaagtattt    11940
aaaattatat gtattgatgt ggaaaaatat ttaagattta gtagattaaa agtaagtttt    12000
aaggaaatta atgattttat tggagttaaa aatgtaaaat gaaataaaat tatattttta    12060
tatagttatt atatttatat atatatagaa aaaaaaatgt ttgaaaagat gtatatttaa    12120
gtataataat ttatttgat ttgtagagaa taagaatgag taaatttatt ttttatttta    12180
aatatatttg tatttttaaa attttttaag aaagtataat atatgtatag taaaataaaa    12240
tatataaatt aaaagttgat tattgatgaa ttttttattga ataaatattt ttatatgatt    12300
agtaattaaa ttaagataaa agatataatt agtattttaa agttttttt ttgtttttt    12360 tggttatttt ttttaaaagt aatttttatt attttgtttt taatatgtta tataaagtat    12420
gatttatttg tatttttaa gtaatagatt aaaaaaaaaa atttgtttta gtagtatgaa    12480 ttttttttt tgaatattaa atatatttag tattttattt taagatatta atttaaatta    12540
taatttgagt tttatagtg ggttaggtat tgaattaaat gtttttttg tatgaattta    12600 attattttt ataattttat gaggtgagta ttgttattat ttttatgta tatatgttgg    12660 aattatggtt tatagttatt tagaaaatta tatgattaaa gttatattgt tgatgagtgg    12720
tagagtttgg atatatataa aggtagtttg attttagtat ttttaatttt ttattagaaa    12780
taaataaata aaaataaagt ggtaagatgt agagttggga gtatgaagtg tttttagtat    12840
gaagtttttt ttttttgttt tgttttgagt aaatgattta aggttttaag gttatataat    12900
ataatatttt atttgtaaaa tggaagggtt aggttagatt tttttttga tttgattatt    12960 tgatgttgat aaataaagtg atttattgaa atatagagta aatatgtttt gttatgatgt    13020
agtgtaatta tgtattgtat tatgttaaaa aatgatttat ataagaaaat aaaattataa    13080
tttttgaaat tattggaaat aataattta atttaatgtt attttggat ataggaagat    13140 tttttttt aaataagtaa attggtggtt tttgaagggt tttgtttatt tttgtatgga    13200
aaatgtttaa aaataaatta ttaaaaatta aataaaattt ttttattttt ttaattgtgt    13260
ttgaaaaaaa agatgtaatt tttttagta aaaggttatg tatatttta atagatatat    13320 ttgggatttt tggttttat attttgaaat attgatataa ataaatatag aatatgtttt    13380 ttttaaatg aaatttataa ttttgagggt taaaaatttt ttaaaataat atgaaattga    13440
ttttagtaga aggtaattaa agagattaag gtttgtttt ggagaaaatt agaattatga    13500
agattataaa ttttaatgag aaatttgttt tttaaatgtt agtttattga aaatattaat    13560
```

```
gtatgttgga tatatttgtt tttttattag aaaattagta atattttggt ataaatgagg    13620
ttttaaataa gttggagtag aaaataatta ataaattagt tttatgatt ataagtaaaa     13680 gagaattagt tttttaaaaa gttaatagga tttattttt gtagatgttt ggtttgggat     13740
ttaatgtttt ttaaagatat gtatggaata gtgtagttat ttaattttta ttaatatttt    13800
taggtgttga ggttatggag ggaaaaagat atgattttt tttttgtga gtttatagtt      13860 tttttagaag atagatatat ataatgagtt ttaatataat ttgttgttat attaatagtt    13920 taaaaaagt gttatggtat tatatagaga aaagaattaa ttttgtttga gttttaagga     13980
aggttttata gaggaggtga tatttgagtt aagttttgaa agatgagtag attattatta   14040
ttattattat tttgtttagg taggtagtaa aagagtatta ggtaagtagg ttaagggagt    14100
tggggttatg gaggataagg gtggtgagaa tatgttaggg agaaaaaagg aagtgattga    14160
tggtattata agaaataaaa tgtttataag taagttttat tatattagga tttattatat    14220
aaagaattaa tttgagaaag gagatatgtg atttgaatat tttgtggggt ttttgattt     14280 atgaatttag gaagtgttta tttggaaaaa tagaattttt gggttttgg ttgttttta      14340 gtaattaaag ggttattagg ttttttgttt aatatttggt ataaagtgtt tggatggatt    14400
tgtggtttgt tgtgttttt ttggattttt tgtttatgaa tgaagtagaa ttttttta      14460 ttatttgtga tttaaatttt tgttttaaat ttttgtaat attttttgag aatggttttt    14520
atttgttatt gggttgttta gtatttattt tattttttg ttaataagga gttatgtagg    14580 gtttttttt atttaggaaa tagaaaaata ttttggttaa atatagtatg ttgtatttgt     14640
agttttttgt tatttaagta tatattttaa aattaaagta taaattaaag gaagtgagag    14700
agagagagtg agtgtgtgtg tgtgtgtgtg tgtgtgtgtg tgtgtgtgtt                14760
tttaagtatt tttatttgt ttatttaggt attaattagt aaatgatgtg aaattttag      14820 gttagtttga ttgtttttat gattatttat ttaatataat taaagtataa ttattaaatt    14880
agataatgta aagtgtgga attttaagta tttttgtaat ttttaataag ataaaaatta    14940
tttattgttt agaattttta agaaaattag tttaattata tatttataat attaatgttt    15000
tatattttag aataatttg aaatttaatt taaaattat atgggaaaag ttatttttt       15060 ttattttatg tgaatattat tgttttatt ttgtttaagt gattttgaa atgtgtttta      15120 tatatgttta aattatgtaa gggtggtgtt taaataatag ttaaatttat ttatattaat   15180
tatatattat tttatagata aaatgtattg gttaatatta aatttataga atgagaattt    15240 aaagtttgg atttgagaat ttataaaaga gagttttat atgtaatata tttatttta      15300 tttttttta gttgtataaa tgttattaat ttaagattt gaatttgtgg ttataattga     15360 aagtatata taattttttt gaaaattttt tattataaat aaataattta atttattaag    15420
tattttaatt tttagtagtt gtgattatta gtaatttat tttttttaat attatagatt   15480
aaataaaata aaagtttttt attattgaat attttattat agaaatggaa aggtaatggt   15540
tattatttaa aaataaattt aaattattta ttgataaata attggaagaa aagatatata   15600
gatgatttaa ataaatattt attttttata tatttttttt taggtatttt gttattttta   15660
tttatatatt attttagaa aaggaaaata tgttggagat ggttaatttg tgtgaagtgt   15720
atttgtaaat ttttttgtg taaagttaat ttattaaat agattaatga gaattgtttg    15780
attttatgtt taaatttggg aggaaggtat taggattttt tatatttgat tggaaataga   15840 ataattttt tatgtagagt tttgggagtt ttttgattat attaaatgat attaagattt   15900
gtttaggtta tgggttttta agaagaggta attttgtttt tagagattat ttgataatgt   15960
```

```
ttggagatat tattattatt aggggaggga gggttttgg tatttagtga tgttattaag    16020
tattttatta ggtataggat agtattttt gaataaatta tttagtttaa aatgttaata    16080
attagagttt gaaaaatttt tatttaaata tattgaagaa tttaggtata atgttattat   16140
ttttaaaatt atatagatat atttggtagt agttttagat aagttgtaaa aatgagattt   16200
tgataattaa tattttaatt tttttttttt tttagttttt attttgttat atagttatta   16260
tatttgaatt taagtgataa attttgtaag tagaggtatt aattattttt tattgttttt   16320
ttaaaggtaa gaattatagt aatatgtaaa gttattttt aaaagttta tattgagttt     16380
attaggttta ttgattattg aaaattatat aaatttttat aattggtatt ttatggttga   16440
aaaaaagta attgaggaaa tttaaatatt ggttataaag tattattatt atataatgtg    16500
tttataattg tttaaagtag ttaaggaatt atatagatta aagttttaaa ataatttaga   16560
ttattgtatg tggaaatatt tattaaaaga aatattattg tataatgtaa atggttaatg   16620
ttaattgttg agtattata gtgttttttt ttaaggtttt aaatataatt ttagatttgt    16680
taagatgatt tatagtattt aatttatatt tggattattg gatattttat ttatggttat   16740
taatttatag tttttaaaa aagatttta gttttaaata ttttggaat atttgggggt      16800
aatttaatga aagatattta attatagtaa taataattga tatttatatt aagtattatt   16860
ttaaatatat ttatatatat ttatttattg aattttatt agaattttat gaggtatgtt    16920
ttgttatata tgagaaattg aagtaaaatt tgttttagta atgtgtttga tgttataaat   16980
ttattaatgt tagagttgag gtttgaattt aagtgtttgg ttttatattt ttttttttt    17040
ttatttattt atttatttt gagatggagt tttatttgt tgtttaggtt ggagtgtaat     17100
ggtgtaattt tagtttattg taattttgt ttttgggtt taagtgattt ttttgtttta    17160
gttttttgag tagttgggat tataggtgtt tattattatg tttagttaat ttttgtattt   17220
ttagtagaga tggggttttg ttattttggt taggttggtt ttgaattttt gatttaggt    17280
gatttatttg ttttggtttt ttaaagtgtt gggattataa gtgtgagtta ttgtgtttag   17340
tttttatatt ttttttattt atttattgtg ttataagaat tgagttttt agattttaag   17400
tattatgaaa ttattgtatt tttagagatt tttaggattt ttggtttatt tattagatta   17460
ttgatttttt agtggtaaga aataaatata tttttatatt tatgtatata tatatataat   17520
ttaagtttgg atttatagtt gtaatttat tgggtttata ttaaaattt ttgaggttgt    17580
tattgaggta gttttatttt gtaatagtta ttgttttttt tattgttttt agttttaagg   17640
agggatgtt tagtgttata attttgttt ttattttag tattttatt tatttattta      17700
atgggaatat aataattatt tattgattat atgtttagta gtgtattgtg tattagtgat   17760
atagaaatga taaatatagt taattttttt agtaaattt tagtttaaag taggatttag    17820
attaatgtaa tttattatat tttaatgtgg taagggttat gttaaatgta gaagttggat   17880
gttttgggag taataagaaa gaaatgttta atttagattt tggaggttag aggaatttat   17940
tagaggagtt aatatttgt attttaagta ttgaaaaagt agtagaaaag atatttgtag   18000
ggggagaggg gtgatgtttt ttagagaaaa agtattttat gtataaagaa atgaagtgga   18060
aatgtttaag gtgtatttga gaattgtagt tttttatata gttggaaaag agagttgttg   18120
tgagtgggga gtgagagatg agaagagtaa tttgagtaag gttttttagta tgaagggtta   18180
ttttttttgt agagaatttt ggaatttgtt ttataggtag taggtaaatt ttttaaggaa   18240
ttttaagttt aggagggatt ttataaaaat tatgaataaa tgtggttgaa tattttaggg   18300
atgtgagaga gtgttagaga tagttttaat atagtttaga atgggttttt aggagaggta   18360
```

```
ttaagatatt ataattatat ttgttatgat aatattaata tgaataagtg tgtataggat    18420
aattgtttat ttaaagttaa tttgaatatt tgaggattag atttgtgatt ttggttataa    18480 tgatttttt  tttaaatatt tttgggaatg gtatgtaaaa ataagaat  ataataaaag    18540 ttttaaagtt tttaaagtta tgtagagtag aaaagaaatt tatttatttt attttaattt    18600
tgtaagtttt tagtaatatt gataaggaaa aagtatttaa taagtattta ttaagtattt    18660
ataattttgt taattatttt tatgaatgaa attttttaaaa attaaagtta ataattaagg   18720 gaaaaatta  gatttaaatt aaaattttt  atgagttaat taagaaaaat aatagtatta    18780 ttatttatt  aattaaagtt aatgtaaaaa taaataaata aaaaaaaaaa taaaataaaa    18840
tagtagaatt gttgttttg  ataggtttat tgaggtttgt atgtttaagt tatttattag    18900
aagtattgtt ttagattatt ggaaaatttg taaaaggaaa tttgaatgtg atttatttat    18960
aatgttatta aatttagtaa gaatgatttg agttataatt gtatatgaat atatatttgt    19020
atttaaatgt aagagaaaag aattaggtaa tgtagagatt tgttgatttt tttaagttat    19080
tattattttt aatatattga aaatattaag ttagaaatat ttaatttttt aattagaata    19140
tttggttttt tttaaatttt ttaatattag ggagtttaaa gttagaggtg aaatgtaatg    19200
aatagattat tttgttgggt atatgtagag gtttgtgaat tgtatatatg attttgtgta    19260
taatgagttt ttttggtatg tggtatattt atttgattag ggatagaatt ttaaatttg    19320 tattgttgtt tttgtgagta gaattaaatt taatggtata tgaatgtaaa tttttatgat    19380
ttaattgtag ttttttataa gaaatgtttt tttattttta aaagaaagg  gggaaaggat    19440 aatagaaata gtagtaataa tttatgtgaa aatttaaagt tatgttaagt taggttattg    19500
ttggtgtttt tttttatagt ttttaaagga ggaaagatgt tttaattaat aaagttaatt    19560
tttgtaggta taagttttt  gtgttttatt tagatttgta attatatata gggaatattt    19620
tgattagttt taattttttt agtgttaaat tgaatttgaa gattggttaa tatggatatt    19680
taagttatag aagggagagt agatatattt ttttgttgat atgttatatt gggagatatt    19740
ttattgtatt tgatagtttg ttttttagtg atgttatatg aatatgttag ggtaggtatt    19800
ttgaattaat tttttttgtt agaagatttg aattttttg  tagtagtttt tatatattga    19860
agatatttag agagaatttt agaggtggtg gttattgtga gagggtattg ttggtgagtt    19920
atttttaggt tatttatatt ttgttttatt tagagtagtg gtatattttt ttattgggta    19980
tattattagt tttatttaa  atgaaaggat ttgtggttga gtatataagt aaataaaaaa    20040
atgaaaatta ttgtttagt  ggaaaatat  tataaaattg taaaataggt tattaatagt    20100
aaaagtattt atttatagaa aattttatat atgtgataat tagataaatt gaatgtattt    20160
ttaaaatatg ggtagtttta ttataattta aatttgtttt tagaagttta ttatgtattt    20220
tttaattttt taagttttat tagttggttt aatataaatg tgtagatttg agatttaaaa    20280
ttagtattaa aataataaaa aataaaaata aagaaaatat aaagttgata atatttaatt    20340
aatttggata aggtttgaag agtaaaggaa gattttatat gttagttaaa tatttaaaag    20400
atttggttat aagttttga  taattgggaa atattataaa atatagtatt ttttaaatt    20460 tagttatttg ttgtttagtt tttatgattg tggttattta ggttatattt tgtttattg    20520 ttatttaata tgtttttta  gatatttaat ttttttttt  tgattttaat attttgtttg    20580
gttttgtttt aaataatatt gtttatgaag ttataggttt aatataaaat ttaataaatt    20640
tttttaatat ttagttattt ttatataaaa tataagtatt attaaaataa aatgtttagg    20700
tattatttaa aaatggtggt atatgattga tggaagtaag agtttagtat atgtttaagg    20760
```

```
ataagggtgt tggttttata ttggggagtt aggattttgg ttttattgtg ttgtatgatt    20820
gggttttagt ttttttattt gtaaaatagg aataataaaa gtatttaatt tatggtatag    20880
ttaagaagat taaaattagt taatttatat aaatgtttaa aatagtgttt tgtatgaaat    20940
ttttgagtaa atgttagtta tgatgttatg atggtgatag tgattaatat tatagtaata    21000
atgatagtta aattgtaatt atttaaagat tatagtgatt atttttattt aaaaatatat    21060
tttaggatat aaatatattt aagaaaatat gttttatat ttgatattta tattaatata    21120
tgttttggtg atataaaagt tattttatat tggtttaatg taattttatt ttgaaaatat    21180
ttatgtgata ataggaatta gattttgttt aaaaattata atttaaataa attatttgtg    21240
tagaaaaaaa aaaattaaaa aattttaata tgatagaata tataggtttt tttttattg    21300 tttaaaagta tgttaaaata aatttattta ttgtatgtaa ataaaagttt taaaaatatg    21360
aatatattgt attaaaatat tttatattgg aaaaaaatga gaattttgg tattttagaa    21420 tggtgttttt ttttattatt tatgtattga aattttaggg taagaaaagg gttagattaa    21480
ttttgaaagg ttttaaatat taaattatat tattgtgtta gtattttaag attaattagt    21540
attttttaat gataaaaaag gttatagtga gatttagagg tgtattttt gaaattgttt    21600 taaattatta tataaatgtg gttttgataa tataaaatgg ttttattttt aaattaatta    21660
gttttatttt tttttttgga ggtgtgaaag gggttagggg agtaagaata gtagtgttta    21720
tttttagtat ttttttatta ataaaaagat ggatggagaa atattaagaa tgataaattt    21780
taagtgtaaa atgatatatt attaaagtat atattaatgt atagttttat aagtaatatt    21840
gagtgatagt aatgtttata aagttttaa attttttaaa agtaattaaa gttgtttgta    21900
ttttttttga atgtgtaatt tttgtttatt ttttttttatt taagtttaag ttaaatgatg    21960
ttaagtttgg tttttaaaaat gatttaatga ttatgtagtg ttttttttat taaaatatat    22020
ttaattataa gatgtagtat tatatatatt gtatttttatt tattttttagg gtaaatgttt    22080 gaaatagtat gttatttttt agtttagtag gaaaaattta tgagagaagt aggtatattg    22140
taatgttatt ttattttttt ggtgttgatt ttttttattt agtaattatt gtaataaaat    22200
tttttaattg tattttgaa tataattagt ttaagatatt ttataggag gtatgttata    22260 agagtttagt atttagtata tgtaagaata atatttattt agaaaaagaa attgttaaga    22320
ttatattttt attgaaaaaa gaagaaggtg ttttgataga ggtttgttta gttttttaat    22380
gagaggattt aaaatgtttt ttattttga tagtatattt ttttatttat tttttaaata    22440
agtgatttga aatatttata attagatagt atttaatttt aggttttaag tgttttaata    22500
gttttatgaa atatgattag tagttgtaat atagaattat ggtgaataaa ttttttataa    22560 agagggttt gttttatag aatgtttagt gttttttgtat ttatttaata gaaaaaaatg    22620
ataatgagaa agtataatat atatttgtat ttttaaatta tttaatattt aattaagtag    22680
tgaaaaagat tattattttt tttttttgaaa tttgtataaa aattgtgagt ttttgtgggg    22740
taaaataagt ttgattattt gaaagttaga atgtgaattt tttaatattt taatttttta    22800
taataatagt tattgtttt ttgttatttt atttttttaa aaattttaaa aaatttaatt    22860
ttagtgtata aaatgttaaa atgaaatatt aagttatata aatatatttt tagatatgat    22920
attagttatt tagagtttgt aatagagatt gaaaatatga aattggatat ttattttttt    22980
gtggttatgt aaaattttatt tatattttaa agtataatat aaataaaaag gaaatttta    23040 gaaatggagt atttgttttt tttttttttt ttttaattta aagagtttta ttaaaagaaa    23100
aaaataaatt atagtaaaat gataagtaat ttatttgtta gttatttgtt aaaaaagaaa    23160
```

```
tttttatgta attttttttt ttagttttta gaaattttttt gaaatttagt atttattttt    23220
tttaataatt aataattatt attttttttt atataattat ttttttttat ataaatttta    23280
agattttaaa aatttttaaaa tttaagttta ttatttaaaa gaagtgttaa ttgtgagtat    23340
atatatatat gtgagatgtt ttattttgga aatgagaaat ttaattttaa atatttaata    23400
aatattaata aaagaaaat aattgagtaa attttatttt agttataatt gtgaattaat    23460
tggtagttat aatggttttt aaatattgaa atatattatt tttaggaaat ttataaagga    23520
aaataggttt ttgaaaatta tattgattgt agattttat ttattatgaa agataagtat    23580
atattattaa taattagaga aaggagatat ttttaataaa tttaattatg ttgttttta    23640 agttgtagtt gttaaaggtt ttaatatttt tgtatagtta tttttaaata tgggtttaat    23700
tttgaatgat ttataatttt taattaggtg gaataaatta tttttatggt ttataataat    23760
aaatgtgggt gtagttatgt ttgtttttga tattgttgtt ataaaaatta gattttggta    23820
gttttgtttt atataaaata atttgttttt tgttattatt gttttttgtt ttttgggata    23880
atgttatttt taaaaatata taaatgtttt tgaatgtagt tttttaaaat gttttgtatt    23940
atgtattaaa tatttttttgg ggggattttt ttttttatttt ttttagtttt tggttttta    24000 ggtttaagtt tgttaataat attttaaaag ataaaaaaaa aaaaaaggt attgattttg    24060 tttaaaatta aattgtattt gggaaaggaa tttaagtata atttttttttt taaggttta    24120 aaaataaaaa taatgtaata aataaaaaaa ttattgttaa tttttaatttt tgttagttat    24180 ttatgtgtaa gtgaaattttt agaagttgtt gatggggagt ttgtggttgt taaatgtttt    24240
taagattttt atttaaattt tgtaggagtt tgtattgaaa ttgataaata tttgagggtt    24300
tataaagtgg ttatagatga gaagaggaat aaaatgttat attttaggag gtgtattttg    24360 tttaataat tatgttgatt ttagggtgtt aagttaaaag gggtaaggga gaaagaaaat    24420
tgttaagtat gagttttaa tgtgaaattt aatttgttgg ttttttttagg tattagattt    24480 tggaagtgtt tgtaatgata gttaggaaag taaattaatg gttaatggtt tattgggttt    24540
gaatattaga gttttgttat tttttttatag attaagtata taatatatat atatatatat    24600
atatatatat atgaagttgt tttatgtgga attgttttgg aattaaaata tatgtttggg    24660
tgttattttg tattttggta gaaagggtag agggatttgt attttttttt tttgttttta    24720
ggttaagatt tatgaatgat ttttttaggtt tgtttgggat ggtggggaga ggtgtaggag    24780
atgtggtgag agaggatagt ttttatatta tttttttgta tatatttta ttttaggtgt    24840 aaatttgttg ttttttatagg aaggagaaag aggggtggtg gtgaagggaa atattatttt    24900
tttaagtagg gaagagatga taaaaattaa attgtgtttt ttgttttgt tttagttttg    24960 ttattggatt tggtttgtaa attttttaat tgttttgagt tgtttagaat tttgtaaata    25020
aagggagaaa atttttttaa gtgttattaa atgaaagttt gggttgttgt gtggtgtaga    25080
ataaaataag tatatatatg tttatttta aattttgttt tattatgtta aaaatttgag    25140
ttattttaag ttttattgtt tttttagatt tagtaggttt ggaaggagag aaaaatttgt    25200
tttatttagt taggttttttt tttttggaga agttataagt tttttatggt atttgttatt    25260
tgagttaatg aatgtgattg ttttgataag gtgttttttaa ttttattgat tttggtaaat    25320
tgtaggagat atttagttta tgttatataa aaattattaa agtgggattg ttgtagttga    25380
aaagtttgat tagtgtttgg agattagaat gtgagttttt aaagtatata tgtatttggt    25440
attgggaaag tttaggtgtt tgtgattttt tgaaggattt tgggttagta tttttgtgtt    25500 tggattatttt aggggggttat tagaaagtaa tatatgttat aagaaagatg tggggagat    25560
```

```
tttgatgttt gtgttttgt taggtggagg tggggtgtag gtagaagttg tgtgttggat    25620
tgttggatga attttgttat gtgtaggttt tgtgttgatt ttggaaggga taggtaggtt    25680
tggaagggat ttttggggtt tggggatgtt ttttagggta gagagtattg ttgtggtttg    25740
agtggtttgg gttttaggt gtggggtatt tggtttttaa gtgttttttg gggatgtagg    25800
tgtttatgta ttgtttagtt gtgtgttttt agtatttagt gtttggtgtt tttggtggag    25860
ttttgtgtat tttttttggaa agtttgggggg tttttttaat ttaggttttt ttgggagttt    25920
tggggtgggg gttggaagaa ggggttattt attttgttgt ttggtttgtt ttgggttttt    25980
gaagtgtttg ttttagttgt ggtttagtgt gtttgtaatt aagtatttat ttttgttttt    26040
tttagtgttg aagttttttt tttgtgttgt gttttggtg aaaataggat attttttttg    26100 gttatttat aataaatagt gtatataagt gggggagaag tggggtggag ggagaagttg    26160
gttttgaggg ggaggaggaa aggagaggag ttaaaatttt ggattgtgat agggggaaa    26220 ggagaagaaa agaaatgag agagtgtgtt tagttgttgt agttgttatt ttttggtttt    26280
ttttgtagtt ttttttttt ttttaaggta gtgataattt tatgtggata ggatggaagt    26340
tttgtgtgga agttgggaat ggttggagtg tgtgttgtgt tgttggtagt tttgtatttg    26400
tgtagggagg tggggtgggg gtgatgttgt tattggttat tgtgggtttg tgaggttgtt    26460
gggggttttg gggaggttg ttagggatgt gggggtggt ggtgtgtggg ggatttattt    26520 tgttttatt tgatttgg tgattgttta ttgttatggt ttgtgatttt gtgtgggat    26580 tgtttagggt tttggggttt tggatgtttt gggtggtgtt gttgtaattt ttgtgttttt    26640
tgtgttgttt ttatttgtt tttatttggg ttgatttgag tggttgtagt ttttaggttg    26700 aggggagggaa tttgtgattg tgttttttt tttgggttgg agagttattg ttgattttta    26760
tttgttttgg tggggtagtt tttggaattg tttggaattt ttttgttatt tagttttttt    26820
gtgtaggtta ttgtgggttt tttgttggat ttttttttat ttatttaag ggaggagata    26880 gaagggattt tgtttatttg taataatgtg aaataaaat taatttagat tagattgggg    26940
tgtttttttt gatgggagga atatttttt tttgtggaga tatatgttat gaaggattaa    27000
gtggtttggg gataggttgt gttgtgaagg gtttgggttt tttttagtgt tgtttgggtgt    27060 aggtataggt atttgttta gatgtttaaa ggttaggtag taatgattta ttttaaggt    27120 ggtgttagag ttttttagg tatattgttg aaatgatatt ttgtgtttaa gtttttgtg    27180 tatgtattat gtgattatat aggatttatg atttatatt tatatgtgtg tatgttataa    27240
ttaggggata tagtaaaggt agatggaata aataatttat aaattttgta tttatttaat    27300
tatttttttt aaaaatttat tgttttatttt agtggtattt ttttgttat attgataata    27360 aatgttttaa tttattgata aattattgag tgttaattat tgtattggtt attatggta    27420 tatgagttta tttaatttt atgataattt tatggtggtt attattaagt tggtataaaa    27480
gatgaggaaa ttaagtttta aagaattatg agtgatttt ttaaagataa atttagtggt    27540
ttttaattat aaagtttatg atataataat ttttatatta ttttaggtgt ggtttaagag    27600
attatagatt aatttgtaga aattatttt atttaaagaa agtttagttt taatatattt    27660
attaagttat gttttgaaaa aggtttagaa aaaagatttt atttttttatt ttaggttggt    27720 tttatgtaat tgatatgagt attgtttaat ttaaaagtag tattaatttt gaatatttat    27780
ggttataatt tattttttaa tgagtgggga attatttata atgtttaaga ggttttagaa    27840
aaggtggtgt tgtaaatta aaatgataaa ggtagttgtt gttgttttta ttatttattg    27900
ggtgtttttt tttgtagatt tattttggag ggtgtaggta ttgttaggta taatgttttt    27960
```

```
tttttttggtt tttaaggtag aaagggtttt ggtagtgggg ttggtataaa gtggatttgg     28020
agtatggttg agagtatatt ttggtttaat gaggaatgtt agttaatata tattggagag     28080
aaaaatatga atggatagat ttaattaatt ttgtagattt atttttttta ttttatatgt     28140
gagaaaatta agggtttaga attttagaa gtttgttaat aaatggtaga tttgagtttt      28200
aagttagttt ttatttaagt ttatttttag ttattgtgat gttattatta gtattaatgg     28260
tatttagaaa aatagtaatt tttttaaata tgtaatatat tataagttaa atatgtaatt     28320
taaatgtttt gtgaattata gtgtttaaga atgttttgtg gttatagtaa atattatgta     28380
aggattaagt ataatgatga atttaatatt gtttttaaaa ggtaataata ttttgaatt      28440 tattttggta taaaatatta tgtgttagtt ttatttataa ataaaggtgg gagatgtatg     28500
atttgaataa aataaaaatt tatattttag tatattgtta atataaatat agggtgggtt     28560
tttttagtat gttttttttgt atttttttaa agttagattt tttagttata ttgattttgt    28620
ttttaaggtt atttttgtttt tgtatagttt tttgtatatt tagataagaa tatatgtata   28680
gaaattattt ttaaaattta ggataatata ttagttattt gatttatat tattattttt     28740 taatagttgt tttaaatata tatatattaa tatggatatt attaggtgtt agataaaatg    28800
ttaattttta gtatatattt gaaataagtt taatatagga aatagaattt tagggttata    28860
aaggtaaaaa tgtattgttt gtttaaatga ggttttattt ttagtattta tattgaatat    28920
tatttttata attatagtta tattgtttat attattgatt taatatgtat ttttaaataa    28980 tttatttttaa ttaaataagt ttatttgata aaggatattt tttatagtta ttataaatgg   29040
aaaattaata aaatttgtta tgaatagaag atgattttgt aaaggaattt atattgtaga    29100
aataaaagtt ttttttatg tattatttaa aattatttta tatatagttt gagaaatatt     29160
ggtttaaaga attatatttt atatgttttt taggtttatt aagagatatt tttaagtttt    29220 tttttttat aattggaata aaatgttgtg tttaatttat tttgaggtat tattttttaa    29280 atttttgtgtt tatttaatta ttgttttttt tgttaaaaat atatttgaag ttttttgaagt  29340 tgaggtgttt ttttaaaatt tatgtattat ttattgtttt atttattatt ttatttgtgg    29400
taaaatgtaa ataatttata aatgtataat taaaaagtaa attattttt tgaaatattg     29460 tattggttat ttattatttt tttttagtat ttattagttt agtagtgtaa tatagtatag    29520
ataatgaaga agagagggaa agtagaatag tgggagaaat gtaaagggtt tagaaagata    29580
tatgggggaa attgaagtta gagatttgtt gttagatttt tgaagtgatt taaaaatatt    29640
agtgggtttt gtatgatatg agttaggttt ttagaatatt tgtatatgtt taatttagtt    29700
tgaaaaggga tgtgttttgg gaggagtggg gagataaaaa atataagatt ttatagggta    29760
aattagtgga aatataagat ttatttatta gtaatttttt taattaattt ttttggaatg   29820
ggatgttttt gtagttatta tttattattt gtttattttt taaatgtgta tggtattgtt    29880
ttggtattag attttgtata agttaaatta aataaagtgt tttaggagtt tataatttaa    29940
aatataattt ttgttttaat tttatttaaa agtaatttta agggaaaaat tag           29993
```

<210> SEQ ID NO 6
<211> LENGTH: 20
<212> TYPE: DNA
<213> ORGANISM: Artificial Sequence
<220> FEATURE:
<223> OTHER INFORMATION: PRIMER

<400> SEQUENCE: 6
cggagggtac ggagattacg     20

```
<210> SEQ ID NO 7
<211> LENGTH: 15
<212> TYPE: DNA
<213> ORGANISM: Artificial Sequence
<220> FEATURE:
<223> OTHER INFORMATION: PRIMER

<400> SEQUENCE: 7
cgacgacgcg cgaaa                                                         15

<210> SEQ ID NO 8
<211> LENGTH: 25
<212> TYPE: DNA
<213> ORGANISM: Artificial Sequence
<220> FEATURE:
<223> OTHER INFORMATION: PRIMER

<400> SEQUENCE: 8
tggtgatgga ggaggtttag taagt                                              25

<210> SEQ ID NO 9
<211> LENGTH: 25
<212> TYPE: DNA
<213> ORGANISM: Artificial Sequence
<220> FEATURE:
<223> OTHER INFORMATION: PRIMER

<400> SEQUENCE: 9
ggtgattgtt tattgttatg gtttg                                              25

<210> SEQ ID NO 10
<211> LENGTH: 23
<212> TYPE: DNA
<213> ORGANISM: Artificial Sequence
<220> FEATURE:
<223> OTHER INFORMATION: PRIMER

<400> SEQUENCE: 10 ccccctcaacc taaaaactac aac                                               23

<210> SEQ ID NO 11
<211> LENGTH: 29
<212> TYPE: DNA
<213> ORGANISM: Artificial Sequence
<220> FEATURE:
<223> OTHER INFORMATION: PROBE

<400> SEQUENCE: 11 cgaaaccctaaatatcccgaataacgccg                                            29

<210> SEQ ID NO 12
<211> LENGTH: 30
<212> TYPE: DNA
<213> ORGANISM: Artificial Sequence
<220> FEATURE:
<223> OTHER INFORMATION: PROBE

<400> SEQUENCE: 12
accaccaccc aacacacaat aacaaacaca                                         30

<210> SEQ ID NO 13
<211> LENGTH: 25
<212> TYPE: DNA
<213> ORGANISM: Artificial Sequence
<220> FEATURE:
<223> OTHER INFORMATION: PROBE
```

```
<400> SEQUENCE: 13
aaaattacga cgacgccacc cgaaa                                    25

<210> SEQ ID NO 14
<211> LENGTH: 25
<212> TYPE: DNA
<213> ORGANISM: Artificial Sequence
<220> FEATURE:
<223> OTHER INFORMATION: BLOCKER

<400> SEQUENCE: 14
gttatggttt gtgattttgt gtggg                                    25

<210> SEQ ID NO 15
<211> LENGTH: 26
<212> TYPE: DNA
<213> ORGANISM: Artificial Sequence
<220> FEATURE:
<223> OTHER INFORMATION: BLOCKER

<400> SEQUENCE: 15
aaactacaac cactcaaatc aaccca                                   26
```

METHOD AND NUCLEIC ACIDS FOR THE ANALYSIS OF COLORECTAL CELL PROLIFERATIVE DISORDERS

CROSS-REFERENCE TO RELATED APPLICATIONS

This application claims the benefit of priority to European Patent Application EP 02004551.4 filed Feb. 27, 2002, and to PCT/EP03/01457 filed Feb. 13, 2003 and entitled "Method and Nucleic Acids for the Analysis of Colorectal Cell Proliferative Disorders," which are incorporated by reference herein in their entireties.

FIELD OF THE INVENTION

Colorectal cancer is the fourth leading cause of cancer mortality in men and women. The 5-year survival rate is 61% over all stages with early detection being a prerequisite for curative therapy of the disease. Up to 95% of all colorectal cancers are adenocarcinomas of varying differentiation grades.

Sporadic colon cancer develops in a multistep process starting with the pathological transformation of normal colonic epithelium to an adenoma which consecutively progresses to invasive cancer. The progression rate of colonic adenomas is currently predicted based on their histological appearance, location, degree of spread and extent of bowel involvement. For example, tubular-type benign adenomas rarely progress to malignant tumours, whereas villous benign adenomas, particularly if larger than 2 cm in diameter, have a significant malignant potential.

During progression from benign proliferative lesions to malignant neoplasms several genetic and epigenetic alterations are known to occur. Somatic mutation of the APC gene seems to be one of the earliest events in 75 to 80% of colorectal adenomas and carcinomas. Activation of K-RAS is thought to be a critical step in the progression towards a malignant phenotype. Consecutively, mutations in other oncogenes as well as alterations leading to inactivation of tumour suppressor genes accumulate.

Aberrant DNA methylation within CpG islands is among the earliest and most common alterations in human cancers leading to abrogation or overexpression of a broad spectrum of genes. In addition, abnormal methylation has been shown to occur in CpG rich regulatory elements in intronic and coding parts of genes for certain tumours. In contrast to the specific hypermethylation of tumour suppressor genes, an overall hypomethylation of DNA can be observed in tumour cells. This decrease in global methylation can be detected early, far before the development of frank tumour formation. Also, correlation between hypomethylation and increased gene expression was reported for many oncogenes. In colon cancer, aberrant DNA methylation constitutes one of the most prominent alterations and inactivates many tumour suppressor genes such as p14ARF, p16lNK4a, THBS1, MINT2, and MINT31 and DNA mismatch repair genes such as hMLH1.

In the molecular evolution of colorectal cancer, DNA methylation errors have been suggested to play two distinct roles. In normal colonic mucosal cells, methylation errors accumulate as a function of age or as time-dependent events predisposing these cells to neoplastic transformation. For example, hypermethylation of several loci could be shown to be already present in adenomas, particularly in the tubulovillous and villous subtype. At later stages, increased DNA methylation of CpG islands plays an important role in a subset of tumours affected by the so called CpG island methylator phenotype (CIMP). Most CIMP+ tumours, which constitute about 15% of all sporadic colorectal cancers, are characterised by microsatellite instability (MIN) due to hypermethylation of the hMLH1 promoter and other DNA mismatch repair genes. By contrast, CIMP– colon cancers evolve along a more classic genetic instability pathway (CIN), with a high rate of p53 mutations and chromosomal changes.

However, the molecular subtypes do not only show varying frequencies regarding molecular alterations. According to the presence of either micro satellite instability or chromosomal aberrations, colon cancer can be subclassified into two classes, which also exhibit significant clinical differences. Almost all MIN tumours originate in the proximal colon (ascending and transversum), whereas 70% of CIN tumours are located in the distal colon and rectum. This has been attributed to the varying prevalence of different carcinogens in different sections of the colon. Methylating carcinogens, which constitute the prevailing carcinogen in the proximal colon have been suggested to play a role in the pathogenesis of MIN cancers, whereas CIN tumours are thought to be more frequently caused by adduct-forming carcinogens, which occur more frequently in distal parts of the colon and rectum. Moreover, MIN tumours have a better prognosis than do tumours with a CIN phenotype and respond better to adjuvant chemotherapy.

The identification of markers for the differentiation of colon carcinoma as well as for early detection are main goals of current research.

EYA4 is the most recently identified member of the vertebrate Eya (eyes-absent) gene family, a group of four transcriptional activators that interact with other proteins in a conserved regulatory hierarchy to ensure normal embryologic development. The EYA4 gene is mapped to 6q22.3 and encodes a 640 amino acid protein. The structure of EYA4 conforms to the basic pattern established by EYA1-3, and includes a highly conserved 271 amino acid C-terminus called the eya-homologous region (eyaHR; alternatively referred to as the eya domain or eya homology domain 1) and a more divergent proline-serine-threonine (PST)-rich (34-41%) transactivation domain at the N-terminus (Borsani G, et al., EYA4, a novel vertebrate gene related to Drosophila eyes absent. Hum Mol Genet 1999 January; 8(1):11-23). EYA proteins interact with members of the SIX and DACH protein families during early embryonic development. Mutations in the EYA4 gene are responsible for postlingual, progressive, autosomal dominant hearing loss at the DFNA10 locus (Wayne S, Robertson N G, DeClau F, Chen N, Verhoeven K, Prasad S, Tranebjarg L, Morton C C, Ryan A F, Van Camp G, Smith R J: Mutations in the transcriptional activator EYA4 cause late-onset deafness at the DFNA10 locus. Hum Mol Genet 2001 Feb. 1; 10(3):195-200 with further references). A link between the Methylation of Cytosine positions in the EYA 4 gene and cancer has not yet been established.

5-methylcytosine is the most frequent covalent base modification in the DNA of eukaryotic cells. It plays a role, for example, in the regulation of the transcription, in genetic imprinting, and in tumorigenesis. Therefore, the identification of 5-methylcytosine as a component of genetic information is of considerable interest. However, 5-methylcytosine positions cannot be identified by sequencing since 5-methylcytosine has the same base pairing behaviour as cytosine. Moreover, the epigenetic information carried by 5-methylcytosine is completely lost during PCR amplification.

A relatively new and currently the most frequently used method for analysing DNA for 5-methylcytosine is based upon the specific reaction of bisulfite with cytosine which, upon subsequent alkaline hydrolysis, is converted to uracil which corresponds to thymidine in its base pairing behaviour. However, 5-methylcytosine remains unmodified under these conditions. Consequently, the original DNA is converted in such a manner that methylcytosine, which originally could not be distinguished from cytosine by its hybridisation behaviour, can now be detected as the only remaining cytosine using "normal" molecular biological techniques, for example, by amplification and hybridisation or sequencing. All of these techniques are based on base pairing which can now be fully exploited. In terms of sensitivity, the prior art is defined by a method which encloses the DNA to be analysed in an agarose matrix, thus preventing the diffusion and renaturation of the DNA (bisulfite only reacts with single-stranded DNA), and which replaces all precipitation and purification steps with fast dialysis (Olek A, Oswald J, Walter J. A modified and improved method for bisulphite based cytosine methylation analysis. Nucleic Acids Res. 1996 Dec. 15; 24(24):5064-6). Using this method, it is possible to analyse individual cells, which illustrates the potential of the method. However, currently only individual regions of a length of up to approximately 3000 base pairs are analysed, a global analysis of cells for thousands of possible methylation events is not possible. However, this method cannot reliably analyse very small fragments from small sample quantities either. These are lost through the matrix in spite of the diffusion protection.

An overview of the further known methods of detecting 5-methylcytosine may be gathered from the following review article: Rein, T., DePamphilis, M. L., Zorbas, H., Nucleic Acids Res. 1998, 26, 2255.

To date, barring few exceptions (e.g., Zeschnigk M, Lich C, Buiting K, Doerfler W, Horsthemke B. A single-tube PCR test for the diagnosis of Angelman and Prader-Willi syndrome based on allelic methylation differences at the SNRPN locus. Eur J Hum Genet. 1997 March-April; 5(2):94-8) the bisulfite technique is only used in research. Always, however, short, specific fragments of a known gene are amplified subsequent to a bisulfite treatment and either completely sequenced (Olek A, Walter J. The pre-implantation ontogeny of the H19 methylation imprint. Nat Genet. 1997 November; 17(3):275-6) or individual cytosine positions are detected by a primer extension reaction (Gonzalgo M L, Jones P A. Rapid quantitation of methylation differences at specific sites using methylation-sensitive single nucleotide primer extension (Ms-SNuPE). Nucleic Acids Res. 1997 Jun. 15; 25(12):2529-31, WO 95/00669) or by enzymatic digestion (Xiong Z, Laird P W. COBRA: a sensitive and quantitative DNA methylation assay. Nucleic Acids Res. 1997 Jun. 15; 25(12):2532-4). In addition, detection by hybridisation has also been described (Olek et al., WO 99/28498).

Further publications dealing with the use of the bisulfite technique for methylation detection in individual genes are: Grigg G, Clark S. Sequencing 5-methylcytosine residues in genomic DNA. Bioessays. 1994 June; 16(6):431-6, 431; Zeschnigk M, Schmitz B, Dittrich B, Buiting K, Horsthemke B, Doerfler W. Imprinted segments in the human genome: different DNA methylation patterns in the Prader-Willi/Angelman syndrome region as determined by the genomic sequencing method. Hum Mol Genet. 1997 March; 6(3):387-95; Feil R, Charlton J, Bird A P, Walter J, Reik W. Methylation analysis on individual chromosomes: improved protocol for bisulphite genomic sequencing. Nucleic Acids Res. 1994 Feb. 25; 22(4):695-6; Martin V, Ribieras S, Song-Wang X, Rio M C, Dante R. Genomic sequencing indicates a correlation between DNA hypomethylation in the 5' region of the pS2 gene and its expression in human breast cancer cell lines. Gene. 1995 May 19; 157(1-2):261-4; WO 97/46705 and WO 95/15373.

An overview of the Prior Art in oligomer array manufacturing can be gathered from a special edition of Nature Genetics (Nature Genetics Supplement, Volume 21, January 1999), published in January 1999, and from the literature cited therein.

Fluorescently labelled probes are often used for the scanning of immobilised DNA arrays. The simple attachment of Cy3 and Cy5 dyes to the 5'-OH of the specific probe are particularly suitable for fluorescence labels. The detection of the fluorescence of the hybridised probes may be carried out, for example via a confocal microscope. Cy3 and Cy5 dyes, besides many others, are commercially available.

Matrix Assisted Laser Desorption Ionization Mass Spectrometry (MALDI-TOF) is a very efficient development for the analysis of biomolecules (Karas M, Hillenkamp F. Laser desorption ionization of proteins with molecular masses exceeding 10,000 daltons. Anal Chem. 1988 Oct. 15; 60(20): 2299-301). An analyte is embedded in a light-absorbing matrix. The matrix is evaporated by a short laser pulse thus transporting the analyte molecule into the vapour phase in an unfragmented manner. The analyte is ionised by collisions with matrix molecules. An applied voltage accelerates the ions into a field-free flight tube. Due to their different masses, the ions are accelerated at different rates. Smaller ions reach the detector sooner than bigger ones.

MALDI-TOF spectrometry is excellently suited to the analysis of peptides and proteins. The analysis of nucleic acids is somewhat more difficult (Gut I G, Beck S. DNA and Matrix Assisted Laser Desorption Ionization Mass Spectrometry. Current Innovations and Future Trends. 1995, 1; 147-57). The sensitivity to nucleic acids is approximately 100 times worse than to peptides and decreases disproportionally with increasing fragment size. For nucleic acids having a multiply negatively charged backbone, the ionisation process via the matrix is considerably less efficient. In MALDI-TOF spectrometry, the selection of the matrix plays an eminently important role. For the desorption of peptides, several very efficient matrixes have been found which produce a very fine crystallisation. There are now several responsive matrixes for DNA, however, the difference in sensitivity has not been reduced. The difference in sensitivity can be reduced by chemically modifying the DNA in such a manner that it becomes more similar to a peptide. Phosphorothioate nucleic acids in which the usual phosphates of the backbone are substituted with thiophosphates can be converted into a charge-neutral DNA using simple alkylation chemistry (Gut I G, Beck S. A procedure for selective DNA alkylation and detection by mass spectrometry. Nucleic Acids Res. 1995 Apr. 25; 23(8):1367-73). The coupling of a charge tag to this modified DNA results in an increase in sensitivity to the same level as that found for peptides. A further advantage of charge tagging is the increased stability of the analysis against impurities which make the detection of unmodified substrates considerably more difficult.

Genomic DNA is obtained from DNA of cell, tissue or other test samples using standard methods. This standard methodology is found in references such as Sambrook, Fritsch and Maniatis eds., Molecular Cloning: A Laboratory Manual, 1989.

DESCRIPTION

The present invention discloses novel methods for the detection of cell proliferative disorders. Said invention discloses the use of the gene EYA4, as well as its promoter and regulatory elements as a marker for colon cell proliferative disorders. More specifically, the disclosed matter shows the applicability of said gene to the detection of colon cell proliferative disorders, distinguishing between different classes of colon cell proliferative disorders as well as the differentiation of colon cell proliferative disorders from cell proliferative disorders originating from other tissues.

In one aspect of the invention, the disclosed matters provides novel nucleic acid sequences useful for the analysis of methylation within said gene, other aspects provide novel uses of the gene and the gene product as well as methods, assays and kits directed to detecting, differentiating and distinguishing colon cell proliferative disorders, as well as therapeutic and diagnostic methods thereof.

In one embodiment the method discloses the use of the gene EYA4 as a marker for the differentiation, detection and distinguishing of colon cell proliferative disorders. Said use of the gene may be enabled by means of any analysis of the expression of the gene, by means of mRNA expression analysis or protein expression analysis. However, in the most preferred embodiment of the invention, the detection, differentiation and distinguishing of colon cell proliferative disorders is enabled by means of analysis of the methylation status of the gene EYA4 and its promoter or regulatory elements.

To detect the presence of mRNA encoding EYA4 in a detection system for colon cancer, a sample is obtained from a patient. The sample can be a tissue biopsy sample or a sample of blood, plasma, serum or the like. The sample may be treated to extract the nucleic acids contained therein. The resulting nucleic acid from the sample is subjected to gel electrophoresis or other separation techniques. Detection involves contacting the nucleic acids and in particular the mRNA of the sample with a DNA sequence serving as a probe to form hybrid duplexes. The stringency of hybridisation is determined by a number of factors during hybridisation and during the washing procedure, including temperature, ionic strength, length of time and concentration of formamide. These factors are outlined in, for example, Sambrook et al. (Molecular Cloning: A Laboratory Manual, 2d ed., 1989). Detection of the resulting duplex is usually accomplished by the use of labelled probes. Alternatively, the probe may be unlabeled, but may be detectable by specific binding with a ligand which is labelled, either directly or indirectly. Suitable labels and methods for labelling probes and ligands are known in the art, and include, for example, radioactive labels which may be incorporated by known methods (e.g., nick translation or kinasing), biotin, fluorescent groups, chemiluminescent groups (e.g., dioxetanes, particularly triggered dioxetanes), enzymes, antibodies, and the like.

In order to increase the sensitivity of the detection in a sample of mRNA encoding EYA4, the technique of reverse transcription/polymerisation chain reaction can be used to amplify cDNA transcribed from mRNA encoding EYA4. The method of reverse transcription/PCR is well known in the art (for example, see Watson and Fleming, supra).

The reverse transcription/PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and EYA4 specific primers. (Belyavsky et al, Nucl Acid Res 17:2919-2932, 1989; Krug and Berger, Methods in Enzymology, Academic Press, N.Y., Vol. 152, pp. 316-325, 1987 which are incorporated by reference)

The present invention may also be described in certain embodiments as a kit for use in detecting a colon cancer disease state through testing of a biological sample. A representative kit may comprise one or more nucleic acid segments as described above that selectively hybridise to EYA4 mRNA and a container for each of the one or more nucleic acid segments. In certain embodiments the nucleic acid segments may be combined in a single tube. In further embodiments, the nucleic acid segments may also include a pair of primers for amplifying the target mRNA. Such kits may also include any buffers, solutions, solvents, enzymes, nucleotides, or other components for hybridisation, amplification or detection reactions. Preferred kit components include reagents for reverse transcription-PCR, in situ hybridisation, Northern analysis and/or RPA The present invention further provides for methods to detect the presence of the polypeptide, EYA4, in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (for example see Basic and Clinical Immunology, Sites and Terr, eds., Appleton & Lange, Norwalk, Conn. pp 217-262, 1991 which is incorporated by reference). Preferred are binder-ligand immunoassay methods including reacting antibodies with an epitope or epitopes of EYA4 and competitively displacing a labelled EYA4 protein or derivative thereof.

Certain embodiments of the present invention comprise the use of antibodies specific to the polypeptide encoded by the EYA4 gene. Such antibodies may be useful for diagnostic and prognostic applications in detecting the disease state, by comparing a patient's levels of colon disease marker expression to expression of the same markers in normal individuals. In certain embodiments production of monoclonal or polyclonal antibodies can be induced by the use of the EYA4 polypeptide as antigene. Such antibodies may in turn be used to detect expressed proteins as markers for human disease states. The levels of such proteins present in the peripheral blood or prostate tissue sample of a patient may be quantified by conventional methods. Antibody-protein binding may be detected and quantified by a variety of means known in the art, such as labelling with fluorescent or radioactive ligands. The invention further comprises kits for performing the above-mentioned procedures, wherein such kits contain antibodies specific for the EYA4 polypeptides.

Numerous competitive and non-competitive protein binding immunoassays are well known in the art. Antibodies employed in such assays may be unlabeled, for example as used in agglutination tests, or labelled for use a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like. Polyclonal or monoclonal antibodies to EYA4 or an epitope thereof can be made for use in immunoassays by any of a number of methods known in the art. One approach for preparing antibodies to a protein is the selection and preparation of an amino acid sequence of all or part of the protein, chemically synthesising the sequence and injecting it into an appropriate animal, usually a rabbit or a mouse (Milstein and Kohler Nature 256:495-497, 1975; Gulfre and Milstein, Methods in Enzymology: Immunochemical Techniques 73:1-46, Langone and Banatis eds., Academic Press, 1981 which are incorporated by reference). Methods for preparation of EYA4 or an epitope thereof include, but are not limited to chemical synthesis, recombinant DNA techniques or isolation from biological samples.

The invention provides significant improvements over the state of the art in that there are currently no markers used to detect colon cancer from body fluid samples. Current methods used to detect and diagnose colon cell proliferative disorders include colonoscopy, sigmoidoscopy, and fecal occult blood colon cancer. In comparison to these methods, the disclosed invention is much less invasive than colonoscopy, and as, if not more sensitive than sigmoidoscopy and FOBT. Compared to the previous descriptions of these markers in the literature, the described invention provides significant advantages in terms of sensitivity and specificity due to the advantageous combination of using highly sensitive assay techniques.

The objective of the invention can be achieved by analysis of the methylation state of the CpG dinucleotides within the genomic sequence according to SEQ ID NO: 1 and sequences complementary thereto. SEQ ID NO: 1 discloses the gene EYA4 and its promoter and regulatory elements, wherein said fragment comprises CpG dinucleotides exhibiting a disease specific methylation pattern. The methylation pattern of the gene EYA4 and its promoter and regulatory elements have heretofore not been analysed with regard to cell proliferative disorders. Due to the degeneracy of the genetic code, the sequence as identified in SEQ ID NO: 1 should be interpreted so as to include all substantially similar and equivalent sequences upstream of the promoter region of a gene which encodes a polypeptide with the biological activity of that encoded by EYA4.

In a preferred embodiment of the method, the objective of the invention is achieved by analysis of a nucleic acid comprising a sequence of at least 18 bases in length according to one of SEQ ID NO: 2 to SEQ ID NO: 5 and sequences complementary thereto.

The sequences of SEQ ID NOS: 2 to 5 provide modified versions of the nucleic acid according to SEQ ID NO: 1, wherein the conversion of said sequence results in the synthesis of a nucleic acid having a sequence that is unique and distinct from SEQ ID NO: 1 as follows. (see also the following TABLE 1): SEQ ID NO: 1, sense DNA strand of EYA4 gene and its promoter and regulatory elements; SEQ ID NO: 2, converted SEQ ID NO: 1, wherein "C" or "T," but "cp." remains "cp." (i.e., corresponds to case where, for SEQ ID NO: 1, all "C" residues of cp. dinucleotide sequences are methylated and are thus not converted); SEQ ID NO: 3, complement of SEQ ID NO: 1, wherein "C" to "T," but "cp." remains "cp." (i.e., corresponds to case where, for the complement (antisense strand) of SEQ ID NO: 1, all "C" residues of cp. dinucleotide sequences are methylated and are thus not converted); SEQ ID NO: 4, converted SEQ ID NO: 1, wherein "C" to "T" for all "C" residues, including those of "cp." dinucleotide sequences (i.e., corresponds to case where, for SEQ ID NO: 1, all "C" residues of cp. dinucleotide sequences are unmethylated); SEQ ID NO: 5, complement of SEQ ID NO: 1, wherein "C" to "T" for all "C" residues, including those of "CpG" dinucleotide sequences (i.e., corresponds to case where, for the complement (antisense strand) of SEQ ID NO: 1, all "C" residues of CpG dinucleotide sequences are unmethylated).

TABLE 1

Description of SEQ ID NOS: 1 to 5

| SEQ ID NO | Relationship to SEQ ID NO: 1 | Nature of cytosine base conversion |
|---|---|---|
| SEQ ID NO: 1 | Sense strand (EYA4 gene including promoter and regulatory elements) | None; untreated sequence |
| SEQ ID NO: 2 | Converted sense strand | "C" to "T," but "CpG" remains "CpG" (all "C" residues of CpGs are methylated) |
| SEQ ID NO: 3 | Converted antisense strand | "C." to "T," but "CpG" remains "CpG" (all "C" residues of CpGs are methylated) |
| SEQ ID NO: 4 | Converted sense strand | "C." to "T" for all "C" residues (all "C" residues of CpGs are unmethylated) |
| SEQ ID NO: 5 | Converted antisense strand | "C" to "T" for all "C" residues (all "C" residues of CpGs are unmethylated) |

Significantly, heretofore, the nucleic acid sequences and molecules according to SEQ ID NO: 1 to SEQ ID NO: 5 were not implicated in or connected with the ascertainment of colon cell proliferative disorders.

The described invention further disclose an oligonucleotide or oligomer for detecting the cytosine methylation state within pretreated DNA, according to SEQ ID NO: 2 to SEQ ID NO: 5. Said oligonucleotide or oligomer comprising a nucleic acid sequence having a length of at least nine (9) nucleotides which hybridises, under moderately stringent or stringent conditions (as defined herein above), to a pretreated nucleic acid sequence according to SEQ ID NO: 2 to SEQ ID NO: 5 and/or sequences complementary thereto.

Thus, the present invention includes nucleic acid molecules (e.g., oligonucleotides and peptide nucleic acid (PNA) molecules (PNA-oligomers)) that hybridise under moderately stringent and/or stringent hybridisation conditions to all or a portion of the sequences of SEQ ID NOS: 2 to 5, or to the complements thereof. The hybridising portion of the hybridising nucleic acids is typically at least 9, 15, 20, 25, 30 or 35 nucleotides in length. However, longer molecules have inventive utility, and are thus within the scope of the present invention.

Preferably, the hybridising portion of the inventive hybridising nucleic acids is at least 95%, or at least 98%, or 100% identical to the sequence, or to a portion thereof of SEQ ID NOS: 2 to 5, or to the complements thereof.

Hybridising nucleic acids of the type described herein can be used, for example, as a primer (e.g., a PCR primer), or a diagnostic and/or prognostic probe or primer. Preferably, hybridisation of the oligonucleotide probe to a nucleic acid sample is performed under stringent conditions and the probe is 100% identical to the target sequence. Nucleic acid duplex or hybrid stability is expressed as the melting temperature or Tm, which is the temperature at which a probe dissociates from a target DNA. This melting temperature is used to define the required stringency conditions.

For target sequences that are related and substantially identical to the corresponding sequence of SEQ ID NO: 1 (such as EYA41 allelic variants and SNPs), rather than identical, it is useful to first establish the lowest temperature at which only homologous hybridisation occurs with a particular concentration of salt (e.g., SSC or SSPE). Then, assuming that 1% mismatching results in a 1° C. decrease in the Tm, the temperature of the final wash in the hybridisation reaction is reduced accordingly (for example, if sequences having >95% identity with the probe are sought, the final wash temperature is decreased by 5° C.). In practice, the change in Tm can be between 0.5° C. and 1.5° C. per 1% mismatch.

Examples of inventive oligonucleotides of length X (in nucleotides), as indicated by polynucleotide positions with reference to, e.g., SEQ ID NO: 1, include those corresponding to sets of consecutively overlapping oligonucleotides of length X, where the oligonucleotides within each consecutively overlapping set (corresponding to a given X value) are defined as the finite set of Z oligonucleotides from nucleotide positions:

n to (n+(X−1));
where n=1, 2, 3, . . . (Y−(X−1));
where Y equals the length (nucleotides or base pairs) of SEQ ID NO: 1;
where X equals the common length (in nucleotides) of each oligonucleotide in the set (e.g., X=20 for a set of consecutively overlapping 20-mers); and
where the number (Z) of consecutively overlapping oligomers of length X for a given SEQ ID NO of length Y is equal to Y−(X−1). For example Z=2,785−19=2,766 for either sense or antisense sets of SEQ ID NO: 1, where X=20.

Preferably, the set is limited to those oligomers that comprise at least one CpG, TpG or CpA dinucleotide.

The present invention encompasses, for each of SEQ ID NOS: 2 to 5 (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to ascertain genetic and epigenetic parameters of the genomic sequence corresponding to SEQ ID NO: 1. Preferred sets of such oligonucleotides or modified oligonucleotides of length X are those consecutively overlapping sets of oligomers corresponding to SEQ ID NOS: 1-5 (and to the complements thereof). Preferably, said oligomers comprise at least one CpG, TpG or CpA dinucleotide. Included in these preferred sets are the preferred oligomers corresponding to SEQ ID NO: 11 to SEQ ID NO: 15.

Particularly preferred oligonucleotides or oligomers according to the present invention are those in which the cytosine of the CpG dinucleotide (or of the corresponding converted TpG or CpA dinculeotide) sequences is within the middle third of the oligonucleotide; that is, where the oligonucleotide is, for example, 13 bases in length, the CpG, TpG or CpA dinucleotide is positioned within the fifth to ninth nucleotide from the 5'-end.

The oligonucleotides of the invention can also be modified by chemically linking the oligonucleotide to one or more moieties or conjugates to enhance the activity, stability or detection of the oligonucleotide. Such moieties or conjugates include chromophores, fluorophors, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514, 758, 5,565,552, 5,567,810, 5,574,142, 5,585,481, 5,587,371, 5,597,696 and 5,958,773. The probes may also exist in the form of a PNA (peptide nucleic acid) which has particularly preferred pairing properties. Thus, the oligonucleotide may include other appended groups such as peptides, and may include hybridisation-triggered cleavage agents (Krol et al., BioTechniques 6:958-976, 1988) or intercalating agents (Zon, Pharm. Res. 5:539-549, 1988). To this end, the oligonucleotide may be conjugated to another molecule, e.g., a chromophore, fluorophor, peptide, hybridisation-triggered cross-linking agent, transport agent, hybridisation-triggered cleavage agent, etc.

The oligonucleotide may also comprise at least one art-recognized modified sugar and/or base moiety, or may comprise a modified backbone or non-natural internucleoside linkage.

The oligomers according to the present invention are normally used in so called "sets" which contain at least one oligomer for analysis of each of the CpG dinucleotides of a genomic sequence comprising SEQ ID NO: 1 and sequences complementary thereto or to their corresponding CG, TG or CA dinucleotide within the pretreated nucleic acids according to SEQ ID NO: 2 to SEQ ID NO: 5 and sequences complementary thereto. Preferred is a set which contains at least one oligomer for each of the CpG dinucleotides within the gene EYA4 and it's promoter and regulatory elements in both the pretreated and genomic versions of said gene, SEQ ID NO: 2 to 5 and SEQ ID NO: 1, respectively. However, it is anticipated that for economic or other factors it may be preferable to analyse a limited selection of the CpG dinucleotides within said sequences and the contents of the set of oligonucleotides should be altered accordingly. Therefore, the present invention moreover relates to a set of at least 3 n (oligonucleotides and/or PNA-oligomers) used for detecting the cytosine methylation state in pretreated genomic DNA (SEQ ID NO: 2 to SEQ ID NO: 5 and sequences complementary thereto) and genomic DNA (SEQ ID NO: 1 and sequences complementary thereto). These probes enable diagnosis and/or therapy of genetic and epigenetic parameters of cell proliferative disorders. The set of oligomers may also be used for detecting single nucleotide polymorphisms (SNPs) in pretreated genomic DNA (SEQ ID NO: 2 to SEQ ID NO: 5, and sequences complementary thereto) and genomic DNA (SEQ ID NO: 1, and sequences complementary thereto).

Moreover, the present invention makes available a set of at least two oligonucleotides which can be used as so-called "primer oligonucleotides" for amplifying DNA sequences of one of SEQ ID NO: 1 to SEQ ID NO: 5 and sequences complementary thereto, or segments thereof.

In the case of the sets of oligonucleotides according to the present invention, it is preferred that at least one and more preferably all members of the set of oligonucleotides is bound to a solid phase.

According to the present invention, it is preferred that an arrangement of different oligonucleotides and/or PNA-oligomers (a so-called "array") made available by the present invention is present in a manner that it is likewise bound to a solid phase. This array of different oligonucleotide- and/or PNA-oligomer sequences can be characterised in that it is arranged on the solid phase in the form of a rectangular or hexagonal lattice. The solid phase surface is preferably composed of silicon, glass, polystyrene, aluminium, steel, iron, copper, nickel, silver, or gold. However, nitrocellulose as well as plastics such as nylon which can exist in the form of pellets or also as resin matrices may also be used.

Therefore, a further subject matter of the present invention is a method for manufacturing an array fixed to a carrier material for analysis in connection with cell proliferative disorders, in which method at least one oligomer according to the present invention is coupled to a solid phase. Methods for manufacturing such arrays are known, for example, from U.S. Pat. No. 5,744,305 by means of solid-phase chemistry and photolabile protecting groups.

A further subject matter of the present invention relates to a DNA chip for the analysis of cell proliferative disorders. DNA chips are known, for example, in U.S. Pat. No. 5,837,832.

The described invention further provides a composition of matter useful for detecting, differentiation and distinguishing between colon cell proliferative disorders. Said composition comprising at least one nucleic acid 18 base pairs in length of a segment of the nucleic acid sequence disclosed in SEQ ID NO: 2 to 5, and one or more substances taken from the group comprising:

1-5 mM Magnesium Chloride, 100-500 µM dNTP, 0.5-5 units of taq polymerase, bovine serum albumen, an oligomer in particular an oligonucleotide or peptide nucleic acid (PNA)-oligomer, said oligomer comprising in each case at least one base sequence having a length of at least 9 nucleotides which is complementary to, or hybridises under moderately stringent or stringent conditions to a pretreated genomic DNA according to one of the SEQ ID NO: 2 to SEQ ID NO: 5 and sequences complementary thereto. It is preferred that said composition of matter comprises a buffer solution appropriate for the stabilisation of said nucleic acid in an aqueous solution and enabling polymerase based reactions within said solution. Suitable buffers are known in the art and commercially available.

The present invention further provides a method for conducting an assay in order to ascertain genetic and/or epigenetic parameters of the gene EYA4 and its promoter and regulatory elements. Most preferably the assay according to the following method is used in order to detect methylation within the gene EYA4 wherein said methylated nucleic acids are present in a solution further comprising an excess of background DNA, wherein the background DNA is present in between 100 to 1000 times the concentration of the DNA to be detected. Said method comprising contacting a nucleic acid sample obtained from said subject with at least one reagent or a series of reagents, wherein said reagent or series of reagents, distinguishes between methylated and non-methylated CpG dinucleotides within the target nucleic acid.

Preferably, said method comprises the following steps: In the first step, a sample of the tissue to be analysed is obtained. The source may be any suitable source, preferably, the source of the sample is selected from the group consisting of histological slides, biopsies, paraffin-embedded tissue, bodily fluids, plasma, serum, stool, urine, blood, and combinations thereof. Preferably, the source is biopsies, bodily fluids, urine, or blood.

The DNA is then isolated from the sample. Extraction may be by means that are standard to one skilled in the art, including the use of detergent lysates, sonification and vortexing with glass beads. Once the nucleic acids have been extracted, the genomic double stranded DNA is used in the analysis.

In the second step of the method, the genomic DNA sample is treated in such a manner that cytosine bases which are unmethylated at the 5'-position are converted to uracil, thymine, or another base which is dissimilar to cytosine in terms of hybridisation behaviour. This will be understood as 'pretreatment' herein.

The above described treatment of genomic DNA is preferably carried out with bisulfite (hydrogen sulfite, disulfite) and subsequent alkaline hydrolysis which results in a conversion of non-methylated cytosine nucleobases to uracil or to another base which is dissimilar to cytosine in terms of base pairing behaviour. Enclosing the DNA to be analysed in an agarose matrix, thereby preventing the diffusion and renaturation of the DNA (bisulfite only reacts with single-stranded DNA), and replacing all precipitation and purification steps with fast dialysis (Olek A, et al., A modified and improved method for bisulfite based cytosine methylation analysis, *Nucleic Acids Res*. 24:5064-6, 1996). It is further preferred that the bisulfite treatment is carried out in the presence of a radical trap or DNA denaturing agent.

In the third step of the method, fragments of the pretreated DNA are amplified. Wherein the source of the DNA is free DNA from serum, or DNA extracted from paraffin it is particularly preferred that the size of the amplificate fragment is between 100 and 200 base pairs in length, and wherein said DNA source is extracted from cellular sources (e.g. tissues, biopsies, cell lines) it is preferred that the amplificate is between 100 and 350 base pairs in length. It is particularly preferred that said amplificates comprise at least one 20 base pair sequence comprising at least three CpG dinucleotides. Said amplification is carried out using sets of primer oligonucleotides according to the present invention, and a preferably heat-stable polymerase. The amplification of several DNA segments can be carried out simultaneously in one and the same reaction vessel, in one embodiment of the method preferably six or more fragments are amplified simultaneously. Typically, the amplification is carried out using a polymerase chain reaction (PCR). The set of primer oligonucleotides includes at least two oligonucleotides whose sequences are each reverse complementary, identical, or hybridise under stringent or highly stringent conditions to an at least 18-base-pair long segment of the base sequences of SEQ ID NO: 2 to SEQ ID NO: 5 and sequences complementary thereto.

In an alternate embodiment of the method, the methylation status of preselected CpG positions within the nucleic acid sequences comprising SEQ ID NO: 2 to SEQ ID NO: 5 may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridises to a bisulfite treated CpG dinucleotide. Therefore, the sequence of said primers comprises at least one CpG, TpG or CpA dinucleotide. MSP primers specific for non-methylated DNA contain a "T" at the 3' position of the C position in the CpG. Preferably, therefore, the base sequence of said primers is required to comprise a sequence having a length of at least 18 nucleotides which hybridises to a pretreated nucleic acid sequence according to SEQ ID NO: 2 to SEQ ID NO: 5 and sequences complementary thereto, wherein the base sequence of said oligomers comprises at least one CpG, TpG or CpA dinucleotide. In this embodiment of the method according to the invention it is particularly preferred that the MSP primers comprise between 2 and 4 CpG, TpG or CpA dinucleotides. It is further preferred that said dinucleotides are located within the 3' half of the primer e.g. wherein a primer is 18 bases in length the specified dinucleotides are located within the first 9 bases form the 3'end of the molecule. In addition to the CpG, TpG or CpA dinucleotides it is further preferred that said primers should further comprise several bisulfite converted bases (i.e. cytosine converted to thymine, or on the hybridising strand, guanine converted to adenosine). In a further preferred embodiment said primers are designed so as to comprise no more than 2 cytosine or guanine bases.

In one embodiment of the method the primers may be selected form the group consisting to SEQ ID NO: 6 to SEQ ID NO: 10.

The fragments obtained by means of the amplification can carry a directly or indirectly detectable label. Preferred are labels in the form of fluorescence labels, radionuclides, or detachable molecule fragments having a typical mass which can be detected in a mass spectrometer. Where said labels are mass labels, it is preferred that the labelled amplificates have a single positive or negative net charge, allowing for better detectability in the mass spectrometer. The detection may be carried out and visualised by means of, e.g., matrix assisted laser desorption/ionisation mass spectrometry (MALDI) or using electron spray mass spectrometry (ESI).

Matrix Assisted Laser Desorption/Ionization Mass Spectrometry (MALDI-TOF) is a very efficient development for the analysis of biomolecules (Karas & Hillenkamp, *Anal Chem.*, 60:2299-301, 1988). An analyte is embedded in a light-absorbing matrix. The matrix is evaporated by a short laser pulse thus transporting the analyte molecule into the vapour phase in an unfragmented manner. The analyte is ionised by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut & Beck, *Current Innovations and Future Trends*, 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionisation process via the matrix is considerably less efficient. In MALDI-TOF spectrometry, the selection of the matrix plays an eminently important role. For the desorption of peptides, several very efficient matrixes have been found which produce a very fine crystallisation. There are now several responsive matrixes for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut & Beck, *Nucleic Acids Res.* 23: 1367-73, 1995). The coupling of a charge tag to this modified DNA results in an increase in MALDI-TOF sensitivity to the same level as that found for peptides. A further advantage of charge tagging is the increased stability of the analysis against impurities, which makes the detection of unmodified substrates considerably more difficult.

In a particularly preferred embodiment of the method the amplification of step three is carried out in the presence of at least one species of blocker oligonucleotides. The use of such blocker oligonucleotides has been described by Yu et al., *BioTechniques* 23:714-720, 1997. The use of blocking oligonucleotides enables the improved specificity of the amplification of a subpopulation of nucleic acids. Blocking probes hybridised to a nucleic acid suppress, or hinder the polymerase mediated amplification of said nucleic acid. In one embodiment of the method blocking oligonucleotides are designed so as to hybridise to background DNA. In a further embodiment of the method said oligonucleotides are designed so as to hinder or suppress the amplification of unmethylated nucleic acids as opposed to methylated nucleic acids or vice versa.

Blocking probe oligonucleotides are hybridised to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridise to the bisulfite treated nucleic acid in a methylation status specific manner. For example, for detection of methylated nucleic acids within a population of unmethylated nucleic acids, suppression of the amplification of nucleic acids which are unmethylated at the position in question would be carried out by the use of blocking probes comprising a 'TpG' at the position in question, as opposed to a 'CpG.' In one embodiment of the method the sequence of said blocking oligonucleotides should be identical or complementary to molecule is complementary or identical to a sequence at least 18 base pairs in length selected from the group consisting of SEQ ID NOS: 2 to 5, preferably comprising one or more CpG, TpG or CpA dinucleotides. In one embodiment of the method the sequence of said oligonucleotides is selected from the group consisting SEQ ID NO: 15 and SEQ ID NO: 16 and sequences complementary thereto.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivitised at the 3' position with other than a "free" hydroxyl group. For example, 3'-O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-termini thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker—a process that normally results in degradation of the hybridised blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

In one embodiment of the method, the binding site of the blocking oligonucleotide is identical to, or overlaps with that of the primer and thereby hinders the hybridisation of the primer to its binding site. In a further preferred embodiment of the method, two or more such blocking oligonucleotides are used. In a particularly preferred embodiment, the hybridisation of one of the blocking oligonucleotides hinders the hybridisation of a forward primer, and the hybridisation of another of the probe (blocker) oligonucleotides hinders the hybridisation of a reverse primer that binds to the amplificate product of said forward primer.

In an alternative embodiment of the method, the blocking oligonucleotide hybridises to a location between the reverse and forward primer positions of the treated background DNA, thereby hindering the elongation of the primer oligonucleotides.

It is particularly preferred that the blocking oligonucleotides are present in at least 5 times the concentration of the primers.

In the fourth step of the method, the amplificates obtained during the third step of the method are analysed in order to ascertain the methylation status of the CpG dinucleotides prior to the treatment.

In embodiments where the amplificates were obtained by means of MSP amplification and/or blocking oligonucleotides, the presence or absence of an amplificate is in itself indicative of the methylation state of the CpG positions covered by the primers and or blocking oligonucleotide, according to the base sequences thereof. All possible known molecular biological methods may be used for this detection, including, but not limited to gel electrophoresis, sequencing, liquid chromatography, hybridisations, real time PCR analysis or combinations thereof. This step of the method further acts as a qualitative control of the preceding steps.

In the fourth step of the method amplificates obtained by means of both standard and methylation specific PCR are further analysed in order to determine the CpG methylation status of the genomic DNA isolated in the first step of the method. This may be carried out by means of based-based methods such as, but not limited to, array technology and probe based technologies as well as by means of techniques such as sequencing and template directed extension.

In one embodiment of the method, the amplificates synthesised in step three are subsequently hybridised to an array or a set of oligonucleotides and/or PNA probes. In this context, the hybridisation takes place in the following manner: the set of probes used during the hybridisation is preferably composed of at least 2 oligonucleotides or PNA-oligomers; in the process, the amplificates serve as probes which hybridise to oligonucleotides previously bonded to a solid phase; the non-hybridised fragments are subsequently removed; said oligonucleotides contain at least one base sequence having a length of at least 9 nucleotides which is reverse complementary or identical to a segment of the base sequences specified in the SEQ ID NO: 2 to SEQ ID NO: 5; and the segment comprises at least one CpG, TpG or CpA dinucleotide.

In a preferred embodiment, said dinucleotide is present in the central third of the oligomer. For example, wherein the oligomer comprises one CpG dinucleotide, said dinucleotide is preferably the fifth to ninth nucleotide from the 5'-end of a 13-mer. One oligonucleotide exists for the analysis of each CpG dinucleotide within the sequence according to SEQ ID NO: 1, and the equivalent positions within SEQ ID NOS: 2 to 5. Said oligonucleotides may also be present in the form of peptide nucleic acids. The non-hybridised amplificates are then removed. The hybridised amplificates are detected. In this context, it is preferred that labels attached to the amplificates are identifiable at each position of the solid phase at which an oligonucleotide sequence is located.

In yet a further embodiment of the method, the genomic methylation status of the CpG positions may be ascertained by means of oligonucleotide probes that are hybridised to the bisulfite treated DNA concurrently with the PCR amplification primers (wherein said primers may either be methylation specific or standard).

A particularly preferred embodiment of this method is the use of fluorescence-based Real Time Quantitative PCR (Heid et al., *Genome Res.* 6:986-994, 1996; also see U.S. Pat. No. 6,331,393). There are two preferred embodiments of utilising this method. One embodiment, known as the TaqMan™ assay employs a dual-labelled fluorescent oligonucleotide probe. The TaqMan™ PCR reaction employs the use of a non-extendible interrogating oligonucleotide, called a TaqMan™ probe, which is designed to hybridise to a GpC-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide. Hybridised probes are displaced and broken down by the polymerase of the amplification reaction thereby leading to an increase in fluorescence. For analysis of methylation within nucleic acids subsequent to bisulfite treatment, it is required that the probe be methylation specific, as described in U.S. Pat. No. 6,331, 393, (hereby incorporated by reference in its entirety) also known as the MethylLight assay. The second preferred embodiment of this technology is the use of dual-probe technology (Lightcycler®), each carrying donor or recipient fluorescent moieties, hybridisation of two probes in proximity to each other is indicated by an increase or fluorescent amplification primers. Both these techniques may be adapted in a manner suitable for use with bisulfite treated DNA, and moreover for methylation analysis within CpG dinucleotides.

In a further preferred embodiment of the method, the fourth step of the method comprises the use of template-directed oligonucleotide extension, such as MS-SNuPE as described by Gonzalgo & Jones, *Nucleic Acids Res.* 25:2529-2531, 1997. In said embodiment it is preferred that the Ms-SNuPE primer is identical or complementary to a sequence at least nine but preferably no more than twenty five nucleotides in length of one or more of the sequences taken from the group of SEQ ID NO: 2 to SEQ ID NO: 5.

In yet a further embodiment of the method, the fourth step of the method comprises sequencing and subsequent sequence analysis of the amplificate generated in the third step of the method (Sanger F., et al., *Proc Natl Acad Sci USA* 74:5463-5467, 1977).

Additional embodiments of the invention provide a method for the analysis of the methylation status of genomic DNA according to the invention (SEQ ID NO: 1) without the need for pretreatment.

In the first step of such additional embodiments, the genomic DNA sample is isolated from tissue or cellular sources. Preferably, such sources include cell lines, histological slides, body fluids, or tissue embedded in paraffin. Extraction may be by means that are standard to one skilled in the art, including but not limited to the use of detergent lysates, sonification and vortexing with glass beads. Once the nucleic acids have been extracted, the genomic double-stranded DNA is used in the analysis.

In a preferred embodiment, the DNA may be cleaved prior to the treatment, and this may be by any means standard in the state of the art, in particular with methylation-sensitive restriction endonucleases.

In the second step, the DNA is then digested with one or more methylation sensitive restriction enzymes. The digestion is carried out such that hydrolysis of the DNA at the restriction site is informative of the methylation status of a specific CpG dinucleotide.

In the third step, which is optional but a preferred embodiment, the restriction fragments are amplified. This is preferably carried out using a polymerase chain reaction, and said amplificates may carry suitable detectable labels as discussed above, namely fluorophore labels, radionuclides and mass labels.

In the final step the amplificates are detected. The detection may be by any means standard in the art, for example, but not limited to, gel electrophoresis analysis, hybridisation analysis, incorporation of detectable tags within the PCR products, DNA array analysis, MALDI or ESI analysis.

The present invention enables diagnosis and/or prognosis of events which are disadvantageous to patients or individuals in which important genetic and/or epigenetic parameters within the EYA4 gene and its promoter or regulatory elements may be used as markers. Said parameters obtained by means of the present invention may be compared to another set of genetic and/or epigenetic parameters, the differences serving as the basis for a diagnosis and/or prognosis of events which are disadvantageous to patients or individuals.

Specifically, the present invention provides for diagnostic and/or prognostic cancer assays based on measurement of differential methylation of EYA4 CpG dinucleotide sequences. Preferred gene sequences useful to measure such differential methylation are represented herein by SEQ ID NOS: 1 to 5. Typically, such assays involve obtaining a tissue sample from a test tissue, performing an assay to measure the methylation status of at least one of the inventive EYA4-specific CpG dinucleotide sequences derived from the tissue sample, relative to a control sample, and making a diagnosis or prognosis based thereon.

In particular preferred embodiments, inventive oligomers are used to assess EYA4 specific CpG dinucleotide methylation status, such as those based on SEQ ID NOS: 1 to 5, including the representative preferred oligomers corresponding to SEQ ID NOS: 11 to 15, or arrays thereof, as well as a kit based thereon are useful for the diagnosis and/or prognosis of cancer and/or other prostate cell proliferative disorders.

The present invention moreover relates to a diagnostic agent and/or therapeutic agent for the diagnosis and/or therapy colon cell proliferative disorders, the diagnostic agent and/or therapeutic agent being characterised in that at least one primer or probe based on SEQ ID NOS: 1 to 5 is used for manufacturing it, possibly together with suitable additives and ancillary agents. In one embodiment, the EYA4 polypeptide or a fragment or derivative thereof may be administered to a subject to treat or prevent colon cancers.

In another embodiment, a vector capable of expressing EYA4, or a fragment or a derivative thereof, may also be administered to a subject to treat or prevent colon cancers.

In another embodiment, agonists which are specific for EYA4 may be used to stimulate or prolong the activity of EYA4 and may be administered to a subject to treat or prevent colon cancers.

In other embodiments, any of the therapeutic proteins or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of colon cancer. Using this approach, one may be able to achieve therapeutic efficacy with lower dosages of each agent, thus reducing the potential for adverse side effects.

Expression vectors derived from retroviruses, adenovirus, herpes or vaccinia viruses, or from various bacterial plasmids may be used for delivery of nucleotide sequences to the targeted organ, tissue or cell population.

An additional embodiment of the invention relates to the administration of a pharmaceutical composition, in conjunction with a pharmaceutically acceptable carrier. Such pharmaceutical compositions may consist of EYA4 or agonists of EYA4. The compositions may be administered alone or in combination with at least one other agent, such as stabilising compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilised in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Moreover, an additional aspect of the present invention is a kit comprising, for example: a bisulfite-containing reagent as well as at least one oligonucleotide whose sequences in each case correspond, are complementary, or hybridise under stringent or highly stringent conditions to a 18-base long segment of the sequences SEQ ID NOS: 1 to 5. Said kit may further comprise instructions for carrying out and evaluating the described method. In a further preferred embodiment, said kit may further comprise standard reagents for performing a CpG position-specific methylation analysis, wherein said analysis comprises one or more of the following techniques: MS-SNuPE, MSP, MethyLight™, HeavyMethyl™, COBRA, and nucleic acid sequencing. However, a kit along the lines of the present invention can also contain only part of the aforementioned components.

Typical reagents (e.g., as might be found in a typical COBRA-based kit) for COBRA analysis may include, but are not limited to: PCR primers for specific gene (or methylation-altered DNA sequence or CpG island); restriction enzyme and appropriate buffer; gene-hybridisation oligo; control hybridisation oligo; kinase labelling kit for oligo probe; and radioactive nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Typical reagents (e.g., as might be found in a typical MethyLight®-based kit) for MethyLight® analysis may include, but are not limited to: PCR primers for specific gene (or methylation-altered DNA sequence or CpG island); Taq-Man® probes; optimised PCR buffers and deoxynucleotides; and Taq polymerase.

Typical reagents (e.g., as might be found in a typical Ms-SNuPE-based kit) for Ms-SNuPE analysis may include, but are not limited to: PCR primers for specific gene (or methylation-altered DNA sequence or CpG island); optimised PCR buffers and deoxynucleotides; gel extraction kit; positive control primers; Ms-SNuPE primers for specific gene; reaction buffer (for the Ms-SNuPE reaction); and radioactive nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

Typical reagents (e.g., as might be found in a typical MSP-based kit) for MSP analysis may include, but are not limited to: methylated and unmethylated PCR primers for specific gene (or methylation-altered DNA sequence or CpG island), optimised PCR buffers and deoxynucleotides, and specific probes.

DEFINITIONS

In the context of the present invention, the term "CpG island" refers to a contiguous region of genomic DNA that satisfies the criteria of (1) having a frequency of CpG dinucleotides corresponding to an "Observed/Expected Ratio">0.6, and (2) having a "GC Content">0.5. CpG islands are typically, but not always, between about 0.2 to about 1 kb in length.

In the context of the present invention, the term "methylation state" or "methylation status" refers to the presence or absence of 5-methylcytosine ("5-mCyt") at one or a plurality of CpG dinucleotides within a DNA sequence. Methylation states at one or more particular palindromic CpG methylation sites (each having two CpG CpG dinucleotide sequences) within a DNA sequence include "unmethylated," "fully-methylated" and "hemi-methylated."

In the context of the present invention, the term "hemimethylation" or "hemimethylation" refers to the methylation state of a palindromic CpG methylation site, where only a single cytosine in one of the two CpG dinucleotide sequences of the palindromic CpG methylation site is methylated (e.g., 5'-CC$^M$GG-3' (top strand): 3'-GGCC-5' (bottom strand)).

In the context of the present invention, the term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

In the context of the present invention, the term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

In the context of the present invention, the term "microarray" refers broadly to both "DNA microarrays," and 'DNA chip(s),' as recognised in the art, encompasses all art-recognised solid supports, and encompasses all methods for affixing nucleic acid molecules thereto or synthesis of nucleic acids thereon.

"Genetic parameters" are mutations and polymorphisms of genes and sequences further required for their regulation. To be designated as mutations are, in particular, insertions, deletions, point mutations, inversions and polymorphisms and, particularly preferred, SNPs (single nucleotide polymorphisms).

"Epigenetic parameters" are, in particular, cytosine methylations. Further epigenetic parameters include, for example, the acetylation of histones which, however, cannot be directly analysed using the described method but which, in turn, correlate with the DNA methylation.

In the context of the present invention, the term "bisulfite reagent" refers to a reagent comprising bisulfite, disulfite, hydrogen sulfite or combinations thereof, useful as disclosed herein to distinguish between methylated and unmethylated CpG dinucleotide sequences.

In the context of the present invention, the term "Methylation assay" refers to any assay for determining the methylation state of one or more CpG dinucleotide sequences within a sequence of DNA.

In the context of the present invention, the term "MS.AP-PCR" (Methylation-Sensitive Arbitrarily-Primed Polymerase Chain Reaction) refers to the art-recognised technology that allows for a global scan of the genome using CG-rich primers to focus on the regions most likely to contain CpG dinucleotides, and described by Gonzalgo et al., *Cancer Research* 57:594-599, 1997.

In the context of the present invention, the term "MethyLight" refers to the art-recognised fluorescence-based real-time PCR technique described by Eads et al., *Cancer Res.* 59:2302-2306, 1999.

In the context of the present invention, the term "HeavyMethyl™" assay, in the embodiment thereof implemented herein, refers to a HeavyMethyl™ MethylLight assay, which is a variation of the MethylLight assay, wherein the MethylLight assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones, *Nucleic Acids Res.* 25:2529-2531, 1997.

The term "MSP" (Methylation-specific PCR) refers to the art-recognised methylation assay described by Herman et al. *Proc. Natl. Acad. Sci. USA* 93:9821-9826, 1996, and by U.S. Pat. No. 5,786,146.

The term "COBRA" (Combined Bisulfite Restriction Analysis) refers to the art-recognized methylation assay described by Xiong & Laird, *Nucleic Acids Res.* 25:2532-2534, 1997.

The term "hybridisation" is to be understood as a bond of an oligonucleotide to a complementary sequence along the lines of the Watson-Crick base pairings in the sample DNA, forming a duplex structure.

"Stringent hybridisation conditions," as defined herein, involve hybridising at 68° C. in 5×SSC/5×Denhardt's solution/1.0% SDS, and washing in 0.2×SSC/0.1% SDS at room temperature, or involve the art-recognised equivalent thereof (e.g., conditions in which a hybridisation is carried out at 60° C. in 2.5×SSC buffer, followed by several washing steps at 37° C. in a low buffer concentration, and remains stable). Moderately stringent conditions, as defined herein, involve including washing in 3×SSC at 42° C., or the art-recognised equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

"Background DNA" as used herein refers to any nucleic acids which originate from sources other than colon cells.

The invention will now be described in more detail based on the following examples, SEQ IDs, and Figures, without being limited thereto. In the sequence protocol and the Figures, SEQ ID NO: 1 shows the sequence of the human gene EYA4, SEQ ID NOS: 2 to 5 show chemically pretreated sequences of the gene EYA4, SEQ ID NOS: 6 to 10 show the sequences of primers used in the examples, and SEQ ID NOS: 11 to 15 show sequences of probes used in the examples.

FIG. 1 shows the level of methylation determined by a MSP MethyLight assay and by a HeavyMethyl MethyLight assay according to examples 1 and 2. The Y-axis shows the degree of methylation within the region of the EYA4 gene investigated. Tumour samples are represented by white points, and normal colon tissue samples by white black points. A significantly higher degree of methylation was observed in tumour samples than in healthy tissue samples. The level of significance as measured using a t-test was p=0.00000312 (MSP-ML, Example 1) and p=0.000000326 (HM-ML, Example 2).

FIG. 2 shows the Receiver Operating Characteristic curve (ROC curve) of the MSP-Methyl-Light-Assay for Adenocarcinomas according to Example 1. A ROC is a plot of the true positive rate against the false positive rate for the different possible cutpoints of a diagnostic test. It shows the tradeoff between sensitivity and specificity depending on the selected cutpoint (any increase in sensitivity will be accompanied by a decrease in specificity). The area under an ROC curve (AUC) is a measure for the accuracy of a diagnostic test (the larger the area the better, optimum is 1, a random test would have a ROC curve lying on the diagonal with an area of 0.5) The AUC for the MSP-Methyl-Light-Assay is: 0.94.

FIG. 3 shows the Receiver Operating Characteristic curve (ROC curve) of the HM-Methyl-Light-Assay for Adenocarcinoma according to Example 2. The area under an ROC curve (AUC) is a measure for the accuracy of a diagnostic test. The AUC for the HM-Methyl-Light-Assay is: 0.91.

FIG. 4 shows the level of methylation determined by a HeavyMethyl MethyLight assay according to example 2, testing an additional set of colon samples (25 adenocarcinoma, 33 normals, and 13 adenomas). The Y-axis shows the degree of methylation within the region of the EYA4 gene investigated. Adenocarcinoma samples are represented by white squares, and normal colon tissue samples by black diamonds. A significantly higher degree of methylation was observed in tumour samples than in healthy tissue samples. The level of significance as measured using a t-test was 0.00424.

FIG. 5 shows the Receiver Operating Characteristic curve (ROC curve) of the HM-Methyl-Light-Assay for Adenocarcinoma and Adenoma according to Example 2 (additional sets of samples). The area under an ROC curve (AUC) is a measure for the accuracy of a diagnostic test. The AUC for the HM-Methyl-Light-Assay is 0.81.

FIG. 6 shows the Receiver Operating Characteristic curve (ROC curve) of the HM-Methyl-Light-Assay for Adenocarcinoma only according to Example 2 (additional sets of samples). The area under an ROC curve (AUC) is a measure for the accuracy of a diagnostic test. The AUC for the HM-Methyl-Light-Assay is: 0.844.

FIG. 7 shows the Receiver Operating Characteristic curve (ROC curve) of the HM-Methyl-Light-Assay for Adenenomas according to Example 2 (additional sets of samples). The area under an ROC curve (AUC) is a measure for the accuracy of a diagnostic test. The AUC for the HM-Methyl-Light-Assay is: 0.748.

FIG. 8 shows the level of methylation in different tumour and healthy tissues determined by a HeavyMethyl MethyLight assay according to example 3. The Y-axis shows the degree of methylation within the region of the EYA4 gene investigated. Besides the colon cancer samples only one of the two breast cancer tissues were methylated.

Example 1

Analysis of Methylation within Colon Cancer Using an MSP—MethyLight Assay

DNA was extracted from 33 colon adenocarcinoma samples and 43 colon normal adjacent tissues using a Qiagen® extraction kit. The DNA from each sample was treated using a bisulfite solution (hydrogen sulfite, disulfite) according to the agarose-bead method (Olek et al 1996). The treatment is such that all non methylated cytosines within the sample are converted to thymidine. Conversely, 5-methylated cytosines within the sample remain unmodified.

The methylation status was determined with a MSP-MethyLight assay designed for the CpG island of interest and a control fragment from the beta actin gene (Eads et al., 2001). The CpG island assay covers CpG sites in both the primers and the taqman style probe, while the control gene does not. The control gene is used as a measure of total DNA concentration, and the CpG island assay (methylation assay) determines the methylation levels at that site.

Methods: The EYA4 gene CpG island assay was performed using the following primers and probes:

```
Forward Primer:
CGGAGGGTACGGAGATTACG;            (SEQ ID NO: 6)

Reverse Primer:
CGACGACGCGCGAAA;                 (SEQ ID NO: 7)

and

Probe:
CGAAACCCTAAATATCCCGAATAACGCCG.   (SEQ ID NO: 12)
```

The corresponding control assay was performed using the following primers and probes:

```
Primer:
TGGTGATGGAGGAGGTTTAGTAAGT;       (SEQ ID NO: 8)

Primer:
AACCAATAAAACCTACTCCTCCCTTAA;     (SEQ ID NO: 9)

and

Probe:
ACCACCACCCAACACACAATAACAAACACA   (SEQ ID NO: 13)
```

The reactions were run in triplicate on each DNA sample with the following assay conditions: Reaction solution: (900 nM primers; 300 nM probe; 3.5 mM Magnesium Chloride; 1 unit of taq polymerase; 200 µM dNTPs; 7 µl of DNA, in a final reaction volume of 20 µl);

Cycling conditions: (95° C. for 10 minutes; then 50 cycles of: 95° C. for 15 seconds; 60° C. for 1 minute). The data was analysed using a PMR calculation previously described in the literature (Eads et al 2001).

Figure 1:
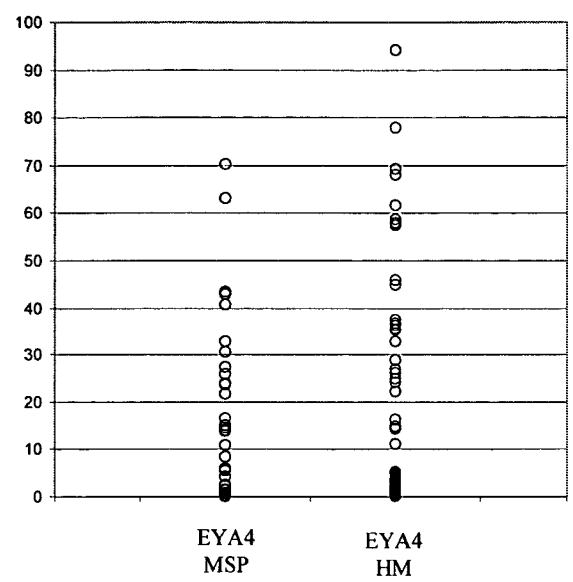

Results. The mean PMR for normal samples was 0.15, with a standard deviation of 0.18. The mean PMR for tumour samples was 17.98, with a standard deviation of 18.18. The overall difference in methylation levels between tumour and normal samples is significant in a t-test (p=0.00000312). The results are shown in FIG. 1.

Figure 2:
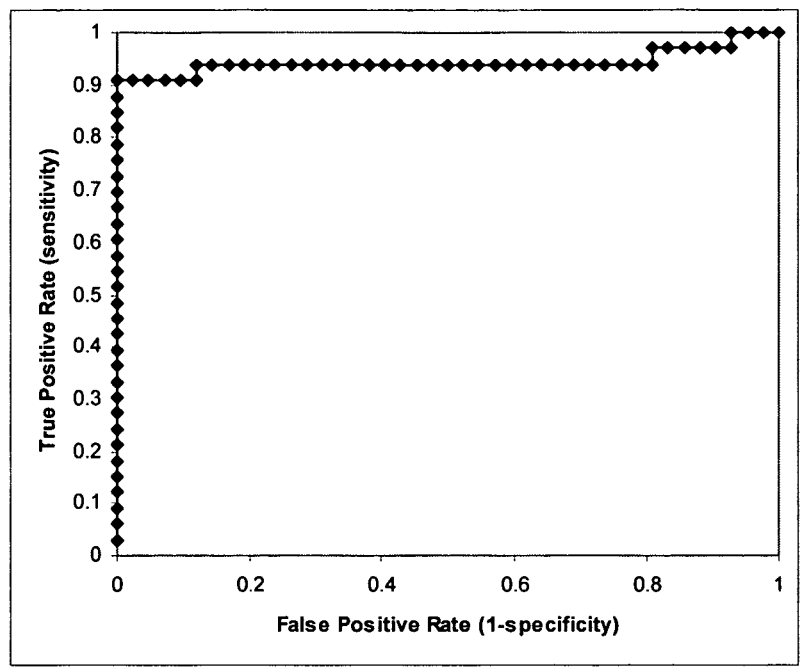

A Receiver Operating Characteristic curve (ROC curve) of the assay was also determined. A ROC is a plot of the true positive rate against the false positive rate for the different possible cutpoints of a diagnostic test. It shows the tradeoff between sensitivity and specificity depending on the selected cutpoint (any increase in sensitivity will be accompanied by a decrease in specificity). The area under an ROC curve (AUC) is a measure for the accuracy of a diagnostic test (the larger the area the better, optimum is 1, a random test would have a ROC curve lying on the diagonal with an area of 0.5; for reference: J. P. Egan. Signal Detection Theory and ROC Analysis, Academic Press, New York, 1975). The AUC for the MSP-Methyl-Light-Assay is: 0.94 (FIG. 2).

Example 2

Methylation within Colon Cancer was Analyzed using a HeavyMethyl MethyLight☐ Assay.

The same DNA samples were also used to analyse methylation of the CpG island with a HeavyMethyl MethyLight (or HM MethyLight) assay, also referred to as the HeavyMethyl assay. The methylation status was determined with a HM MethyLight assay designed for the CpG island of interest and the same control gene assay described above. The CpG island assay covers CpG sites in both the blockers and the taqman style probe, while the control gene does not.

Methods. The CpG island assay (methylation assay) was performed using the following primers and probes:

```
Forward    GGTGATTGTTTATTGTTATGGTTTG    (SEQ ID NO: 10)
Primer:

Reverse    CCCCTCAACCTAAAAACTACAAC       (SEQ ID NO: 11)
Primer:

Forward    GTTATGGTTTGTGATTTTGTGTGGG     (SEQ ID NO: 15)
Blocker:

Reverse    AAACTACAACCACTCAAATCAACCCA    (SEQ ID NO: 16)
Blocker:

Probe:     AAAATTACGACGACGCCACCCGAAA     (SEQ ID NO: 14)
```

The reactions were each run in triplicate on each DNA sample with the following assay conditions:

Reaction solution: (400 nM primers; 400 nM probe; 10 µM both blockers; 3.5 mM magnesium chloride; 1×ABI Taqman buffer; 1 unit of ABI TaqGold polymerase; 200 µM dNTPs; and 7 µl of DNA, in a final reaction volume of 20 µl);

Cycling conditions: (95° C. for 10 minutes); (95° C. for 15 seconds, 64° C. for 1 minute (2 cycles)); (95° C. for 15 seconds, 62° C. for 1 minute (2 cycles); (95° C. for 15 seconds, 60° C. for 1 minute (2 cycles)); and (95° C. for 15 seconds, 58° C. for 1 minute, 60° C. for 40 seconds (41 cycles)).

Figure 3:
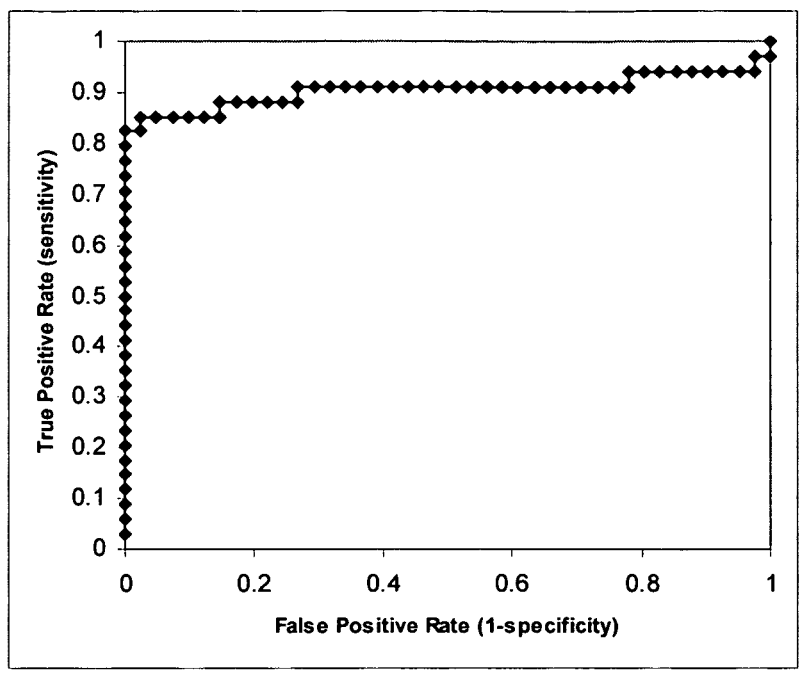

Results. The mean PMR for normal samples was 1.12 with a standard deviation of 1.45. The mean PMR for tumour samples was 38.23 with a standard deviation of 33.22. The overall difference in methylation levels between tumour and normal samples is significant in a t-test (p=0.000000326). The results are shown in FIG. 1. A ROC curve of the assay was also determined. The AUC for the MSP-Methyl-Light-Assay is 0.91 (FIG. 3)

Figure 4:
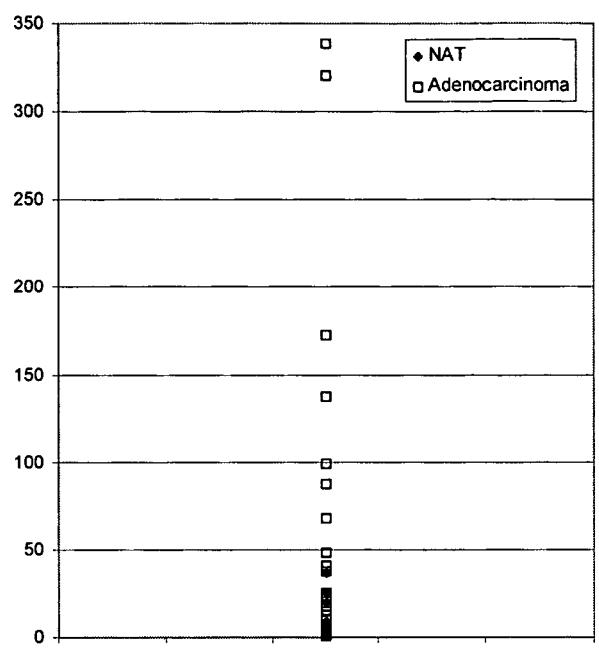
Figure 5:
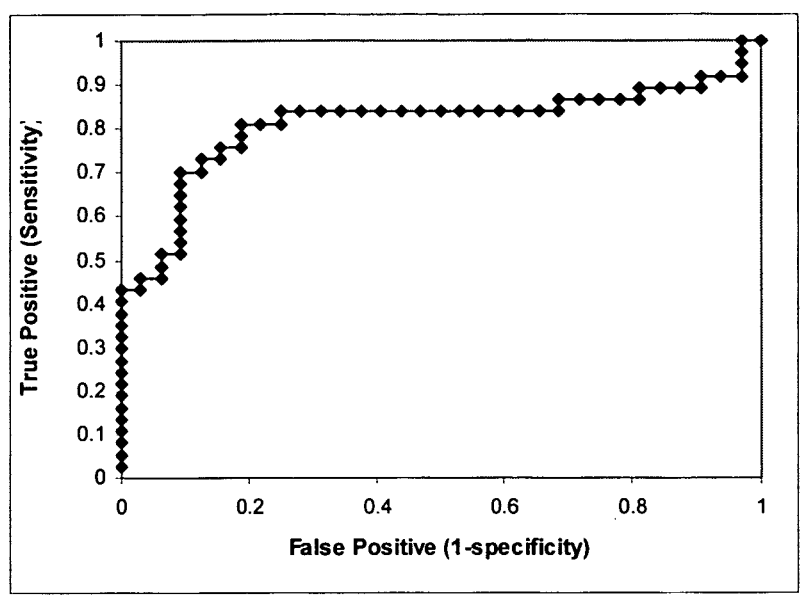
Figure 6:
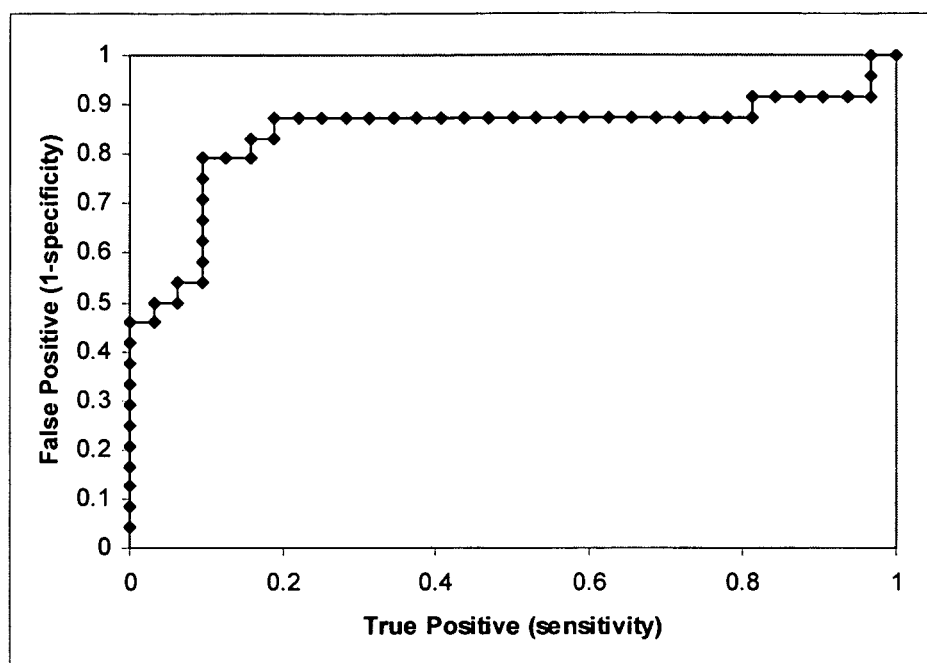
Figure 7:
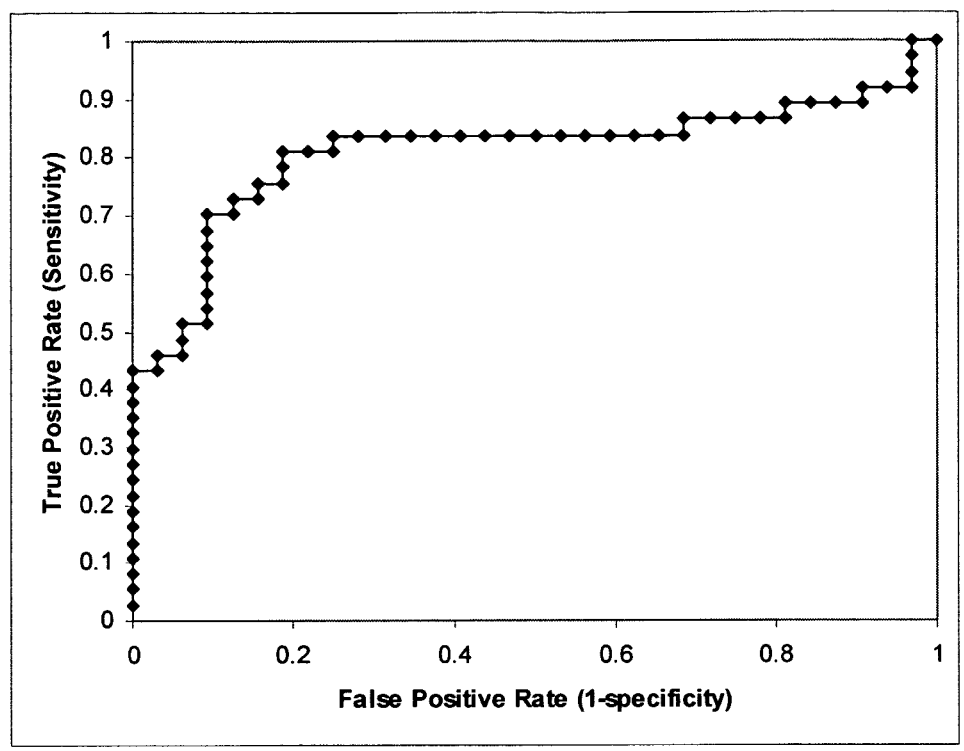

The assay was tested on an additional set of colon samples (25 adenocarcinoma, 33 normals, and 13 adenomas). The results showed a significant difference again (FIG. 4). The ROC are shown in FIG. 5-7.

Example 3

Figure 8:
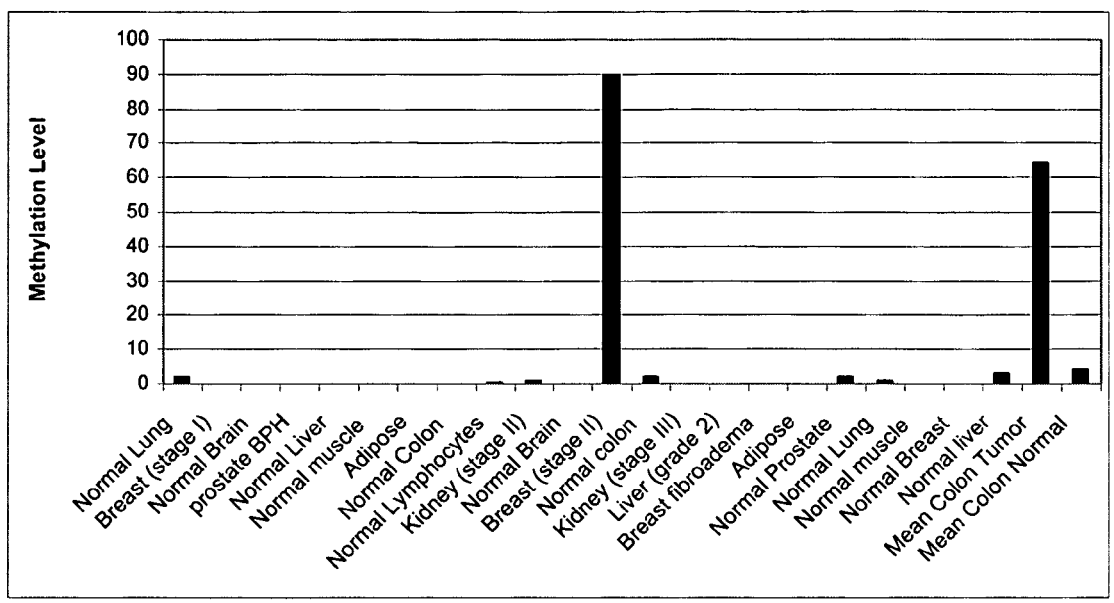
Figure 9:
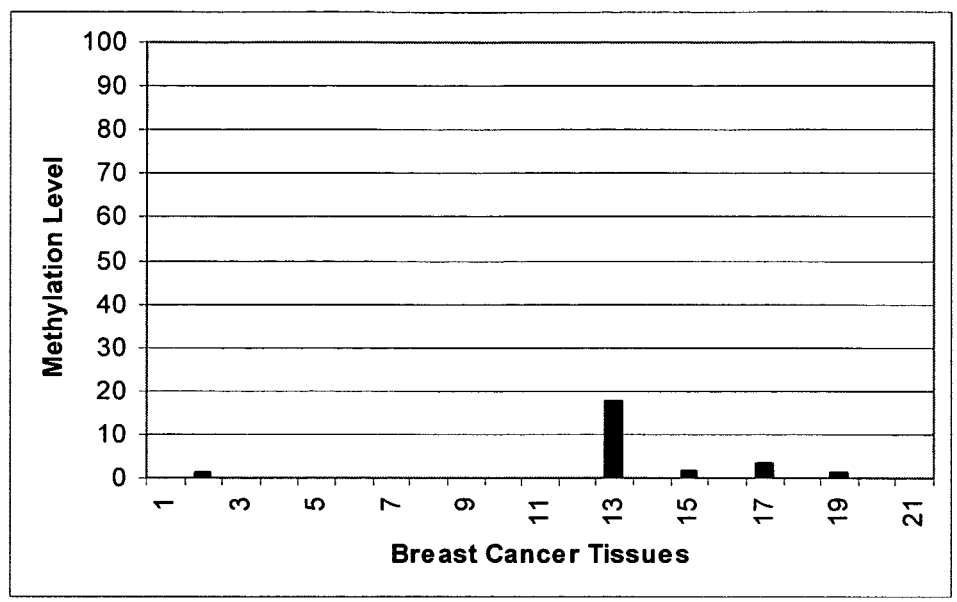
FIG. 9 shows the level of methylation in different breast cancer tissues determined by a HeavyMethyl MethyLight assay according to example 3. Only one tissue was methylated.

The HeavyMethyl-MethyLight-assay was also tested against a panel of other tissues (FIG. 8). Besides the colon cancer samples only one of the two breast cancer tissues were methylated. However, on a panel of 21 additional breast tumours (different stages), only one was methylated (FIG. 9). So the marker is specific for colon tumour samples. All primers, probes, blockers and reaction conditions were identical to those used in the analysis of the colon cancer samples (Example 2).

Example 4

Figure 10:
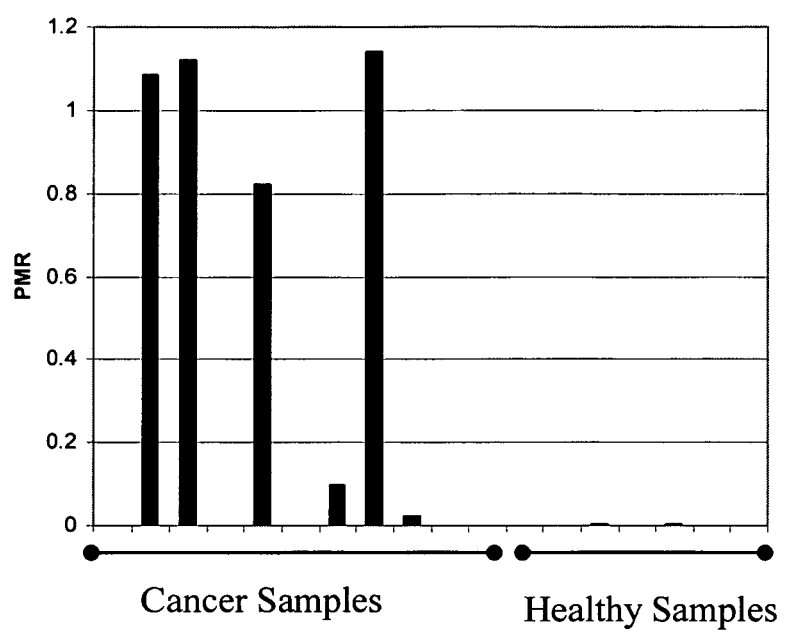
FIG. 10 shows the level of methylation in serum samples determined by a HeavyMethyl MethyLight assay according to example 4. The Y-axis shows the degree of methylation within the region of the EYA4 gene investigated.

Twelve of the colon tissues analysed by real-time PCR also had paired serum taken before surgery. We extracted DNA from 1 ml of that serum using a Qiagen UltraSens® DNA extraction kit, bisulfite treated the DNA sample, and ran the HeavyMethyl-MethyLight-assay on those samples. The control gene did not amplify for three of the cancer serum samples and three of the normal serum samples, so we can conclude that the sample preparation did not work in these cases. In the other cases, there was evidence of higher methylation in the cancer samples than the normal samples (FIG. 10).

The invention claimed is:

1. A method of diagnosing a colon cell proliferative disorder in a subject, comprising:
   (a) obtaining one or more biological samples comprising DNA from a subject suspected of having a colon cell proliferative disorder;
   (b) treating the DNA with bisulfite;
   wherein the presence of unconverted cytosines in the bisulfite treated nucleic acid sequence comprising SEQ ID NO: 1 as compared to converted cytosines in the bisulfite treated nucleic acid sequence indicates the presence of a colon cell proliferative disorder.

2. The method of claim 1, wherein:
   one or more fragments of the treated DNA in the sample containing DNA originating from colon cells are amplified.

3. The method of claim 1, wherein:
   following step (b), contacting the treated DNA, or a treated fragment thereof, with an amplification enzyme and at least two primers comprising, in each case a contiguous sequence at least 18 nucleotides in length that is complementary to, or hybridizes to a sequence selected from the group consisting of SEQ ID NOS:2 to 5, and complements thereof; and
   determining, based on the presence or absence of said amplificate a methylation state of at least one CpG dinucleotide sequence of SEQ ID NO:1, or an average, or a value reflecting an average methylation state of a plurality of CpG dinucleotide sequences of SEQ ID NO:1.

4. The method of claim 1, wherein the biological sample obtained from the subject is selected from the group consisting of histological slides, biopsies, paraffin-embedded tissue, bodily fluids, serum, colon tissue, plasma, stool, urine, blood, and combinations thereof.

* * * * *